(12) United States Patent
Bengea et al.

(10) Patent No.: US 9,062,106 B2
(45) Date of Patent: Jun. 23, 2015

(54) METHODS FOR CONTROLLING THE GALACTOSYLATION PROFILE OF RECOMBINANTLY-EXPRESSED PROTEINS

(75) Inventors: Cornelia Bengea, Auburn, MA (US); Lisa M. Rives, Natick, MA (US); Patrick Hossler, Westborough, MA (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/457,020

(22) Filed: Apr. 26, 2012

(65) Prior Publication Data

US 2012/0276631 A1    Nov. 1, 2012

Related U.S. Application Data

(60) Provisional application No. 61/479,727, filed on Apr. 27, 2011.

(51) Int. Cl.
| | |
|---|---|
| *A61K 39/00* | (2006.01) |
| *A61K 38/00* | (2006.01) |
| *C12P 21/04* | (2006.01) |
| *C12P 21/08* | (2006.01) |
| *C07K 16/00* | (2006.01) |
| *C07K 16/24* | (2006.01) |
| *C12N 5/00* | (2006.01) |
| *C12P 21/00* | (2006.01) |

(52) U.S. Cl.
CPC ............ *C07K 16/241* (2013.01); *C12N 5/0018* (2013.01); *C12N 2500/20* (2013.01); *C12N 2500/34* (2013.01); *C12N 2511/00* (2013.01); *C12P 21/005* (2013.01); *C07K 16/00* (2013.01); *C07K 2317/41* (2013.01); *C07K 2317/21* (2013.01)

(58) Field of Classification Search
CPC .. C12N 5/0018; C12P 21/005; C07K 16/241; C07K 16/00
See application file for complete search history.

(56) References Cited

U.S. PATENT DOCUMENTS

| | | |
|---|---|---|
| RE30,985 E | 6/1982 | Cartaya |
| 4,399,216 A | 8/1983 | Axel et al. |
| 4,510,245 A | 4/1985 | Cousens et al. |
| 4,560,655 A | 12/1985 | Baker |
| 4,634,665 A | 1/1987 | Axel et al. |

(Continued)

FOREIGN PATENT DOCUMENTS

| | | |
|---|---|---|
| CN | 1563090 A | 1/2005 |
| DE | 3631229 A1 | 3/1988 |

(Continued)

OTHER PUBLICATIONS

Gramer et al., (Biotechnol Bioeng. Jul. 2011;108(7):1591-602. Epub Feb. 18, 2011).*
Gramer et al., (Biotech Bioengin. 2011;(108):1591-1602. ePub Feb. 18, 2011).*
Andersen et al. (Curr Opin Biotech 1994 5:546-549).*
Goochee et al., (Biotechnology, Dec. 9, 1991:1346-1355).*
Parekh et al., (TIBTECH, May 7, 1989:117-122)).*
Harlow et al., Eds ("Antibodies: A Laboratory Manual" 1988. Cold Spring Harbor Laboratory Press, Chapter 7, pp. 245, 247, and 253).*

(Continued)

*Primary Examiner* — Cherie M Stanfield
(74) *Attorney, Agent, or Firm* — McCarter & English, LLP; Maria Laccotripe Zacharakis

(57) ABSTRACT

The present invention relates to methods for modulating the glycosylation profile of recombinantly-expressed proteins. In particular, the present invention relates to methods of controlling the galactosylation profile of recombinantly-expressed proteins by supplementing production medium, e.g., a hydrolysate-based or a chemically defined medium, with manganese and/or D-galactose.

65 Claims, 40 Drawing Sheets

(56) References Cited

U.S. PATENT DOCUMENTS

| | | |
|---|---|---|
| 4,657,866 A | 4/1987 | Kumar |
| 4,767,704 A | 8/1988 | Cleveland et al. |
| 4,801,687 A | 1/1989 | Ngo |
| 4,816,397 A | 3/1989 | Boss et al. |
| 4,877,608 A | 10/1989 | Lee et al. |
| 4,927,762 A | 5/1990 | Darfler |
| 4,933,435 A | 6/1990 | Ngo |
| 4,968,615 A | 11/1990 | Koszinowski et al. |
| 5,045,468 A | 9/1991 | Darfler |
| 5,096,816 A | 3/1992 | Maiorella |
| 5,110,913 A | 5/1992 | Coan et al. |
| 5,118,796 A | 6/1992 | Prior et al. |
| 5,122,469 A | 6/1992 | Mather et al. |
| 5,126,250 A | 6/1992 | McDonough et al. |
| 5,168,062 A | 12/1992 | Stinski |
| 5,179,017 A | 1/1993 | Axel et al. |
| 5,231,024 A | 7/1993 | Moeller et al. |
| 5,328,985 A | 7/1994 | Sano et al. |
| 5,378,612 A | 1/1995 | Nakashima et al. |
| 5,429,746 A | 7/1995 | Shadle et al. |
| 5,530,101 A | 6/1996 | Queen et al. |
| 5,545,403 A | 8/1996 | Page |
| 5,545,806 A | 8/1996 | Lonberg et al. |
| 5,545,807 A | 8/1996 | Surani et al. |
| 5,561,053 A | 10/1996 | Crowley |
| 5,569,825 A | 10/1996 | Lonberg et al. |
| 5,625,126 A | 4/1997 | Lonberg et al. |
| 5,633,162 A | 5/1997 | Keen et al. |
| 5,633,425 A | 5/1997 | Lonberg et al. |
| 5,644,036 A | 7/1997 | Ramage et al. |
| 5,654,407 A | 8/1997 | Boyle et al. |
| 5,656,272 A | 8/1997 | Le et al. |
| 5,661,016 A | 8/1997 | Lonberg et al. |
| 5,672,347 A | 9/1997 | Aggarwal et al. |
| 5,672,502 A | 9/1997 | Birch et al. |
| 5,698,195 A | 12/1997 | Le et al. |
| 5,705,364 A | 1/1998 | Etcheverry et al. |
| 5,721,121 A | 2/1998 | Etcheverry et al. |
| 5,770,429 A | 6/1998 | Lonberg et al. |
| 5,789,650 A | 8/1998 | Lonberg et al. |
| 5,795,967 A | 8/1998 | Aggarwal et al. |
| 5,811,299 A | 9/1998 | Renner et al. |
| 5,859,205 A | 1/1999 | Adair et al. |
| 5,876,961 A | 3/1999 | Crowe et al. |
| 5,877,293 A | 3/1999 | Adair et al. |
| 5,929,212 A | 7/1999 | Jolliffe et al. |
| 5,945,098 A | 8/1999 | Sarno et al. |
| 5,976,833 A | 11/1999 | Furukawa et al. |
| 5,994,510 A | 11/1999 | Adair et al. |
| 6,024,938 A | 2/2000 | Corbo et al. |
| 6,036,978 A | 3/2000 | Gombotz et al. |
| 6,048,728 A | 4/2000 | Inlow et al. |
| 6,066,719 A | 5/2000 | Zapata |
| 6,075,181 A | 6/2000 | Kucherlapati et al. |
| 6,090,382 A * | 7/2000 | Salfeld et al. ............ 424/133.1 |
| 6,113,898 A | 9/2000 | Anderson et al. |
| 6,150,584 A | 11/2000 | Kucherlapati et al. |
| 6,171,586 B1 | 1/2001 | Lam et al. |
| 6,255,458 B1 | 7/2001 | Lonberg et al. |
| 6,258,562 B1 | 7/2001 | Salfeld et al. |
| 6,270,766 B1 | 8/2001 | Feldman et al. |
| 6,300,129 B1 | 10/2001 | Lonberg et al. |
| 6,339,142 B1 | 1/2002 | Basey et al. |
| 6,399,381 B1 | 6/2002 | Blum et al. |
| 6,406,909 B1 | 6/2002 | Shibuya et al. |
| 6,410,270 B1 | 6/2002 | Strittmatter et al. |
| 6,413,746 B1 | 7/2002 | Field |
| 6,436,397 B1 | 8/2002 | Baker et al. |
| 6,448,380 B2 | 9/2002 | Rathjen et al. |
| 6,451,983 B2 | 9/2002 | Rathjen et al. |
| 6,489,447 B1 | 12/2002 | Basey et al. |
| 6,498,237 B2 | 12/2002 | Rathjen et al. |
| 6,509,015 B1 | 1/2003 | Salfeld et al. |
| 6,528,286 B1 | 3/2003 | Ryll |
| 6,593,458 B1 | 7/2003 | Rathjen et al. |
| 6,673,986 B1 | 1/2004 | Kucherlapati et al. |
| 6,680,181 B2 | 1/2004 | Castan |
| 6,870,034 B2 | 3/2005 | Breece et al. |
| 6,872,549 B2 | 3/2005 | Van Ness et al. |
| 6,890,736 B1 | 5/2005 | Reddy et al. |
| 6,900,056 B2 | 5/2005 | Lee et al. |
| 6,914,128 B1 | 7/2005 | Salfeld et al. |
| 6,924,124 B1 | 8/2005 | Singh |
| 6,974,681 B1 | 12/2005 | McGrew |
| 7,070,775 B2 | 7/2006 | Le et al. |
| 7,084,260 B1 | 8/2006 | Lonberg et al. |
| 7,122,641 B2 | 10/2006 | Vedantham et al. |
| 7,189,820 B2 | 3/2007 | Ruben |
| 7,192,584 B2 | 3/2007 | Le et al. |
| 7,223,394 B2 | 5/2007 | Salfeld et al. |
| 7,250,165 B2 | 7/2007 | Heavner et al. |
| 7,276,239 B2 | 10/2007 | Le et al. |
| 7,323,553 B2 | 1/2008 | Fahrner et al. |
| 7,332,303 B2 * | 2/2008 | Schilling et al. ............ 435/69.7 |
| 7,390,660 B2 | 6/2008 | Behrendt et al. |
| 7,429,491 B2 | 9/2008 | Luan et al. |
| 7,504,485 B2 | 3/2009 | Salfeld et al. |
| 7,521,206 B2 | 4/2009 | Heavner et al. |
| 7,521,210 B2 | 4/2009 | Knudsen |
| 7,541,031 B2 | 6/2009 | Salfeld et al. |
| 7,588,761 B2 | 9/2009 | Salfeld et al. |
| 7,645,609 B2 | 1/2010 | Follstad |
| 7,714,112 B2 | 5/2010 | Engstrand et al. |
| 7,750,129 B2 | 7/2010 | Johansson et al. |
| 7,767,207 B2 | 8/2010 | Ghayer et al. |
| 7,863,426 B2 | 1/2011 | Wan et al. |
| 7,883,704 B2 | 2/2011 | Salfeld et al. |
| 7,919,264 B2 | 4/2011 | Maksymowych et al. |
| 7,947,471 B2 | 5/2011 | Knudsen |
| 7,972,810 B2 | 7/2011 | Crowell et al. |
| 8,067,182 B2 | 11/2011 | Kelley et al. |
| 8,093,045 B2 | 1/2012 | Pla et al. |
| 8,192,951 B2 | 6/2012 | Wang et al. |
| 8,197,813 B2 | 6/2012 | Salfeld et al. |
| 8,206,714 B2 | 6/2012 | Salfeld et al. |
| 8,209,132 B2 | 6/2012 | Bosques et al. |
| 8,216,583 B2 | 7/2012 | Kruase et al. |
| 8,231,876 B2 | 7/2012 | Wan et al. |
| 8,361,797 B2 | 1/2013 | Osborne et al. |
| 8,372,400 B2 | 2/2013 | Salfeld et al. |
| 8,372,401 B2 | 2/2013 | Salfeld et al. |
| 8,414,894 B2 | 4/2013 | Salfeld et al. |
| 8,420,081 B2 | 4/2013 | Fraunhofer et al. |
| 8,436,149 B2 | 5/2013 | Borhani et al. |
| 8,470,552 B2 | 6/2013 | Croughan et al. |
| 8,663,945 B2 | 3/2014 | Pla et al. |
| 8,753,633 B2 | 6/2014 | Salfeld et al. |
| 8,821,865 B2 | 9/2014 | Neu et al. |
| 8,883,146 B2 | 11/2014 | Fraunhofer et al. |
| 8,883,156 B2 | 11/2014 | Wan et al. |
| 8,895,009 B2 | 11/2014 | Wan et al. |
| 8,895,709 B2 | 11/2014 | Hickman et al. |
| 8,906,372 B2 | 12/2014 | Wan et al. |
| 8,906,646 B2 | 12/2014 | Pla et al. |
| 8,911,964 B2 | 12/2014 | Pla et al. |
| 8,916,153 B2 | 12/2014 | Wan et al. |
| 8,921,526 B2 | 12/2014 | Chumsae et al. |
| 8,946,395 B1 | 2/2015 | Herigstad et al. |
| 2002/0045207 A1 | 4/2002 | Krummen et al. |
| 2002/0132299 A1 | 9/2002 | Field |
| 2002/0187526 A1 | 12/2002 | Ruben et al. |
| 2003/0012786 A1 | 1/2003 | Teoh et al. |
| 2003/0049725 A1 | 3/2003 | Heavner et al. |
| 2003/0096414 A1 | 5/2003 | Ciccarone et al. |
| 2003/0125247 A1 | 7/2003 | Rosen et al. |
| 2003/0153735 A1 | 8/2003 | Breece et al. |
| 2003/0157108 A1 | 8/2003 | Presta |
| 2003/0161828 A1 | 8/2003 | Abdelghany et al. |
| 2003/0166869 A1 | 9/2003 | Vedantham et al. |
| 2003/0175884 A1 | 9/2003 | Umana et al. |
| 2003/0178368 A1 | 9/2003 | van Reis |
| 2003/0206898 A1 | 11/2003 | Fischkoff et al. |
| 2003/0219438 A1 | 11/2003 | Salfeld et al. |
| 2003/0229212 A1 | 12/2003 | Fahrner et al. |

(56) References Cited

U.S. PATENT DOCUMENTS

| | | |
|---|---|---|
| 2003/0235585 A1 | 12/2003 | Fischkoff et al. |
| 2004/0009172 A1 | 1/2004 | Fischkoff et al. |
| 2004/0029229 A1 | 2/2004 | Reeves et al. |
| 2004/0033228 A1 | 2/2004 | Krause et al. |
| 2004/0038878 A1 | 2/2004 | Tanikawa et al. |
| 2004/0101939 A1 | 5/2004 | Santora et al. |
| 2004/0120952 A1 | 6/2004 | Knight et al. |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0132140 A1 | 7/2004 | Satoh et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0162414 A1 | 8/2004 | Santora et al. |
| 2004/0166111 A1 | 8/2004 | Kaymakcalan et al. |
| 2004/0171152 A1 | 9/2004 | Price et al. |
| 2004/0191243 A1 | 9/2004 | Chen et al. |
| 2004/0214289 A1 | 10/2004 | deVries et al. |
| 2004/0219142 A1 | 11/2004 | Banerjee et al. |
| 2005/0004354 A1 | 1/2005 | Salfeld et al. |
| 2005/0100965 A1 | 5/2005 | Ghayur et al. |
| 2005/0123541 A1 | 6/2005 | Heavner et al. |
| 2005/0175611 A1 | 8/2005 | Mahler et al. |
| 2005/0249735 A1 | 11/2005 | Le et al. |
| 2005/0271654 A1 | 12/2005 | Rinderknecht et al. |
| 2005/0272124 A1 | 12/2005 | Chen et al. |
| 2006/0009385 A1 | 1/2006 | Hoffman et al. |
| 2006/0018907 A1 | 1/2006 | Le et al. |
| 2006/0024293 A1 | 2/2006 | Salfeld et al. |
| 2006/0083741 A1 | 4/2006 | Hoffman et al. |
| 2006/0149042 A1 | 7/2006 | Konstantinov et al. |
| 2006/0246073 A1 | 11/2006 | Knight et al. |
| 2006/0252672 A1 | 11/2006 | Betenbaugh et al. |
| 2006/0269479 A1 | 11/2006 | Colton et al. |
| 2006/0287432 A1 | 12/2006 | Christensen et al. |
| 2007/0003548 A1 | 1/2007 | Heavner et al. |
| 2007/0004009 A1 | 1/2007 | Dixit et al. |
| 2007/0041905 A1 | 2/2007 | Hoffman et al. |
| 2007/0060741 A1 | 3/2007 | Kelley et al. |
| 2007/0071747 A1 | 3/2007 | Hoffman et al. |
| 2007/0081996 A1 | 4/2007 | Hoffman et al. |
| 2007/0110743 A1 | 5/2007 | Drapeau et al. |
| 2007/0111284 A1 | 5/2007 | Ryll |
| 2007/0161084 A1* | 7/2007 | Crowell et al. ............... 435/69.1 |
| 2007/0172475 A1 | 7/2007 | Matheus et al. |
| 2007/0172897 A1 | 7/2007 | Maksymowych et al. |
| 2007/0184045 A1 | 8/2007 | Doctor et al. |
| 2007/0184529 A1 | 8/2007 | Etcheverry et al. |
| 2007/0190057 A1 | 8/2007 | Wu et al. |
| 2007/0196373 A1 | 8/2007 | Le et al. |
| 2007/0202051 A1 | 8/2007 | Schuschnig |
| 2007/0202104 A1 | 8/2007 | Banerjee et al. |
| 2007/0269463 A1 | 11/2007 | Donovan |
| 2007/0292442 A1 | 12/2007 | Wan et al. |
| 2007/0298040 A1 | 12/2007 | Le et al. |
| 2008/0025976 A1 | 1/2008 | Le et al. |
| 2008/0112953 A1 | 5/2008 | McAuley et al. |
| 2008/0118496 A1 | 5/2008 | Medich et al. |
| 2008/0131374 A1 | 6/2008 | Medich et al. |
| 2008/0160577 A1 | 7/2008 | Dell'Orco et al. |
| 2008/0166348 A1 | 7/2008 | Kupper et al. |
| 2008/0193466 A1 | 8/2008 | Banerjee et al. |
| 2008/0219952 A1 | 9/2008 | Fischer et al. |
| 2008/0227136 A1 | 9/2008 | Pla et al. |
| 2008/0269132 A1 | 10/2008 | Gomes et al. |
| 2008/0269468 A1 | 10/2008 | Vogel et al. |
| 2008/0274507 A1 | 11/2008 | Gomes et al. |
| 2008/0292642 A1 | 11/2008 | Borhani et al. |
| 2008/0305114 A1 | 12/2008 | Salfeld et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0053786 A1 | 2/2009 | Kao et al. |
| 2009/0068172 A1 | 3/2009 | Kaymakcalan et al. |
| 2009/0068705 A1 | 3/2009 | Drapeau et al. |
| 2009/0110679 A1 | 4/2009 | Li et al. |
| 2009/0123378 A1 | 5/2009 | Wong et al. |
| 2009/0142828 A1 | 6/2009 | Bucciarelli et al. |
| 2009/0148513 A1 | 6/2009 | Fraunhofer et al. |
| 2009/0155205 A1 | 6/2009 | Salfeld et al. |
| 2009/0175857 A1 | 7/2009 | Salfeld et al. |
| 2009/0202546 A1 | 8/2009 | Harris et al. |
| 2009/0202557 A1 | 8/2009 | Argiriadi et al. |
| 2009/0203055 A1 | 8/2009 | Ngantung et al. |
| 2009/0208500 A1 | 8/2009 | Joly et al. |
| 2009/0226530 A1 | 9/2009 | Lassner et al. |
| 2009/0239259 A1 | 9/2009 | Hsieh |
| 2009/0258018 A1 | 10/2009 | Medich et al. |
| 2009/0269302 A1 | 10/2009 | Salfeld et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong |
| 2010/0034823 A1 | 2/2010 | Borhani et al. |
| 2010/0040604 A1 | 2/2010 | Salfeld et al. |
| 2010/0040630 A1 | 2/2010 | Elden et al. |
| 2010/0135987 A1 | 6/2010 | Hickman et al. |
| 2010/0136025 A1 | 6/2010 | Hickman et al. |
| 2010/0160894 A1 | 6/2010 | Julian et al. |
| 2010/0221823 A1 | 9/2010 | McCoy et al. |
| 2010/0256336 A1 | 10/2010 | Yuk et al. |
| 2010/0278822 A1 | 11/2010 | Fraunhofer et al. |
| 2010/0297697 A1 | 11/2010 | Ambrosius et al. |
| 2011/0002935 A1 | 1/2011 | Wan et al. |
| 2011/0003338 A1 | 1/2011 | Bayer et al. |
| 2011/0053223 A1 | 3/2011 | Bayer et al. |
| 2011/0053265 A1 | 3/2011 | Follstad et al. |
| 2011/0054414 A1 | 3/2011 | Shang et al. |
| 2011/0081679 A1 | 4/2011 | Jing et al. |
| 2011/0081700 A1 | 4/2011 | Hasslacher et al. |
| 2011/0086798 A1 | 4/2011 | Sethuraman et al. |
| 2011/0097336 A1 | 4/2011 | Wu et al. |
| 2011/0123544 A1 | 5/2011 | Salfeld et al. |
| 2011/0130544 A1 | 6/2011 | Ram et al. |
| 2011/0171227 A1 | 7/2011 | Okun et al. |
| 2011/0207676 A1 | 8/2011 | Callewaert et al. |
| 2011/0300151 A1 | 12/2011 | Okun et al. |
| 2012/0014956 A1 | 1/2012 | Kupper et al. |
| 2012/0015438 A1 | 1/2012 | Schilling et al. |
| 2012/0039900 A1 | 2/2012 | Stuhlmuller et al. |
| 2012/0039908 A1 | 2/2012 | Combs et al. |
| 2012/0077213 A1 | 3/2012 | Pla et al. |
| 2012/0107783 A1 | 5/2012 | Julian et al. |
| 2012/0123688 A1 | 5/2012 | Ramasubramanyan et al. |
| 2012/0129185 A1 | 5/2012 | Maksymowych et al. |
| 2012/0171123 A1 | 7/2012 | Medich et al. |
| 2012/0177596 A1 | 7/2012 | Fischkoff et al. |
| 2012/0178107 A1 | 7/2012 | Salfeld et al. |
| 2012/0183997 A1 | 7/2012 | Alley et al. |
| 2012/0190005 A1 | 7/2012 | Schaub et al. |
| 2012/0201831 A1 | 8/2012 | Salfeld et al. |
| 2012/0213792 A1 | 8/2012 | Salfeld et al. |
| 2012/0219564 A1 | 8/2012 | Salfeld et al. |
| 2012/0238730 A1 | 9/2012 | Dong et al. |
| 2012/0244168 A1 | 9/2012 | Salfeld et al. |
| 2012/0251550 A1 | 10/2012 | Borhani et al. |
| 2012/0258114 A1 | 10/2012 | Salfeld et al. |
| 2012/0263731 A1 | 10/2012 | Fraunhofer et al. |
| 2012/0264920 A1 | 10/2012 | Wang et al. |
| 2012/0277165 A1 | 11/2012 | Collins et al. |
| 2012/0282262 A1 | 11/2012 | Okun et al. |
| 2012/0282270 A1 | 11/2012 | Krause et al. |
| 2012/0288494 A1 | 11/2012 | Borhani et al. |
| 2012/0308514 A1 | 12/2012 | Salfeld et al. |
| 2013/0004507 A1 | 1/2013 | Fischkoff et al. |
| 2013/0028903 A1 | 1/2013 | Wan et al. |
| 2013/0309242 A1 | 1/2013 | Aidasani et al. |
| 2013/0065219 A1 | 3/2013 | Tsang et al. |

(56) References Cited

U.S. PATENT DOCUMENTS

| | | |
|---|---|---|
| 2013/0084605 A1 | 4/2013 | Zhou et al. |
| 2013/0096283 A1 | 4/2013 | Khetan et al. |
| 2013/0115224 A1 | 5/2013 | Salfeld et al. |
| 2013/0122011 A1 | 5/2013 | Hoffman et al. |
| 2013/0122018 A1 | 5/2013 | Salfeld et al. |
| 2013/0156760 A1 | 6/2013 | Fraunhofer et al. |
| 2013/0195888 A1 | 8/2013 | Wang et al. |
| 2013/0205604 A1 | 8/2013 | Esenwein et al. |
| 2013/0243786 A1 | 9/2013 | Banerjee et al. |
| 2013/0273059 A1 | 10/2013 | Wan et al. |
| 2013/0280267 A1 | 10/2013 | Wan et al. |
| 2013/0280274 A1 | 10/2013 | Subramanian et al. |
| 2013/0323261 A1 | 12/2013 | Wan et al. |
| 2013/0330356 A1 | 12/2013 | Salfeld et al. |
| 2013/0330357 A1 | 12/2013 | Salfeld et al. |
| 2013/0336957 A1 | 12/2013 | Wang et al. |
| 2013/0338344 A1 | 12/2013 | Ramasubramanyan et al. |
| 2013/0344084 A1 | 12/2013 | Subramanian et al. |
| 2014/0010820 A1 | 1/2014 | Wang et al. |
| 2014/0065710 A1 | 3/2014 | Rives et al. |
| 2014/0072585 A1 | 3/2014 | Herigstad et al. |
| 2014/0120583 A1 | 5/2014 | Prentice |
| 2014/0134674 A1 | 5/2014 | Pla et al. |
| 2014/0134675 A1 | 5/2014 | Pla et al. |
| 2014/0141007 A1 | 5/2014 | Fraunhofer et al. |
| 2014/0141008 A1 | 5/2014 | Fraunhofer et al. |
| 2014/0154270 A1 | 6/2014 | Wang et al. |
| 2014/0178984 A1 | 6/2014 | Jerums et al. |
| 2014/0206038 A1 | 7/2014 | Pla et al. |
| 2014/0234905 A1 | 8/2014 | Pla et al. |
| 2014/0255423 A1 | 9/2014 | Hickman et al. |
| 2014/0271626 A1 | 9/2014 | Chumsae et al. |
| 2014/0271632 A1 | 9/2014 | Nossler at al. |
| 2014/0271633 A1 | 9/2014 | Hossler |
| 2014/0275494 A1 | 9/2014 | Wang et al. |
| 2014/0314745 A1 | 10/2014 | Rives et al. |
| 2014/0377275 A1 | 12/2014 | Neu et al. |

FOREIGN PATENT DOCUMENTS

| | | |
|---|---|---|
| EP | 0101681 A1 | 3/1984 |
| EP | 0173177 A1 | 3/1986 |
| EP | 0186833 A2 | 7/1986 |
| EP | 0212489 A2 | 3/1987 |
| EP | 0351789 A2 | 1/1990 |
| EP | 0366043 A1 | 5/1990 |
| EP | 0460426 B1 | 12/1991 |
| EP | 0481791 A2 | 4/1992 |
| EP | 0492448 A1 | 7/1992 |
| EP | 0523949 A1 | 1/1993 |
| EP | 0612251 A1 | 8/1994 |
| EP | 0614984 A2 | 9/1994 |
| EP | 0659766 A1 | 6/1995 |
| EP | 0746398 A1 | 12/1996 |
| EP | 0764719 A2 | 3/1997 |
| EP | 0956873 A2 | 11/1999 |
| EP | 0956875 A2 | 11/1999 |
| EP | 1075488 A1 | 2/2001 |
| EP | 1174148 A1 | 1/2002 |
| EP | 1221476 A2 | 7/2002 |
| EP | 1254666 A1 | 11/2002 |
| EP | 1308455 A2 | 5/2003 |
| EP | 1308456 A2 | 5/2003 |
| EP | 1418967 A2 | 5/2004 |
| EP | 1568388 A1 | 8/2005 |
| EP | 1745141 A1 | 1/2007 |
| EP | 1851305 A1 | 11/2007 |
| EP | 2080809 A1 | 7/2009 |
| EP | 2144929 A1 | 1/2010 |
| EP | 2152856 A1 | 2/2010 |
| EP | 2213726 A1 | 8/2010 |
| EP | 2357250 A2 | 8/2011 |
| EP | 2495307 A1 | 9/2012 |
| EP | 2528002 A2 | 11/2012 |
| EP | 2574677 A1 | 4/2013 |
| GB | 2160530 A | 12/1985 |
| GB | 2279077 A | 12/1994 |
| JP | 7289288 A | 11/1995 |
| WO | WO 87/00195 | 1/1987 |
| WO | WO 90/03430 | 4/1990 |
| WO | WO-90/05144 A1 | 5/1990 |
| WO | WO-91/02078 A1 | 2/1991 |
| WO | WO-91/09967 A1 | 7/1991 |
| WO | WO-92/01047 A1 | 1/1992 |
| WO | WO-92/11383 A1 | 7/1992 |
| WO | WO-92/16553 A1 | 10/1992 |
| WO | WO-93/06213 A1 | 4/1993 |
| WO | WO-94/02602 A1 | 2/1994 |
| WO | WO-94/08619 A1 | 4/1994 |
| WO | WO-94/25585 A1 | 11/1994 |
| WO | WO-94/26910 A1 | 11/1994 |
| WO | WO-94/29347 A1 | 12/1994 |
| WO | WO-9511317 A1 | 4/1995 |
| WO | WO-95/23813 A1 | 9/1995 |
| WO | WO-96/33208 A1 | 10/1996 |
| WO | WO-96/33735 A1 | 10/1996 |
| WO | WO-96/34096 A1 | 10/1996 |
| WO | WO-9704801 A1 | 2/1997 |
| WO | WO-97/13852 A1 | 4/1997 |
| WO | WO-97/29131 A1 | 8/1997 |
| WO | WO-98/23645 A1 | 6/1998 |
| WO | WO-98/24883 A2 | 6/1998 |
| WO | WO-98/24884 A1 | 6/1998 |
| WO | WO-98/24893 A2 | 6/1998 |
| WO | WO-98/50433 A2 | 11/1998 |
| WO | WO-9856418 A1 | 12/1998 |
| WO | WO-99/32605 A1 | 7/1999 |
| WO | WO-99/57134 A1 | 11/1999 |
| WO | WO-99/57246 A1 | 11/1999 |
| WO | WO-0003000 A2 | 1/2000 |
| WO | WO-01-44442 A1 | 6/2001 |
| WO | WO-0147554 A1 | 7/2001 |
| WO | WO-01-59069 A1 | 8/2001 |
| WO | WO-0177362 A1 | 10/2001 |
| WO | WO-02/12502 A2 | 2/2002 |
| WO | WO-0212501 A2 | 2/2002 |
| WO | WO-03045995 A2 | 6/2003 |
| WO | WO-03/059935 A2 | 7/2003 |
| WO | WO-03/066662 A2 | 8/2003 |
| WO | WO-2004008100 A2 | 1/2004 |
| WO | WO-2004/058944 A2 | 7/2004 |
| WO | WO-2004058800 A2 | 7/2004 |
| WO | WO-2004/097006 A1 | 11/2004 |
| WO | WO-2005042569 A1 | 5/2005 |
| WO | WO-2005/082483 A1 | 9/2005 |
| WO | WO-2006/043895 A1 | 4/2006 |
| WO | WO-2006045438 A1 | 5/2006 |
| WO | WO-2006/110277 A1 | 10/2006 |
| WO | WO-2007/087384 A2 | 8/2007 |
| WO | WO-2007/117490 A2 | 10/2007 |
| WO | WO-2008/033517 A2 | 3/2008 |
| WO | WO-2008-057240 A2 | 5/2008 |
| WO | WO-2008068879 A1 | 6/2008 |
| WO | WO-2008087184 A2 | 7/2008 |
| WO | WO-2008121616 A2 | 10/2008 |
| WO | WO-2008135498 A2 | 11/2008 |
| WO | WO-2009/027041 A1 | 1/2009 |
| WO | WO-2009023562 A2 | 2/2009 |
| WO | WO-2009058769 A1 | 5/2009 |
| WO | WO-2009/073569 A2 | 6/2009 |
| WO | WO-2009135656 A1 | 11/2009 |
| WO | WO-2010036443 A1 | 4/2010 |
| WO | WO-2010043703 A1 | 4/2010 |
| WO | WO-2010122460 A1 | 10/2010 |
| WO | WO-2010/129469 A1 | 11/2010 |
| WO | WO-2010127069 A1 | 11/2010 |
| WO | WO-2011005773 A2 | 1/2011 |
| WO | WO-2011009623 A1 | 1/2011 |
| WO | WO-2011-019619 A1 | 2/2011 |
| WO | WO-2011015926 A1 | 2/2011 |
| WO | WO-2011024025 A1 | 3/2011 |
| WO | WO-2011044180 A1 | 4/2011 |
| WO | WO-2011/073235 A1 | 6/2011 |

(56) References Cited

FOREIGN PATENT DOCUMENTS

| WO | WO-2011069056 A2 | 6/2011 |
|---|---|---|
| WO | WO-2011098526 A1 | 8/2011 |
| WO | WO-2011110598 A1 | 9/2011 |
| WO | WO-2011/133886 A2 | 10/2011 |
| WO | WO-2011127322 A1 | 10/2011 |
| WO | WO-2011134919 A2 | 11/2011 |
| WO | WO-2011134920 A1 | 11/2011 |
| WO | WO-2012019160 A1 | 2/2012 |
| WO | WO-2012030512 A1 | 3/2012 |
| WO | WO-2012050175 A1 | 4/2012 |
| WO | WO-2012051147 A1 | 4/2012 |
| WO | WO-2012/065072 A2 | 5/2012 |
| WO | WO-2012062810 A2 | 5/2012 |
| WO | WO-2012120500 A2 | 9/2012 |
| WO | WO-2012140138 A1 | 10/2012 |
| WO | WO-2012145682 A1 | 10/2012 |
| WO | WO-2012/149197 A2 | 11/2012 |
| WO | WO-2012147048 A2 | 11/2012 |
| WO | WO-2012147053 A1 | 11/2012 |
| WO | WO-2012158551 A1 | 11/2012 |
| WO | WO-2013-011076 A2 | 1/2013 |
| WO | WO-2013006461 A1 | 1/2013 |
| WO | WO-2013006479 A2 | 1/2013 |
| WO | WO-2013009648 A2 | 1/2013 |
| WO | WO-2013013013 A2 | 1/2013 |
| WO | WO-2013-158273 A1 | 10/2013 |
| WO | WO-2013-158279 A1 | 10/2013 |
| WO | WO-2013158275 A1 | 10/2013 |
| WO | WO-2013-176754 A1 | 11/2013 |
| WO | WO-2013-177115 A2 | 11/2013 |
| WO | WO-2013-177118 A2 | 11/2013 |
| WO | WO-2013-181585 A2 | 12/2013 |

OTHER PUBLICATIONS

Sigma Catalog "RPMI1640" (last accessed Nov. 17, 2014).*
HyClone™ CDM4CHO Catalog listing (last accessed Nov. 17, 2014).*
Sigma MSDS for RMPI1640 (last accessed Nov. 17, 2014).*
TESS database "HYCLONE" Trademark #76244963. Filing date Apr. 23, 2001. Live mark. Last accessed Nov. 17, 2014.*
TESS database "HYCLONE" Trademark #85769283. Filing date Sep. 30, 2012. Live mark. Last accessed Nov. 17, 2014.*
International Search Report and Written Opinion for PCT/US2012/035266, dated Feb. 7, 2013 (corresponds to U.S. Appl. No. 13/547,020).
Gramer. et al., "Modulation of Antibody Galactosylation Through Feeding of Uridine, Manganese Chloride, and Galactose", *Biotechnology and Bioengineering*, 108(7):1591-1602 (2011).
Gramer, M.J., et al., "Manipulation of Antibody Glycoforms in a High-Yield GS-CHO Process to Meet Comparability Requirements", poster presented at the BioProcess International Conference and Exhibition, Sep. 2010.
"Genentech unveils production capacity hikes," in-Pharma Technologist.com Jun. 28, 2005, pp. 1-2.
"Memorandum in Support of Centocor's Motion for Summary Judgment No. 1 that All Asserted Claims Are Invalid for Lack of Written Description", dated Aug. 1, 2013 and submitted by defendant in Civil Action No. 09-40089-FDS, 28 pages.
"Memorandum in Support of Centocor's Motion for Summary Judgment No. 2 that All Asserted Claims Are Invalid for Lack of Enablement", dated Aug. 1, 2013 and submitted by defendant in Civil Action No. 09-40089-FDS, 22 pages.
"Memorandum in Support of Centocor's Motion for Summary Judgment No. 4 that Claims Encompassing Non-recombinant Human Antibodies Are Invalid for Failing to Meet the Requirements of 35 U.S.C. §112", dated Aug. 1, 2013 and submitted by defendant in Civil Action No. 09-40089-FDS, 21 pages.
"Memorandum in Support of Centocor's Motion No. 3 for Summary Judgment that the 394 and 031 Patents Are Invalid for Under 35 U.S.C. §102(f) for Failing to Name the Proper Inventors", dated Aug. 1, 2013 and submitted by defendant in Civil Action No. 09-40089-FDS, 13 pages.
"Memorandum in Support of Centocor's Motion No. 6 for Summary Judgment that References Dated Before Feb. 10, 1997 Qualify as Prior Art to the 394 and 031 Patents", dated Aug. 1, 2013 and submitted by defendant in Civil Action No. 09-40089-FDS, 16 pages.
"Plaintiffs' Memorandum in Support of Their Motion for Partial Summary Judgment", dated Aug. 1, 2013 and submitted by plaintiff in Civil Action No. 09-40089-FDS, 49 pages.
"Plaintiffs' Rule 56.1 Statement of Undisputed Material Facts in Support of Their Motion for Partial Summary Judgment", dated Aug. 1, 2013 and submitted by plaintiff in Civil Action No. 09-40089-FDS, 13 pages.
Abbott Laboratories Press Release, "Abbott Laboratories Receives FDA Approval Earlier Than Expected for HUMIRA (adalimumab) for the Treatment of Rheumatoid Arthritis," Dec. 31, 2002, pp. 1-4.
Abraham, E., et al., "Efficacy and Safety of Monoclonal Antibody to Human Tumor Necrosis Factor α in Patients with Sepsis Syndrome," *JAMA*, vol. 273(12):934-941 (1995).
Adams. et al., "Aggressive cutaneous T-cell lymphomas after TNFα blockade," J. Am. Acad. Dermatol 2004;51 :660-2.
Altamirano, C., et al., "Strategies for fed batch cultivation of t-PA producing CHO cells: substitution of glucose and glutamine and rational design of culture medium", *J. Biotechn*. 110:171-179, 2004.
Anonymous, "SACHEM Displacement Chromatography," Aug. 29, 2012, Retrieved from the Internet: //www.dsplacementchromatography.com, retrieved on Jul. 30, 2014.
Antes et al. "Analysis of lysine clipping of a humanized Lewis-Y specific IgG antibody and its relation to Fc-mediated effector function" Journal of Chromatography B:Biomedical Sciences and Applications, Elsevier, Amsterdam, NL, vol. 852, No. 1-2, May 31, 2007, 250-256.
Averginos, Gab '04 Abstracts—GE Healthcare Life Sciences, "HUMIRA manufacturing: challenges and the path taken", France, Oct. 3-5, 2004, published 2005, pp. 14-16.
Avgerinos et al. (GAb '04 Abstracts—GE Healthcare Life Sciences, France Oct. 3-5, 2004, pp. 15-16 published 2005).
Azevedo et al., "Integrated Process for the Purification of Antibodies Combining Aqueous Two-Phase Extraction, Hydrophobic Interaction Chromatography and Size-Exclusion Chromatography", *Journal of Chromatography* (2008) 1213(2): 154-161.
Ballez, J.S. et al., "Plant protein hydrolysates support CHO-320 cells proliferation and recombinant IFN-[gamma] production in suspension and inside microcarriers in protein-free media", *Cytotechnology* 44:3, 103-114, 2004.
Barbuto, J. et al. "Production of Neutralizing Antibodies to Tumor Necrosis Factor by Human Tumor-Infiltrating B Lymphocytes" *Proc. Am. Assoc. Cancer Res*,. 34:487, Abstr. 2904 (1993).
Barnes et al., "Stability of Protein Production from Recombinant Mammalian Cells," Biotechnology and Bioengineering, 81:6, Mar. 20, 2003, pp. 631-639.
BD Bioscience Product Description for BBL Phytone Peptone (Advanced Processing, Third Edition) (Sep. 23, 2010) (www.bdbiosciences.com/external_files/Doc_Recon_2.0/ab/others/Phytone_Soytone.pdf //www.bdbiosciences.com/external_files/Doc_Recon_2.0/ab/others/Phytone_Soytone.pdf>), (last accessed Jan. 8, 2015), 4 pages.
Biblia, T.A. et al., "In Pursuit of the Optimal Fed-Batch Process for Monoclonal Antibody Production", Biotechnol. Prog 11(1):1-13, Jan.-Feb. 1995.
Birch, Jr. et al., "Antibody production", Adv. Drug Delivery Reviews 58:671-685, 2006.
Blaker, GJ, et al., "The Glucose, Insulin and Glutamine Requirements of Suspension Cultures of HeLa Cells in a Defined Culture Medium", J. Cell Sci. 9:529-537, 1971.
Boekstegers, P., et al., "Repeated administration of a F(ab')2 fragment of an anti-tumor necrosis factor alpha monoclonal antibody in patients with severe sepsis: effects on the cardiovascular system and cytokine levels," *Shock*, vol. 1(4):237-245 (1994).
Bollati-Fogolin M., et al., "Temperature Reduction in Cultures of hGM-CSF-expressing CHO Cells: Effects on Productivity and Product Quantity", Biotechnol. Prog. 21:17-21, 2005.

(56) References Cited

OTHER PUBLICATIONS

Bonafede et al. "Cost per treated patient for etanercept, adalimumab, and infliximab across adult indications: a claims analysis" Advances in Therapy, Springer Healthcare Communications, Heidelberg, vol. 29, No. 3, Mar. 9, 2012, 234-248.
Boswell et al. "Effects of Charge on Antibody Tissue Distribution and Pharmacokinetics" Bioconjugate Chem.(21) 2153-2163 (2010).
Boyle, P. et al. "A Novel Monoclonal Human IgM Autoantibody which Binds Recombinant Human and Mouse Tumor Necrosis Factor-α" *Cell. Immunol.*, 152:556-68 (1993).
Boyle, P. et al. "The B5 Monoclonal Human Autoantibody Binds to Cell Surface TNFα on Human Lymphoid Cells and Cell Lines and Appears to Recognize a Novel Epitope" *Cell. Immunol.*, 152:569-81 (1993).
Brekke, O. et al., "Therapeutic Antibodies for Human Diseases at the Dawn of the Twenty-first Century," *Nature*, vol. 2:52-62 (2002).
Brorson et al., "Bracketed Generic Inactivation of Rodent Retroviruses by Low pH Treatment; for Monoclonal Antibodies and Recombinant Proteins," Biotechnology and Bioengineering,; vol. 82(3): 321-329 (2003).
Bruggemann et al., "Production of human antibody repertoires in transgenic mice" Cur. Op. Biotechnol.;455-458 (1997).
Bruggemann, M., Neuberger, M.S., "Strategies for expressing human antibody repertoires in transgenic mice," *Immunol. Today* 17:391-397 (1996).
Burteau et al. (In Vitro Cell Dev Biol—Animal, Jul. / Aug. 2003. 39-291-296).
Byun, et al. Archives of Biochemistry and Biophysics, "Transport of anti-IL-6 binding fragments into cartilage and the effects of injury," 532 (2013), pp. 15-22.
Cai B, et al. "C-Terminal Lysine Processing of Human Immunoglobulin G2 Heavy Chain In Vivo" Biotechnol. Bioeng. 2011;108: 404-412.
Cambridge Antibody Technology, advertisement of phage display services, Science vol. 253, No. 5018 (1991).
Lu et al.: "A T-flask based screening platform for evaluating and identifying plant hydrolysates for a fed-batch cell culture process", Cytotechnology, Kluwer Academic Publishers, DO, vol. 55, No. 1, Aug. 18, 2007, pp. 15-29.
Carter et al., "Humanization of an anti-p185-$^{HER2}$ antibody for human cancer therapy," *Proc. Nat. Acad. Sci*89:4285-4289 (1992).
Chang KH, et al. "N-Acetylcysteine Increases the Biosynthesis of Recombinant EPO in Apoptotic Chinese Hamster Ovary Cells", Free Radic Res. 30(2):85-91, 1999.
Charter, Edward A., "A New Process for the Separation and Purification of Egg Yolk; Antibodies," BASc., The University of British Columbia; A Thesis; Apr. 1993, 163 pages.
Choo et al. "High-level production of a monoclonal antibody in murine myeloma cells by perfusion culture using a gravity settler" Biotechnology Progress, vol. 23, No. 1, Jan. 1, 2007, 225-231.
Chow, A. et al. "Effect of monoclonal antibody on human tumor necrosis factor (TNF MAb) on TNFα, IL-1β, and IL-6 levels in patients with sepsis syndrome" *Clinical Research*, 42:2 299A (1994).
Chua, FKF et al., "Hyper-stimulation of monoclonal antibody production by high osmolarity stress in eRDF medium", J. Biotechnology 37(3):265-275, Nov. 15, 1994.
Chumsae, Chris et al.: "Arginine modifications by methylglyoxal: discovery in a recombinant monoclonal antibody and contribution to acidic species.", Analytical Chemistry Dec. 3, 2013, vol. 85, No. 23, Dec. 3, 2013, pp. 11401-11409.
Chung et al., "Utilization of Lysozyme Charge Ladders to Examine the Effects of Protein Surface; Charqe Distribution on Bindinq Affinity in Ion Exchanqe Systems," Lanqmuir 26(2): 759-768 (2010).
Chung et al., "Cetuximab-Induced Anaphylaxis and IgE Specific for Galactose-α-1, 3-Galactose", *N. Engl. J. Med.*, 358:11, pp. 1109-1117 (2008).
Cleland, J. et al., "A Specific Molar Ratio of Stabilizer to Protein is Required for Storage Stability of a Lyophilized Monoclonal Antibody," *Journal of Pharmaceutical Sciences*, vol. 90(3):310-321 (2001).

Clincke, M. et al., "Effect of surfactant pluronic F-68 on CHO cell growth, metabolism, production, and glycosylation of human recombinant IFN-γ in mild operating conditions," Biotechnol. Prog. 27(1): 181-190, 2011.
Cohen, J., et al., "Intersept: An international, multicenter, placebo-controlled trial of monoclonal anitbody to human tumor necrosis factor-α in patients with sepsis," *Crit Care Med*, vol. 24(9):1431-1440 (1996).
Cox, J. et al. "A directory of human germ-line $V_\kappa$ segments reveals a strong bias in their usage" *Eur. J. Immunol.*, 24(2):827-36 (1994).
Cromwell (GAB'04 Abstracts—GE Healthcare Life Sciences, Franc Oct. 3-5, 2004, pp. 17-18 published 2005).
Daugherty, et al. Formulation and Delivery Issues for Monoclonal Antibody Therapeutics. Advanced Drug Delivery Reviews, 2006. vol. 58, pp. 686-706.
Davies et al., "Antibody VH domains as small recognition units." *Biotechnology*, 13:475-479 (1995).
Department of Surgery, University of Toronto, Annual Report (1998-1999)(348 pages).
DePhillips et al., "Determinants of protein retention characteristics on cation-exchange adsorbents,"; Journal of Chromatograph A, 933:57-72 (2001).
deZongotita et al., "Phosphate feeding improves high-cell-concentration NS0 myeloma cell culture performance for monoclonal antibody production" Biotechnology and Bioengineering. 2000, 69: 566-576.
Dick et al: "C-terminal lysine variants in fully human monoconal antibodies: Investigation of test methods; and possible causes", Biotechnology and Bioengineering, vol. 100, No. 6, Aug. 15, 2008, pp. 1132-1143.
Dolezal, et al., "*Escherichia coli* Expression of a Bifunctional Fab-peptide Epitope Reagent for the Rapid Diagnosis of HIV-1 and HIV-2", *Immunotechnology*, 1:197-209 (1995).
Doring, E., "Identification and Characterization of a TNFa Antagonist Derived from a Monoclonal Antibody" (1994) *Mol. Immunol* .31(14): 1059-1067.
Du et al., "Chromatographic analysis of the acidic and basic species of recombinant monoclonal antibodies" *MAbs*, Sep.-Oct. 2012; 4(5):578-85.
Elliot et al., "Repeated therapy with monoclonal antibody to tumour necrosis factor α (cA2) in patients with rheumatoid arthritis" (1994) *Lancet*, 344:1125-1127.
Elliot, "Treatment of rheumatoid arthritis with chimeric monoclonal antibodies to tumor necrosis factor α" (1993) *Arthritis & Rheumatism*, 36(12):1681-1690.
Ellison, Jay W. et al., "The Nucleotide Sequence of a Human Immunoglobulin C γ $_1$ Gene," Nucleic Acids Research, vol. 10, No. 13 (1982), 9 pages.
Emery, P. "Adalimumab therapy: Clinical findings and implications for integration into clinical guidelines for rheumatoid arthritis." *Drugs of Today*, 41(3): p. 155-163. (2005).
ERBITUX (cetuximab) label, Revised Aug. 2013, 8 pages.
Ewert et al., "Biophysical Properties of Human Antibody Variable Domains," J. Mol. Biol. 324: 531-553 (2003).
Exhibit dated Aug. 1, 2013 and cited by defendant in Civil Action No. 09-40089-FDS providing the Jun. 23, 2009 trial transcript of the PM session in the matter of *Centocor, et al.* v. *Abbott Laboratories*, 50 pages.
Exhibit dated Aug. 1, 2013 and cited by defendant in Civil Action No. 09-40089-FDS providing the trial transcript in the matter of *Abbott Laboratories, et al.* v. *The Mathilda and Terrance Kennedy Institute*, S.D.N.Y., 90 pages.
Exhibit dated Aug. 1, 2013 and cited by plaintiff in Civil Action No. 09-40089-FDS providing excerpts from the File History of U.S. Appl. No. 12/578,487, 5 pages.
Exhibit dated Aug. 1, 2013 and cited by defendant in Civil Action No. 09-40089-FDS providing the Jun. 24, 2009 trial transcript of the AM session in the matter of *Centocor, et al.* v. *Abbott Laboratories*, E.D. TX., 42 pages.
Exhibit dated Aug. 1, 2013 and cited by defendant in Civil Action No. 09-40089-FDS providing the Sep. 20, 2012 Day 8 trial transcript in the matter of *Abbott* v. *Centocor Ortho Biotech Inc.*, D. MA., 71 pages.

(56) References Cited

OTHER PUBLICATIONS

Exhibit dated Aug. 1, 2013 and cited by plaintiff in Civil Action No. 09-40089-FDS providing Declaration by Jochen Salfeld, dated Jan. 17, 2013, 40 pages.
FDA Package insert for Adalimumab, Sep. 26, 2003, pp. 1-16.
Feldmann, "Anti-TNF-alpha Therapy of Rheumatoid Arthritis: What Have We Learned?" (2001) *Annu. Rev. Immunol.*, 19:163-196.
Li et al., "Cell Culture Processes for Monoclonal Antibody Production," mAbs, 2:5, 466-477, Sep./Oct. 2010.
Figini, "In Vitro assembly of Repertoires of Antibody Chains on the Surface of Phage by Renaturation" (1994) *J. Mol. Biol.*, 239:68-78.
Fishwild et al., "High-avidity human IgG kappa monoclonal antibodies from a novel strain of minilocus transgenic mice" (1996) *Nature Biotechnology*, 14:845-851.
Folk et al., "Carboxypeptidase B, Purification and Characterization of the Porcine Enzyme," J. Biological Chem, 1960, 235:2272-2277.
Fomsgaard, "Auto-antibodies to Tumor Necrosis Factor α in Healthy Humans and Patients with Inflammatory Diseases and Gram-Negative Bacterial Infections" (1989) *Scand. J. Immunol.* 30:219-23.
Foote, J. "Antibody framework residues affecting the conformation of the hypervariable loops" (1992) *J. Mol .Biol.*, 224(2):487-499.
Freitag et al., "Displacement chromatography in biotechnological downstream processing," J. Chromatography, (1995) 691(1):101-112.
Gagnon et al., "A Systematic Approach to the Purification of Monoclonal Antibodies," *LC-GC* 11 (1):26-34 (1993).
Gatto, B. "Biologics targeted at TNF: design, production and challenges", Reumatismo 58(2):94-103, 2006.
Genbank Entry for CHO Cathepsin L., EGW13555, Aug. 25, 2011, pp. 1-2.
Ghaderi, et al., "Implications of the Presence of N-glycolylneuraminic acid in Recombinant Therapeutic Glycoproteins", *Nature Biotechnology*, 28(8):863-868 (2010).
Ghaderi, et al., "Production platforms for biotherapeutic glycoproteins. Occurrence, impact, and challenges of non-human sialylation", *Biotechnology and Genetic Engineering Reviews*, 28:147-176 (2012).
Gonzalez et al. "Purification of Lactic Acid from Fermentation Broths by Ion-Exchange Resins" Ind. Eng. Chem. Res. 45:3243 (2006).
Graf et al., "Ion exchange resins for the purification of monoclonal antibodies from animal cell culture" Bioseparation 4 (1) :7-20 (Feb. 1994). ;4 (1) :7-20 (Feb. 1994).
Gram et al., "In vitro selection and affinity maturation of antibodies from a naive combinatorial immunoglobulin library" (1992) *PNAS*, 89:3576-3580.
Gramer et al., "Glycosidase Activities of the 293 and NS0 Cell Lines, and of an Antibody-Producing Hybridoma Cell Line", *Biotechnology and Bioengineering*, 43:423-428 (1994).
Green et al., "Antigen-specific human monoclonal antibodies from mice engineered with human Ig heavy and light chain YACs" (1994) *Nature Genetics*, 7:13-21.
Griffiths et al., "Isolation of high affinity human antibodies directly from large synthetic repertoires" (1994) *EMBO J.*, 13:3245-3260.
Griffiths, "Human anti-self antibodies with high specificity from phage display libraries" (1993) *The EMBO J.* 12(2):725-34.
Grunberg, J. et al., "High-Yield Production of Recombinant Antibody Fragments in HEK-293 Cells Using Sodium Butyrate", BioTechniques 34(5):968-972, May 2003.
Gu, X. et al: "Improvement of interferon-gamma sialylation in Chinese hamster ovary cell culture by feeding of N-acetylmannosamine",Biotechnology and Bioengineering, Wiley & Sons, Hoboken, NJ, US, vol. 58, No. 6, Jun. 20, 1998, pp. 642-648.
Oh et al., "Effect of N-Acetylcystein on Butyrate-Treated Chinese Hamster Ovary Cells to Improve the Production of Recombinant Human Interferon-β-1a", Biotechnol. Prog. 21(4):1154-1164, 2005.
Harding et al., "Class switching in human immunoglobulin transgenic mice" (1995) *Ann. NY Acad. Sci.*, 764:536-546.
Harlow and Lane, Antibodies A Laboratory Manual, Purification of Antibodies by using a; Deae-matrix (Batch), Storing and Purifying Antibodies; Chapter 8: 302-303 (1988).
Harris, "Processing of C-terminal lysine and arginine residues of proteins isolated from mammalian cell culture" Journal of Chromatography, (1995) 705; 129-134.
Harris, Reed J. et al., "Structural Characterization of a Recombinant CD4-IgG Hybrid Molecule," Eur. J. Biochem. 194:611-620 (1990).
Harrison et al., "Protein N-Glycosylation in the Baculovirus-Insect Cell Expression System and; Engineering of Insect Cells to Produce "Mammalianized" Recombinant Glycoproteins," Advances in; Virus Research, 68:159-191 (2006).
Hawkins, "Selection of Phage Antibodies by Binding Affinity Mimicking Affinity Maturation" (1992) *J. Mol. Biol.*, 226:889-896.
Heidemann, R. et al., "The use of peptones as medium additives for the production of a recombinant therapeutic protein in high density perfusion cultures of mammalian cells", Cytotechnology 32:157-167, 2000.
Helms et al., "Destabilizing loop swaps in the CDRs of an immunoglobulin VL domain," Protein; Science 4:2073-2081 (1995).
Hiatt et al., "Characterization and Applications of Antibodies Produced in Plants", *Intern. Rev. Immunol.*, 10:139-152 (1993).
Hiatt et al., "Production of Antibodies in Transgenic Plants", *Nature*, 342:76-78 (1989).
Hillgren, A. et al., "Protection mechanism of Tween 80 during freeze-thawing of a model protein LDH," *International Journal of Pharmaceutics*, vol. 237:57-69 (2002).
Hokke et al., "Sialylated Carbohydrate Chains of Recombinant Human Glycoproteins Expressed in Chinese Hamster Ovary Cells Contain Traces of $N$-glycolylneuraminic acid", *FEBS*, 275:9-14 (1990).
Holler, "Modulation of Acute Graft-Versus-Host Disease After Allogeneic Bone Marrow Transplantation by Tumor Necrosis Factor-alpha (TNF-alpha) Release in the Course of Pretransplant Conditioning: Role of Conditioning Regimens and Prophylactic Application of a Monoclonal Antibody Neutralizing Human TNF-alpha (MAK 195F)" (1995) *Blood*, 86(3):890-899.
Holt, L. et al., "Domain antibodies: proteins for therapy," Trends in Biotechnology, vol. 21(11):484-490 (2003).
Hoogenboom et al., "By-passing immunisation : Human antibodies from synthetic repertoires of germline $V_H$ gene segments rearranged in vitro" (1992) *J. Mol. Biol.*, 227:381-388.
Hoogenboom, "Converting rodent into human antibodies by guided selection" (1996) *Antibody Engineering*, Oxford University Press, pp. 169-185.
Horvath et al: "Characterization of a Monoclonal Antibody Cell Culture Production Process Using a Quality by; Design Approach", Molecular Biotechnology, vol. 45, No. 3, Jul. 1, 2010, pp. 203-206.
Hossler et al., "Optimal and consistent protein glycosylation in mammalian cell culture", Glycobiology; (2009), 19(9):936-949.
Hossler et al.; "Improvement of mammalian cell culture performance through surfactant enabled concentrated feed media"; Biotechnology Progress; 29(4):1023-1033 (2013).
www.cygnustechnologies.com/product_detail/host-cell-protein-antibodies/anti-cho-h...CYGNUS Technologies, Anti-CHO HCP (Apr. 18, 2012), 1 page.
Huang et al. "Effects of anti-TNF monoclonal antibody infusion in patients with hairy cell leukaemia" (1992) *Br. J. Haematol.*, 81(2):231-234.
Liu et al., "Recovery and purification process development for monoclonal antibody production," MABS (2010) 2(5):480-499.
Humira (adalimumab) label, Revised Sep. 2013, 87 pages.
Humira (adalimumab) prescribing information, Dec. 20, 2002, pp. 1-16.
Huse, "Generation of a large combinatorial library of the immunoglobulin repertoire in phage lambda" (1989) *Science*, 246:1275-81.
ICH Topic Q6B "Specifications:Test Procedures and Acceptance Criteria for Biotechnological/Biological Products," Sep. 1999, pp. 1-17.
International Preliminary Report on Patentability for Application No. PCT/US07/08359, dated Dec. 12, 2011, 5 pages.

(56) References Cited

OTHER PUBLICATIONS

International Preliminary Report on Patentability for Application No. PCT/US2011/060388, dated May 30, 2012, 9 pages.
International Preliminary Report on Patentability for Application No. PCT/US2013/031352 dated Nov. 25, 2014, pp. 1-10.
International Preliminary Report on Patentability for Application No. PCT/US2013/031389, dated Oct. 21, 2014, pp. 1-10.
International Preliminary Report on Patentability for Application No. PCT/US2013/031485, dated Oct. 21, 2014, pp. 1-8.
International Preliminary Report on Patentability for Application No. PCT/US2013/031681, dated Oct. 21, 2014, pp. 1-8.
International Preliminary Report on Patentability for Application No. PCT/US2013/041954, dated Nov. 25, 2014, pp. 1-14.
International Preliminary Report on Patentability for Application No. PCT/US2013/041958, dated Dec. 4, 2014, pp. 1-2.
International Search Report and Written Opinion for Application No. PCT/US2008/085066, dated May 12, 2009, 5 pages.
International Search Report and Written Opinion for Application No. PCT/US2010/033387, dated Aug. 7, 2012, 10 pages.
International Search Report and Written Opinion for Application No. PCT/US2013/031380, dated Feb. 5, 2014, 162 pages.
International Search Report and Written Opinion for Application No. PCT/US2013/041954, dated Dec. 17, 2013, 21 pages.
International Search Report and Written Opinion for Application No. PCT/US2013/041958, dated Dec. 17, 2013, 21 pages.
International Search Report and Written Opinion for Application No. PCT/US2013/065720, dated Dec. 16, 2013, 14 pages.
International Search Report and Written Opinion for Application No. PCT/US2013/065797, dated Nov. 26, 2013, 14 pages.
International Search Report and Written Opinion from PCT/US2013/065749 dated Mar. 18, 2014, 18 pages.
International Search Report and Written Opinion from PCT/US2014/024151 dated Aug. 7, 2014, pp. 1-16.
International Search Report for Application No. PCT/IB03/04502, dated May 26, 2004, 6 pages.
International Search Report for Application No. PCT/US2011/060388 dated May 30, 2012, 6 pages.
International Search Report for Application No. PCT/US2013/031352, Dated Apr. 25, 2013, 6 pages.
International Search Report for Application No. PCT/US2013/031389, Dated Jun. 3, 2013, 4 pages.
International Search Report for Application No. PCT/US2013/031485, Dated Jun. 25, 2013, 4 pages.
International Search Report for Application No. PCT/US2013/031681, Dated Jun. 14, 2013, 6 pages.
International Search Report from PCT/US2014/024256 dated Jul. 30, 2014, pp. 1-15.
Invitation to Pay Additional Fees for International Application No. PCT/US2013/031380, Dated Nov. 28, 2013, 5 pages.
Invitation to Pay Additional Fees for International Application No. PCT/US2013/065749, Dated May 27, 2014, pp. 1-8.
Invitation to Pay Additional Fees for International Application No. PCT/US2014/026606, Dated Jul. 8, 2014, pp. 1-8.
Jakobovits, A., "Production of fully human antibodies by transgenic mice" (1995) *Curr. Op. Biotechnol.*, 6:561-566.
Jayapal, Karthik P., et al., "Recombinant Protein Therapeutics from CHO Cells—20 Years and Counting," CHO Consortium, SBE Special Section, 40-47 (2007).
Jayme et al.; "Media formulation options and manufacturing process controls to safeguard against introduction of animal origin contaminants in animal cell culture"; Cytotechnology; 33:27-36 (2000).
Jespers, "Guiding the Selection of Human Antibodies from Phage Display Repertoires to a Single Epitope of an Antigen" (1994) *Bio/Technology*, 12:899-903.
Johnson et al., "Characterization of cathepsin L secreted by 5f21 insect cells", Archives of Biochemistry and Biophysics (2005), 444:7-14.
Kalyanpur, M., "Downstream Processing in the Biotechnology Industry" Molecular Biotechnology, vol. 22:87-98 (2002).

Karampetsou et al., "TNF-α antagonists beyond approved indications: stories of success and prospects for the future", Q J Med (2010) 103:917-928.
Kaschak et al: "Characterization of the basic charge variants of a human IgGI: Effect of copper concentration in cell culture media", MABS, vol. 3, No. 6, Nov. 1, 2011, pp. 577-583.
Kazuaki, F. et al., "Enhancement of productivity of recombinant α-amidating enzyme by low temperature culture", Cytotechnology 31:85-94, 1999.
Kempeni, "Update on D2E7: a fully human anti-tumour necrosis factor-alpha monoclonal antibody" (2000) *Ann. Rheum. Dis.*, 59(Suppl. I)144-145.
Kempeni, J, "Preliminary results of early clinical trials with the fully human anti-TNFα monoclonal antibody D2E7", Ann. Rheum. Dis., 1999, pp. 170-172, vol. 58, (Suppl. I).
Kempf, C, et al. "Virus inactivation during production of intravenous immunoglobulin." *Transfusion* 1991; vol. 31: p. 423-427.
Khawli et al, "Charge variants in IgGI: Isolation, characterization, in vitro binding properties and pharmacokinetics in rats", MABS, vol. 2, No. 6, Nov. 1, 2010, pp. 613-624.
Kim, NS. et al., "Inhibition of sodium butyrate-induced apoptosis in recombinant Chinese hamster ovary cells by constitutively expressing antisense RNA of caspase-3", Biotechn. & Bioengin. 78(2):217-228, 2002.
Knight et al., "Construction and initial characterization of a mouse-human chimeric anti-TNF antibody" (1993) *Mol. Immunol.*, 30(16):1443-1453.
Kopaciewicz et al., "Retention Model for High-Performance Ion-Exchange Chromatography,"; Journal of Chromatography, 266:3-21 (1983).
Kwon et al., "Production of lactic acid by *Lactobacillus rhamnosus* with vitamin-suppremented soybean hydrolysate", Enzyme Microb Technol. (2000), 26:209-215.
Lerner, "Antibodies without immunization" (1992) *Science*, 258:1313-1314.
Leusch et al., "Failure to demonstrate TNFα-specific autoantibodies in human sera by ELISA and Western blot" (1991) *J. Immunol. Methods*, 139:145-47.
Lewis, "Use of alanine scanning mutagenesis to improve the affinity of an anti gp120 (HIV) antibody" (1994) *J. Cell. Biochem.*, 18D:215.
Li, F. et al., "Current Therapeutic Antibody Production and Process Optimization" BioProcessing Journal, vol. 4(5):23-30 (2005).
Li, Feng, et al., "Cell Culture Processes for Monoclonal Antibody Production," mAbs 2:5, 466-479 (Sep.-Oct. 2010).
Lifely et al., "Glycosylation and Biological Activity of CAMPATH-1H Expressed in Different Cell Lines and Grown Under Different Culture Conditions", *Glycobiology*, 5(8):813-822 (1995).
Logan, John S. "Transgenic Animals: Beyond 'Funny Milk'", *Current Opinion in Biotechnology*, 4:591-595 (1993).
Lonberg et al., "Antigen-specific human antibodies from mice comprising four distinct genetic modifications" (1994) *Nature*, 368:856-859.
Lonberg et al., "Human Antibodies from Transgenic Mice" (1995) *Int. Rev. Immunol.*, 13:65-93.
Low et al., "Mimicking Somatic Hypermutation: Affinity Maturation of Antibodies Displayed on Bacteriophage Using a Bacterial Mutator Strain" (1996) *J. Mol. Biol.*, 260:359-368.
Low, Nigel: thesis extract (1996) *Cambridge University*.
Luo et al., "Understanding of C-terminal lysine variants in antibody production using mammalian cells" Abstract of papers, ACS, Anaheim, CA, US, Mar. 2011, 1 page.
Luo et al: "Probing of C-terminal lysine variation in a recombinant monoclonal antibody production using Chinese hamster ovary cells with chemically defined media", Biotechnology and Bioengineering, vol. 109, No. 9, Apr. 11, 2012, pp. 2306-2315.
Luo, Ying at al.: "Development toward rapid and efficient screening for high performance hydrolysate lots in a recombinant monoclonal antibody manufacturing process.", Biotechnology Progress Jul. 2012, vol. 28, No. 4, Jul. 2012, pp. 1061-1068.
Ma, et al., "Generation and Assembly of Secretory Antibodies in Plants", *Science*, 268:716-719 (1995).

(56) References Cited

OTHER PUBLICATIONS

Maeda, et al., "Analysis of Nonhuman N-Glycans as the Minor Constituents in Recombinant Monoclonal Antibody Pharmaceuticals", *Anal. Chem.*, 84:2373-2379 (2012).
Mahler, et al. Induction and analysis of aggregates in a liquid IgG1-antibody formulation. Eur J Pharm Biopharm. 2005, 59(3):407-17; p. 408; col. 1-2; p. 409; col. 2, "2.2.2 Stirring stress".
Marks et al., "Human antibody fragments specific for human blood group antigens from a phage display library" (1993) *Bio/Technology*, 11:1145-1150.
Marks et al., "Molecular evolution of proteins on filamentous phage. Mimicking the strategy of the immune system" (1992) *J. Biol. Chem.* 267:16007-16010.
Marks, "By-passing immunization: Human antibodies from V-gene libraries displayed on phage" (1991) *J. Mol. Biol.*, 222:581-597.
Marks, "Human Monoclonal Antibodies from V-gene Repertoires Expressed on Bacteriophage." In *Antibody Engineering*, Second Edition, edited by Carl A.K. Borrebaeck (1995), pp. 53-88. New York: Oxford Univ. Press.
Marks, JD., "By-Passing Immunization: Building High Affinity Human Antibodies by Chain Shuffling" (1992) *Biotechnology*, 10:779-783.
Martin, A.C.R. "Accessing the Kabat antibody sequence database by computer" (1996) *Proteins: Structure, Function and Genetics*, 25:130-133.
Martinelle, K. et al., "Effect of different cell culture medium surfactants on cell growth and viability", Cells and Culture, Proceedings of the 20th ESACT Meeting v4 819-822, Jun. 17-20, 2007.
Medynski, "Phage Display: All Dressed Up and Ready to Role" (1994) *Bio/Technology*, 12:1134-1136.
Mendez et al., "Functional transplant of megabase human immunoglobulin loci recapitulates human antibody response in mice" (1997) *Nature Genetics*, 15:146-156.
Meuwly, F. et al., "Conversion of a CHO cell culture process from perfusion to fed-batch technology without altering product quality", J.Biotechn. 123:106-116, 2006.
Miller et al. "Characterization of site-specific glycation during process development of a human therapeutic monoclonal antibody" Journal of Pharmaceutical Sciences, vol. 100, No. 7, Jul. 2011, 2543-2550.
Millipore, "Pellicon 2 Filters and Holders," 2003, pp. 1-8.
Moore, A., et al., "Effects of temperature shift on cell cycle, apoptosis and nucleotide pools in CHO cell batch cultures", Cytotechnology, 23:47-54, 1997.
Möller, Monoclonal antibodies to human tumor necrosis factor α: in vitro and vivo application (1990) *Cytokine*, 2(3):162-69.
Neuberger M. et al., "Mice perform a human repertoire" (1997) *Nature*, 386:25-26.
Ngo et al., "Kosmotropes enhance the yield of antibody purified by affinity chromatography using immobilized bacterial immunoglobulin binding proteins," Journal of Immunoassay & Immunochemistry, (2008) 29(1):105-115.
Nilsson, "Antibody engineering" (1995) *Current Opinion in Structural Biology*, 5:450-456.
Nogal, B., Chhiba, K. and Emery, J. C. (2012), Select host cell proteins coelute with monoclonal antibodies in protein a chromatography. Biotechnol Progress, 28: 454-458.
Noguchi et al., "Failure of Human Immunoresponse to N-Glycolylneuraminic Acid Epitope Contained in Recombinant Human Erythropoietin", *Nephron*, 72:599-603 (1996).
Noguchi et al., "Immunogenicity of N-Glycolylneuraminic Acid-Containing Carbohydrate Chains of Recombinant Human Erythropoietin Expressed in Chinese Hamster Ovary Cells", *J. Biochem.*, 117:59-62 (1995).
Oh, D-K. et al., "Increased erythritol production in fed-batch cultures of Torula sp. by controlling glucose concentration", J. Industrial Microb. & Biotechn. 26(4): 248-252, 2001.
Oh, SKW, et al., "Substantial Overproduction of Antibodies by Applying Osmotic Pressure and Sodium Butyrate", Biotechn. Bioengin. 42(5):601-610, 1993.
Osbourn, "From rodent reagents to human therapeutics using antibody guided selection" (2005) *Methods*, 36(1):61-68.
Patel, T. P. et al.: "Different culture methods lead to differences in glycosylation of a murine IgG monoclonal antibody", Biochemical journal, The Biochemical Society, London, GB, vol. 285, No. 3, Jan. 1, 1992, pp. 839-845.
Perchiacca et al., "Engineering aggregation-resistant antibodies", Annu. Rev. Chem. Biomol. Eng. (2012), 3:263-86.
Pietersz et al., "In vitro and in vivo Antitumor Activity of a Chimeric anti-CD19 Antibody", *Cancer Immunol. Immunother.*, 41:53-60 (1995).
Pink, T. et al.: "Regulation of S-layer protein synthesis of *Bacillus stearothermophilus* PV72 through variation of continuous cultivation conditions", Journal of Biotechnology, Elsevier Science Publishers, Amsterdam, NL, vol. 50, No. 2, Oct. 1, 1996, pp. 189-200.
Potter et al., "Antibody Production in the Baculovirus Expression System", *Intern. Rev. Immunol.*, 10:103-112 (1993).
Poul et al., "Design of Cassette Baculovirus Vectors for the Production of Therapeutic Antibodies in Insect Cells", *Immunotechnology*, 1:189-196 (1995).
Queen, C., "A humanized antibody that binds to the interleukin 2 receptor" (1989) *Proc. Natl. Acad. Sci. USA*, 86(24):10029-10033.
Rader et al. "A phage display approach to rapid antibody humanization: Designed combinatorial V gene libraries" (1998) *Proc Natl Acad Sci USA*, 95:8910-8915.
Raju, TS. "Glycosylation Variations with Expression Systems and Their Impact on Biological Activity of Therapeutic Immunoglobulins", *BioProcess International.*, 44-53 (2003).
Rea, J. C. et al.: "Validation of a pH gradient-based ion-exchange chromatography method for high-resolution monoclonal antibody charge variant separations", Journal of Pharmaceutical and Biomedical Analysis, New York, NY, US, vol. 54, No. 2, Jan. 25, 2011, pp. 317-323.
Reichert JM., et al., "Monoclonal antibody successes in the clinic", Nature Biotech. 23(9):1073-1078, 2005.
Reinhart, "Assessment of the safety and efficacy of the monoclonal anti-tumor necrosis factor antibody-fragment, MAK 195F, in patients with sepsis and septic shock: a multicenter, randomized, placebo-controlled, dose-ranging study" (1996) *Crit. Care Med.*, 24(5):733-742.
Rheinwald JG, et al., "Growth of Cultured Mammalian Cells on Secondary Glucose Sources", Cell, 287-293, 1974.
Ridder et al., "Generation of Rabbit Monoclonal Antibody Fragments from a Combinatorial Phage Display Library and Their Production in Yeast *Pichia pastoris*", *Biotechnology*, 13:255-260 (1995).
Riechmann, "Phage display and selection of a site-directed randomized single-chain antibody Fv fragment for its affinity improvement" (1993) *Biochemistry*, 32(34):8848-8855.
Routier, F. H. et al.: "The glycosylation pattern of a humanized IgGI antibody(D1.3) expressed in CHO cells", Glycoconjugate Journal, Chapman & Hall, GB, vol. 14, No. 2, Jan. 1, 1997, pp. 201-207.
Rube et al., "Ewing's sarcoma and peripheral primitive neuroectodermal tumor cells produce large quantities of bioactive tumor necrosis factor-α (TNF-α) after radiation exposure", Int. J. Radiation Oncology Biol. Phys., (2003), vol. 56, No. 5, pp. 1414-1425.
Rudikoff et al., "Single amino acid substitution altering antigen-binding specificity" (1982) *Proc. Natl. Acad. Sci. USA*, 70:1979-1983.
Sakai et al.; "Use of nonionic surfactants for effective supply of phosphatidic acid in serum-free culture of Chinese hamster ovary cells"; Journal of Bioscience and Bioengineering; 92(3):256-261 (2001).
Salfeld, "Development of a Fully Human Antibody to TNF by Phage Display Technology," IBC Conference, *Antibody Engineering*, San Diego (Dec. 1996), pp. 1-36.
Sandadi, S. et al., "Heuristic Optimization of Antibody Production by Chinese Hamster Ovary Cells", Biotech. Progress, American Institute of Chem. Engineers: 21(5): 1537-1542, 2005.
Sandhu, J. "Protein engineering of antibodies" (1992) *Critical Reviews in Biotechnology*, 12:437-462.

(56) References Cited

OTHER PUBLICATIONS

Santora et al., "Characterization of recombinant human monoclonal tissue necrosis factor-alpha antibody using cation exchange HPLC and capillary isoelectric focusing," Analytical Biochemistry, (1999) 275:98-108.

Santora, "Characterization of Noncovalent Complexes of Recombinant Human Monoclonal Antibody and Antigen Using Cation Exchange, Size Exclusion Chromatography, and BIAcore" (2001) *Analytical Biochemistry*, 299:119-129.

Sato et al, "Stimulation of monoclonal antibody production by human-human hybridoma cells with an elevated concentration of potassium or sodium phosphate in serum-free medium," Cytotechnology 2:63-67, 1989.

Satoh, Mitsuo et al.: "Non-Fucosylated therapeutic antibodies as next-generation therapeutic antibodies", Expert opinion on biological therapy, Ashley, London, GB, vol. 6, No. 11, Nov. 1, 2006, pp. 1161-1173.

Schiestl et al. "Acceptable changes in quality attributes of glycosylated biopharmaceuticals" Nature Biotechnology, 29(4), 310-312 (2011).

Schwieterman, "Immunosuppression in Combination with Monoclonal Antibodies" in Biologic Agents in Autoimmune Disease (Mar. 2-4, 1995).

Senczuk et al. "Hydrophobic interaction chromatography in dual salt system increases protein binding capacity" Biotechnology and Bioengineering, 103(5), 930-935 (2009).

Seresht et al., "The impact of phosphate scarcity on pharmaceutical protein production in *S. cerevisiae*: linking transcriptomic insights to phenotypic responses" Microbial Cell Factories. 2011, 10: 104.

Sheeley et al., "Characterization of Monoclonal Antibody Glycosylation: Comparison of Expression Systems and Identification of Terminal α-Linked Galactose", *Anal. Biochem.*, 247(1):102-110 (1997).

Sheikh et al., "Studies of the digestion of bradykinin, lysyl bradykinin, and kinin-degradation products by carboxypeptidases A, B, and N;". Biochemical Pharmacology. 1986, 35: 1957-1963.

Shen, Amy Y. et al., "Recombinant DNA Technology and Cell Line Development," from "Cell Culture Technology for Pharmaceutical and Cell-Based Therapies," CRC Press, 1995, 15-40.

Shih, "Effects of Anions on the Deamidation of Soy Protein". Journal of Food Science. 1991, 56: 452-454.

Shukla et al., "Host cell protein clearance during protein A chromatography: development of an improved column wash step," Biotechnology Progress, (2008) 24(5):1115-1121.

Shukla et al., "Recent advances in large-scale production of monoclonal antibodies and related proteins," Trends in Biotechnology, (2010) 28(5):253-261.

Sioud et al., "Characterization of naturally occurring autoantibodies against tumour necrosis factor-alpha (TNF-α): in vitro function and precise epitope mapping by phage epitope library" (1994) *Clin. Exp. Immunol.*, 98:520-525.

Sundaram et al., "An innovative approach for the characterization of the isoforms of a monoclonal antibody product," Mabs, 3(6):505-512, 2011.

Kim et al.: "Development of serum-free medium supplemented with hydrolysates for the production of therapeutic antibodies in CHO cell cultures using design of experiments", Applied Microbiology and Biotechnology, Springer, Berlin, DE, vol. 83, No. 4, Mar. 6, 2009, pp. 639-648.

Sung, Y.H. et al., "Yeast hydrolysate as a low-cost additive to serum-free medium for the production of human thrombpoietin in suspension cultures of Chinese hamster ovary cells", *Applied Microbilolgy and Biotechnology* 63:5, 527-536, 2004.

Takagi, M. et al., "The effect of osmolarity on metabolism and morphology in adhesion and suspension chinese hamster ovary cells producing tissue plasminogen activator", Cytochnology 32:171-179, 2000.

Tamura et al., "Structural correlates of an anticarcinoma antibody: identification of specificity-determining residues (SDRs) and development of a minimally immunogenic antibody variant by retention of SDFs only," *J. Immun.* (2000) 164:1432-1441.

Tan et al., "Expression and purification of a secreted functional mouse/human chimaeric antibody against bacterial endotoxin in baculovirus-infected insect cells", Biotechnol. Appl. Biochem. (1999), 30:59-64.

Taylor et al.,"Human immunoglobulin transgenes undergo rearrangement, somatic mutation and class switching in mice that lack endogenous IgM" (1994) *Int. Immunol.*, 6:579-591.

Teichmann, S. Declaration dated Dec. 17, 2010 from opposition proceedings in EP 0929578, 6 pages.

Tharmalingam et al.; "Pluronic Enhances the Robustness and Reduces the Cell Attachment of Mammalian Cells"; Molecular Biotechnology; 39(2):167-177 (2008).

The Kennedy Institute of Rheumatology, 1995 Annual Scientific Report, "Anti-TNF trials and studies of mechanisms of action", 4 pages.

The MW Calculator available at the Sequence Manipulation Suite (see bioinformatics.org/sms2/index.html), downloaded Feb. 25, 2014, 2 pages.

The pI Calculator available at the Sequence Manipulation Suite (see <bioinformatics.org/sms2/index.html>), downloaded Feb. 25, 2014, p. 1).

The Statement on a Nonproprietary Name Adopted by the USAN Council for Adalimumab, p. 1, downloaded on May 19, 2011 from www.ama-assn.org/resources/doc/usan/adalimumab.doc. 1 page.

Thompson, "Affinity maturation of a high-affinity human monoclonal antibody against the third hypervariable loop of human immunodeficiency virus: use of phage display to improve affinity and broaden strain reactivity" (1996) *J. Mol. Biol.*, 256(1):77-88.

Thorp, "Tumour Necrosis Factor Induction of ELAM-1 and ICAM-1 on Human Umbilical Vein Endothelial Cells—Analysis of Tumour Necrosis Factor Receptor Interaction" (1992) *Cytokine*, 4(4): 313-319.

Tomiya et al., "Comparing N-glycan processing in mammalian cell lines to native and engineered; lepidopteran insect cell lines," Glycoconjuqate Journal 21:343-360 (2004).

Tomlinson, "The repertoire of human germline VH sequences reveals about fifty groups of VH segments with different hypervariable loops" (1992) *J. Mol. Biol.*, 227:776-98.

Tomlinson, "The structural repertoire of the human Vk domain" (1995) *The EMBO J.*, 14(18):4628-38.

Tracey, "Tumor necrosis factor: A pleiotropic cytokine and therapeutic target" (1994) *Annu. Rev. Med.*, 45:491-503.

Tsuchiyama et al., "Comparison of anti-TNF alpha autoantibodies in plasma and from EBV transformed lymphocytes of autoimmune and normal individuals" (1995) *Hum. Antibod. Hybridomas*, 6(2):73-76.

Vallee B et al. "The role of zinc in carboxypeptidase" The Journal of Biological Chemistry, (1960) 235, 1; 64-69.

Valliere-Douglass et al., "Glutamine-linked and Non-consensus Asparagine-linked Oligosaccharides Present in Human Recombinant Antibodies Define Novel Protein Glycosylation Motifs", *J. Biol. Chem.*, 285:16012-16022 (2010).

Van Der Poll, "Effect of postponed treatment with an anti-tumour necrosis factor (TNF) F(ab')2 fragment on endotoxin-induced cytokine and neutrophil responses in chimpanzees" (1995) *Clin. Exp. Immunol.*, 100:21-25.

Van Lent PL, et al. "The impact of protein size and charge on its retention in articular cartilage" J Rheumatol. Aug. 1987;14(4):798-805.

Varasteh et al. Optimization of Anti-Rh D Immunoglobulin Stability in the Lyphiliization Process. Iranian Journal of Basic Medical Sciences, Spring 2008, vol. 11, No. 1. pp. 55-61.

Vaughan, "Human antibodies by design" (1998) *Nature Biotechnology*, 16:535-539.

Wagner et al., "Antibodies generated from human immunoglobulin miniloci in transgenic mice" (1994) *Nucl. Acids Res.* 22:1389-1393.

Wagner et al., "The diversity of antigen-specific monoclonal antibodies from transgenic mice bearing human immunoglobulin gene miniloci" (1994) *Eur. J. Immunol.*, 24:2672-2681.

Ward, "Binding activities of a repertoire of single immunoglobulin variable domains secreted from *Escherichia coli*" (1989) *Nature*, 341:544-546.

Wedemayer et al., "Structural insights into the evolution of an antibody combining site" (1997) *Science*, 276:1665-1669.

(56) References Cited

OTHER PUBLICATIONS

Wiendl et al., "Therapeutic Approaches in Multiple Sclerosis. Lessons from failed and interrupted treatment trials", BioDrugs. (2002), 16(3):183-200.
Williams et al., "Kinetic analysis by stopped-flow radiationless energy transfer studies: effect of anions on the activity of carboxypeptidase A". Biochemistry. 1986, 25, 94-100.
Winter, "Humanized antibodies" (1993) *Immunol. Today*, 14(6):243-246.
Winter, "Making antibodies by phage display technology" (1994) *Annu. Rev. Immunol.*, 12:433-455.
Wolff et al., "The Kinetics of Carboxypeptidase B Activity," J. Biological Chem, 1962, 237:3094-3099.
Wong N.S.C. et al: "An investigation of intracellular glycosylation activities in CHO cells: Effects of nucleotide sugar precursor feeding" Biotechnology and Bioengineering, vol. 187, No. 2, Oct. 1, 2010, pp. 321-336.
Worthington Biochemical Corporation, porcine pancreas carboxypeptidase B, one page, Feb. 25, 2012.
Wurm, FM, "Production of recombinant protein therapeutics in cultivated mammalian cells", Nature Biotechnology 22(11):1393-1398, 2004.
Yigzaw et al., "Exploitation of the adsorptive properties of depth filters for host cell protein removal during monoclonal antibody purification," Biotechnology Progress, (2006) 22(1):288-296.
Yumioka et al., "Screening of effective column rinse solvent for Protein-A chromatography," Protein Expression and Purification, (2010) 70(2): 218-223.
Zatarain-Rios E and Mannik M, "Charge-charge interactions between articular cartilage and cationic antibodies, antigens, and immune complexes," Arthritis Rheum. Nov. 1987;30(11):1265-73.
Zhang et al., "Isolation and characterization of charge variants using cation exchange displacement chromatography," 1218(31): 5079-5086, 2011.
Zou et al., "Dominant expression of a 1.3 Mb human Ig kappa locus replacing mouse light chain production" (1996) *FASEB J.*, 10:1227-1232.
Ahmed, M. U.et al.; N-(Carboxyethyl)lysine, a product of the chemical modification of proteins by methylglyoxal, increases with age in human lens proteins; Biochem. J. 1997, 324, 565-570.
Ahmed, N. & Thornalley, P. J.; Peptide Mapping of Human Serum Albumin Modified Minimally by Methylglyoxal in Vitro and in Vivo; Ann. N.Y. Acad. Sci. 2005, 1043,260-266.
Ahmed, N. et al.; Peptide Mapping Identifies Hotspot Site of Modification in Human Serum Albumin by Methylglyoxal Involved in Ligand Binding and Esterase Activity; J. Biol. Chem. 2005, 280, 5724-5732.
Ahmed, N.; Thornalley, P. J.; Advanced glycation endproducts: what is their relevance to diabetic complications?; Diabetes, Obes. Metab. 2007, 9, 233-245.
Alfaro, J. F.; Chemo-Enzymatic Detection of Protein Isoaspartate Using Protein Isoaspartate Methyltransferase and Hydrazine Trapping; Anal. Chem. 2008, 80, 3882-3889.
Alfaro, J. F.; Synthesis of LuxS Inhibitors Targeting Bacterial Cell-Cell Communication; Org. Lett. 2004, 6, 3043-3046.
Awdeh, Z.L., A.R. Williamson, and B.A. Askonas, One cell—one immunoglobulin. Origin of limited heterogeneity of myeloma proteins. Biochem J, 1970. 116(2): p. 241-8.
Bendtzen, K. et al. "Auto-antibodies to IL-1α and TNFα in Normal Individuals and in Infectious and Immunoinflammatory Disorders" *The Physiological and Pathological Effects of Cytokines*, 447-52 (1990).
Biastoff, S.; et al.; Colorimetric Activity Measurement of a Recombinant Putrescine N-Methyltransferase from *Datura stramonium*; Planta Med. 2006, 72, 1136.
Chang, T. & Wu, L., Methylglyoxal, oxidative stress, and hypertension, Can. J. Physiol.Pharmacol. 84: 1229-1238 (2006).
Chaplen, F.W.R., et al., Effect of endogenous methylgiyoxal on Chinese hamster ovary cells grown in culture Cytotechnology 1996, vol. 22, Issue 1-3, Abstract and references, 6 pages.
Chaplen, F.W.R., Incidence and potentiai implications of the toxic metabolite methylglyoxal in cell culture: A review, C\l1otechnoloqy 26: 173-183, 1998.
Chaplen, FWR; A dissertation entitled Analysis of Methylglyoxal Metabolism in Mammalian Cell Culture; Univ. of Wisconsin—Madison 1996, 218 pages.
Cheijus, D. at al.; Identification and Characterization of Deamidation Sites in the Conserved Regions of Human Immunoglobulin Gamma Antibodies, Anal. Chem. 2005, 77,6004-6011.
Chumsae, C., at al., Comparison of methionine oxidation in thermal stability and chemically stressed samples of a fully human monoclonal antibody. Journal of Chromatography B, 2007. 850(1-2): p. 285-294.
Chumsae, C., Gaza-Bulseco, G., & Liu, H., Identification and localization of unpaired cysteine residues in monoclonal antibodies by fluorescence labeling and mass spectrometry. Anal Chem, 2009.81(15): p. 6449-57.
Cordoba, A.J., et al., Non-enzymatic hinge region fragmentation of antibodies in solution. Journal of Chromatography B, 2005. 818(2): p. 115-121.
Dai, S.; An Integrated Proteomic Analysis of Major Isoaspartyl-Containing Proteins in the Urine of Wild Type and Protein LIsoaspartate O-Methyltransferase-Deficient Mice; Anal. Chem. 2013, 85, 2423-2430.
Dobo, A. & Kaltashov, I. A.; Detection of Multiple Protein Conformational Ensembles in Solution via Deconvolution of Charge-State Distributions in ESI MS; Anal. Chem. 2001,73, 4763-4773.
Emery, P. "Adalimumab therapy: Clinical findings and implications for integration into clinical guidelines for rheumatoid arthritis." *Drugs of Today*, 41(3): p. 155-153. (2005).
European Medicines Agency (EMA Europe), "2004 Report on Scientific Discussion for the Approval of Humira™ (adalimumab)," Last accessed Nov. 12, 2014 at www.ema.europa.eu/docs/en_GB/document_library/EPAR_Scientific_Discussion/human/000481/WC500050867.pdf; 25 pages.
Gauthier, M. A.& Klok, H.-A. Arginine-Specific Modification of Proteins with Polyethylene Glycol Biomacromolecules; 2011, 12, 482-493.
Gaza-Bulseco, G., et al., Characterization of the glycosylation state of a recombinant monoclonal antibody using weak cation exchange chromatography and mass spectrometry. J Chromatogr B Analyt Technol Biomed Life Sci, 2008. 862(1-2): p. 155-60. Epub Dec. 8, 2007.
Goswami et al., "Developments and Challenges for mAb-Based Therapeutics," *Antibodies*, 2:452-500, 2013.
Harding et al., "Class switching in human immunoglobulin transgenic mice" (1995) *Ann. NY Acad. Sci.*, 764:536-547.
Harris, R.J., et al., Identification of multiple sources of charge heterogeneity in a recombinant antibody. Journal of Chromatography B: Biomedical Sciences and Applications, 2001. 752(2): p. 233-245.
Hipkiss, A.; Can the beneficial effects of methionine restriction in rats be explained in part by decreased methylglyoxal generation resulting from suppressed carbohydrate metabolism?; Biogerontology 2012, 13, 633-636.
Huang, L., et al., In Vivo Deamidation Characterization of Monoclonal Antibody by LC/MS/MS. Analytical Chemistry, 2005. 77(5): p. 1432-1439.
International Search Report for Application No. PCT/US2014/026606, Dated Dec. 8, 2014, 8 pages.
International Search Report for Application No. PCT/US2014/026636, Dated Jul. 29, 2014, 5 pages.
Jack, M.; Wright, D.; The Role of Advanced Glycation Endproducts and Glyoxalase I in Diabetic Peripheral Sensory Neuropathy; Transl. Res. 2012, 159, 355-365.
Jakubowski, H., Protein N-homocysteinylation: implications for atherosclerosis. Biomedicine & Pharmacotherapy, 2001. 55(8): p. 443-447.
Jefferis, R., Glycosylation of Recombinant Antibody Therapeutics. Biotechnology Progress, 2005.21(1): p. 11-16.
Johnson, K.A., et al., Cation exchange HPLC and mass spectrometry reveal C-terminal amidation of an IqG1 heavy chain. Analytical Biochemistry, 2007. 360(1): p. 75-83.

(56) References Cited

OTHER PUBLICATIONS

Kanda, et al.: "Comparison of biological activity among nonfucosylated therapeutic IgG1 antibodies with three different N-linked Fc oligosaccharides: the high-mannose, hybrid, and complex types", Glycobiology, Oxford University Press, US, vol. 17, No. 1, Sep. 2006, pp. 104-118.
Kingkeohoi, S. & Chaplen, F.W.R., Analysis of methylglyoxal metabolism in CHO cells grown in culture, Cytotechnology (2005) 48:1-13.
Leusch, "Failure to demonstrate TNFα-specific autoantibodies in human sera by ELISA and Western blot" (1991) J. Immunol. Methods, 139:145-47.
Liu, H., et al., Heterogeneity of monoclonal antibodies. Journal of Pharmaceutical Sciences, 2008. 97(7): p. 2426-2447.
Liu, H., Gaza-Bulseco, G., & Lundell, E., Assessment of antibody fragmentation by reversed-phase liquid chromatography and mass spectrometry. J Chromatogr B Analyt Technol Biomed Life Sci, 2008. 876(1): p. 13-23. Epub Oct. 15, 2008.
Liu, M, et al.; Discovery of Undefined Protein Cross-Linking Chemistry: A Comprehensive Methodology Utilizing $^{18}$O-Labeling and Mass Spectrometry; Anal. Chem. 2013, 5900-5908.
Liu, M.et al.; Protein Isoaspartate Methyltransferase-Mediated $^{18}$O-Labeling of Isoaspartic Acid for Mass Spectrometry Analysis; Anal. Chem. 2011, 84, 1056-1062.
Lo, T.W. et al., Binding and modification of proteins by methylglyoxal under physiological conditions. A kinetic and mechanistic study with N alpha-acetylarginine, N alpha-acetylcysteine, and N alpha-acetyllysine, and bovine serum albumin, Dec. 23, 1994, The Journal of Biological Chemistry, 269, 32299-32305.
Manning, M., et al., Stability of Protein Pharmaceuticals: An Update. Pharmaceutical Research, 2010.27(4): p. 544-575.
Matthews, R. G.; et al.; Cobalamin-Dependent and Cobalamin-Independent Methionine Synthases: Are There Two Solutions to the Same Chemical Problem?; Helv. Chim. Acta 2003, 86, 3939-3954.
Mizuochi, T., et al., Structural and numerical variations of the carbohydrate moiety of immunoglobulin G. J Immunol, 1982. 129(5): p. 2016-20.
Moorhouse, K.G., et al., Validation of an HPLC method for the analysis of the charge heterogeneity of the recombinant monoclonal antibody IDEC-C2B8 after papain digestion. Journal of Pharmaceutical and Biomedical Analysis, 1997. 16(4): p. 593-603.
Mostafa, A et al.; Plasma protein advanced glycation end products, carboxymethyl cysteine, and carboxyethyl cysteine, are elevated and related to nephropathy in patients with diabetes Mol. Cell. Biochem. 2007, 302, 35-42.
Ni, W.; Analysis of Isoaspartic Acid by Selective Proteolysis with Asp-N and Electron Transfer Dissociation Mass Spectrometry; Anal. Chem. 2010, 82,7485-7491.
Ouellette, D.; Studies in serum support rapid formation of disulfide bond between unpaired cysteine residues in the VH domain of an immunoglobulin G1 molecule: Anal. Biochem. 2010, 397, 37.
Oya, T. et al. Methylglyoxal Modification of Protein: Chemical and Immunochemical Characterization of Methylglyoxal-Arginine Adducts. J. Biol Chem. Jun. 25, 1999; vol. 274, No. 26, pp. 18492-19502.
Pacis, et al.: "Effects of cell culture conditions on antibody N-linked glycosylation—what affect high mannose 5 glycoform", Biotechnology and Bioengineering vol. 108, No. Oct. 10, 2011, pp. 2348-2358.
Paoli, T. et al., A Study of D-Lactate and Extracellular Methylglyoxal Production in Lactate ReUtilizing CHO Cultures, Biotechnology and Bioengineering, vol. 107, No. 1, Sep. 1, 2010, pp. 182-189.
Parekh, R.B., et al., Association of rheumatoid arthritis and primary osteoarthritis with changes in the glycosylation pattern of total serum IgG. Nature, 1985. 316(6027): p. 452-7.
PCT/US2013/069702 International Search Report & Written Opinion mailed Jan. 31, 2014, 13 pages.
Perkins, M.; et. al. Determination of the Origin of Charge Heterogeneity in a Murine Monoclonal Antibody; M. Pharm. Res. 2000, 17, 1110-1117.
Quan, C., et al., A study in glycation of a therapeutic recombinant humanized monoclonal antibody: Where it is, how it got there, and how it affects charge-based behavior. Analytical Biochemistry, 2008. 373(2): p. 179-191.
Rabbani, N.; Thornalley, P. J.; Glyoxalase in diabetes, obesity and related disorders; Semin. Cell Dev. Biol. 2011, 22, 309-317.
Ren, D., et al., Reversed-phase liquid chromatography-mass spectrometry of site-specific chemical modifications in intact immunoglobulin molecules and their fragments. Journal of Chromatography A, 2008. 1179(2): p. 198-204.
Roy, B.M., et al., Toxic concentrations of exogenously supplied methylglyoxal in hybridoma cell culture, Cytotechnology (2004) 46:97-107.
Saxena, R. K. et al.; Microbial production and applications of 1,2-propanediol; Indian J. Microbiol. 2010,50,2-11.
The Kennedy Institute of Rheumatology, 1995 Annual Scientific Report, "Anti-TNF trials and studies of mechanisms of action".
Van Herreweghe, et al.; Tumor necrosis factor-induced modulation of glyoxalase I activities through phosphorylation by PKA results in cell death and is accompanied by the formation of a specific methylglyoxal-derived AGE; Proc. Natl. Acad. Sci. 2002, 99, 949-954.
Vasilli, P., Annu. Rev. Immunol. 10:411-452 (1992); and Tracey, K. J. and Cerami, A. Annu. Rev. Med. 45:491-503 (1994).
Vlasak, J. & Ionescu, R., Heterogeneity of Monoclonal Antibodies Revealed by Charge-Sensitive Methods. Current Pharmaceutical Biotechnology, 2008. 9(6): p. 468-481.
Walsh, et al.: "Post-translational modifications in the context of therapeutic proteins", Nature Biotechnology, vol. 24, No. 10, Oct. 2006, pp. 1241-1252.
Wang, Z.; et al. Desulfurization of Cysteine-Containing Peptides Resulting from Sample Preparation for Protein Characterization by MS; Rapid Commun. Mass Spectrom. 2010, 24, 267-275.
Watt, S.; et al.; Effect of Protein Stabilization on Charge State Distribution in Positive- and Negative-Ion Electrospray Ionization Mass Spectra; J. Am. Soc. Mass. Spectrom. 2007, 18, 1605-1611.
Williams, A. et al., Ion-Exchange Chromatography, Oct. 1998, Supplement 44, pp. 10-10-1-10-10-30.
Xiang, T., Chumsae, C. & Liu, H., Localization and Quantitation of Free Sulfhydryl in Recombinant Monoclonal Antibodies by Differential Labeling with 12C and 13C Iodoacetic Acid and LC-MS Analysis. Analytical Chemistry, 2009. 81(19): p. 8101-8108.
Yuk, I.H. et al., Controlling Glycation of Recombinant Antibody in Fed Batch Cell Cultures, Nov. 2011, Biotechnology and Bioengineering, vol. 108, No. 11 pp. 2600-2610.
Zang, T.; et al.; Chemical Methods for the Detection of Protein N-Homocysteinylation via Selective Reactions with Aldehydes; Anal. Chem. 2009, 81, 9065-9071.
Zhang, B., et al., Unveiling a Glycation Hot Spot in a Recombinant Humanized Monoclonal Antibody. Analytical Chemistry, 2008. 80(7): p. 2379-2390.
Zhang, T.; Identification and Characterization of Buried Unpaired Cysteines in a Recombinant Monoclonal IgG1 Antibody; Anal. Chem. 2012, 84, 7112-7123.
Zhang, W. and Czupryn, M.J., Free Sulfhydryl in Recombinant Monoclonal Antibodies. Biotechnology Progress, 2002. 18(3): p. 509-513.
Zhao, G.; Chemical Synthesis of S-Ribosyl-L-homocysteine and Activity Assay as a LuxS Substrate; Bioorg. Med. Chem. Lett. 2003,13,3897-3900.
Zhou, Z. et al.; An Antibody-Catalyzed Allylic Sulfoxide-Sulfenate Rearrangement; J. Org. Chem. 1999,64,8334-8341.
Zhou, Z. S. et al. An Antibody-Catalyzed Selenoxide Elimination; J. Am. Chem. Soc. 1997, 119, 3623-3624.
Hills et al., Biotech. and Bioeng., vol. 75(2), pp. 230-251.†
Fleisher, J. Histochem Cytochem, vol. 13, pp. 1033-1040 (1983).†
Crowell et al., Biotech. and Bioeng., vol. 96, pp. 538-549.†
Gramer et al., Biotech. and Bioeng., vol. 108, pp. 1591-1902 (Pub online Feb. 15, 2011).†

* cited by examiner

| Manganese (μM) | Galactose (mM) | % NGA2F+NGA2F-GlcNac | % NA1F+NA2F | Δ (NGA2F+NGA2F-GlcNac) % | | | Δ (NA1F+NA2F) (%) | | |
|---|---|---|---|---|---|---|---|---|---|
| | | | | Galactose Only | Manganese Only | Manganese and Galactose | Galactose Only | Manganese Only | Manganese and Galactose |
| 0 | 0 | 90.0 | 4.7 | | | | | | |
| 0 | 10 | 86.5 | 8.4 | -3.5 | | | 3.8 | | |
| 0 | 20 | 87.4 | 7.4 | -2.6 | | | 2.8 | | |
| 0 | 40 | 84.4 | 11.2 | -5.5 | | | 6.5 | | |
| 0 | 100 | 82.6 | 11.8 | -7.3 | | | 7.2 | | |
| 40 | 0 | 84.1 | 12.7 | | -5.8 | | | 8.0 | |
| 80 | 0 | 82.0 | 13.6 | | -8.0 | | | 9.0 | |
| 100 | 0 | 81.2 | 12.8 | | -8.8 | | | 8.2 | |
| 40 | 10 | 79.2 | 17.4 | | | -10.7 | | | 12.7 |
| 40 | 20 | 76.4 | 20.2 | | | -13.5 | | | 15.5 |
| 40 | 40 | 71.9 | 24.5 | | | -18.0 | | | 19.9 |
| 40 | 100 | 69.3 | 26.3 | | | -20.7 | | | 21.7 |
| 60 | 20 | 73.5 | 22.8 | | | -16.5 | | | 18.1 |
| 60 | 40 | 72.3 | 23.9 | | | -17.6 | | | 19.3 |
| 60 | 100 | 68.2 | 27.8 | | | -21.8 | | | 23.1 |
| 80 | 20 | 74.0 | 20.8 | | | -15.9 | | | 16.1 |
| 80 | 40 | 69.1 | 25.5 | | | -20.8 | | | 20.9 |
| 80 | 100 | 67.7 | 26.5 | | | -22.2 | | | 21.9 |
| 100 | 20 | 73.4 | 19.6 | | | -16.5 | | | 15.0 |
| 100 | 40 | 65.6 | 22.1 | | | -24.4 | | | 17.5 |
| 100 | 100 | 64.4 | 24.8 | | | -25.6 | | | 20.1 |

FIG. 5

| Manganese (μM) | Galactose (mM) | % NGA2F+NGA2F -GlcNac | % NA1F+NA2F | Δ (NGA2F+NGA2F-GlcNac) % | | | Δ (NA1F+NA2F) (%) | | |
|---|---|---|---|---|---|---|---|---|---|
| | | | | Galactose Only | Manganese Only | Manganese and Galactose | Galactose Only | Manganese Only | Manganese and Galactose |
| 0 | 0 | 76.2 | 20.5 | | | | | | |
| 10 | 0 | 74.4 | 22.9 | | -1.9 | | | 2.4 | |
| 20 | 0 | 72.6 | 24.0 | | -3.6 | | | 3.5 | |
| 40 | 0 | 71.4 | 23.3 | | -4.9 | | | 2.8 | |
| 0 | 10 | 71.5 | 25.2 | -4.7 | | | 4.7 | | |
| 0 | 20 | 69.3 | 27.5 | -7.0 | | | 7.0 | | |
| 0 | 40 | 70.4 | 26.4 | -5.9 | | | 5.9 | | |
| 10 | 10 | 69.5 | 27.8 | | | -6.8 | | | 7.3 |
| 20 | 20 | 67.2 | 29.9 | | | -9.1 | | | 9.4 |
| 40 | 40 | 64.4 | 31.1 | | | -11.9 | | | 10.6 |

FIG. 9

| Manganese (μM) | Galactose (mM) | % NGA2F+NGA2F -GlcNac | % NA1F+NA2F | Δ (NGA2F+NGA2F-GlcNac) % | | | Δ (NA1F+NA2F) (%) | | |
|---|---|---|---|---|---|---|---|---|---|
| | | | | Galactose Only | Manganese Only | Manganese and Galactose | Galactose Only | Manganese Only | Manganese and Galactose |
| 0 | 0 | 75.5 | 17.5 | | | | | | |
| 0 | 10 | 73.2 | 20.3 | -2.3 | | | 2.8 | | |
| 0 | 20 | 72.7 | 20.6 | -2.9 | | | 3.2 | | |
| 0 | 40 | 71.9 | 21.4 | -3.6 | | | 3.9 | | |
| 10 | 0 | 75.0 | 18.2 | | -0.5 | | | 0.7 | |
| 10 | 10 | 73.2 | 19.2 | | | -2.3 | | | 1.7 |
| 10 | 20 | 72.3 | 20.0 | | | -3.2 | | | 2.5 |
| 10 | 40 | 71.4 | 20.8 | | | -4.2 | | | 3.4 |
| 20 | 0 | 74.9 | 17.1 | | -0.7 | | | -0.4 | |
| 20 | 10 | 74.3 | 18.4 | | | -1.3 | | | 0.9 |
| 20 | 20 | 72.1 | 20.4 | | | -3.5 | | | 2.9 |
| 20 | 40 | 70.7 | 21.6 | | | -4.8 | | | 4.1 |
| 40 | 0 | 74.6 | 16.6 | | -0.9 | | | -0.9 | |
| 40 | 10 | 72.5 | 19.0 | | | -3.1 | | | 1.5 |
| 40 | 20 | 72.0 | 19.8 | | | -3.6 | | | 2.4 |
| 40 | 40 | 70.8 | 20.8 | | | -4.7 | | | 3.3 |

FIG. 12

| Manganese (μM) | Galactose (mM) | % NGA2F+NGA2F-GlcNac | % NA1F+NA2F | Δ (NGA2F+NGA2F-GlcNac) % |||  Δ (NA1F+NA2F) (%) |||
|---|---|---|---|---|---|---|---|---|---|
| | | | | Galactose Only | Manganese Only | Manganese and Galactose | Galactose Only | Manganese Only | Manganese and Galactose |
| 0 | 0 | 91.0 | 3.3 | | | | | | |
| 0 | 10 | 85.3 | 10.1 | -5.7 | | | 6.8 | | |
| 0 | 20 | 82.1 | 13.3 | -8.9 | | | 10.0 | | |
| 10 | 0 | 72.8 | 24.0 | | -18.3 | | | 20.7 | |
| 20 | 0 | 68.6 | 26.5 | | -22.4 | | | 23.2 | |
| 10 | 10 | 67.4 | 28.2 | | | -23.6 | | | 24.9 |
| 20 | 20 | 59.0 | 36.9 | | | -32.0 | | | 33.6 |
| 40 | 20 | 55.8 | 40.1 | | | -35.3 | | | 36.7 |

FIG. 15

| Manganese (μM) | Galactose (mM) | % NGA2F+NGA2F-GlcNac | % NA1F+NA2F | Δ (NGA2F+NGA2F-GlcNac) % Change ||| Δ (NA1F+NA2F) % Change |||
|---|---|---|---|---|---|---|---|---|---|
| | | | | Galactose Only | Manganese Only | Manganese and Galactose | Galactose Only | Manganese Only | Manganese and Galactose |
| 0 | 0 | 89 | 6 | | | | | | |
| 0.1 | 0 | 82 | 13 | | −7.3 | | | 7.8 | |
| 0.2 | 0 | 75 | 21 | | −14.8 | | | 15.6 | |
| 0.5 | 0 | 65 | 30 | | −24.5 | | | 25.3 | |
| 1.0 | 0 | 63 | 33 | | −26.2 | | | 27.7 | |
| 0 | 30 | 84 | 8 | −4.2 | | | 3.1 | | |
| 0.2 | 30 | 65 | 28 | | | −24.6 | | | 23.6 |
| 0.5 | 30 | 56 | 38 | | | −33.6 | | | 34.1 |

FIG. 18

| Manganese (μM) | Galactose (mM) | % NGA2F+NGA2F-GlcNac | % NA1F+NA2F | Δ (NGA2F+NGA2F-GlcNac) % | | | Δ (NA1F+NA2F) (%) | | |
|---|---|---|---|---|---|---|---|---|---|
| | | | | Galactose Only | Manganese Only | Manganese and Galactose | Galactose Only | Manganese Only | Manganese and Galactose |
| 0 | 0 | 86.3 | 8.0 | | | | | | |
| 0 | 0 | 86.8 | 7.2 | | | | | | |
| 0 | 1 | 86.1 | 8.8 | -0.3 | | | 0.8 | | |
| 0 | 4 | 84.5 | 10.6 | -1.8 | | | 2.6 | | |
| 0 | 5 | 83.6 | 11.0 | -3.2 | | | 3.8 | | |
| 0 | 10 | 72.9 | 22.6 | -13.9 | | | 15.4 | | |
| 0.2 | 0 | 74.0 | 22.1 | | -12.3 | | | 14.1 | |
| 0.5 | 0 | 68.2 | 28.3 | | -18.1 | | | 20.3 | |
| 0.2 | 1 | 71.7 | 24.6 | | | -14.6 | | | 16.6 |
| 0.5 | 1 | 65.6 | 30.9 | | | -20.7 | | | 22.9 |
| 0.2 | 4 | 67.7 | 28.0 | | | -18.7 | | | 20.0 |
| 0.5 | 4 | 60.3 | 36.0 | | | -26.0 | | | 28.0 |

FIG. 21

| Manganese (μM) | Galactose (mM) | % NGA2F+NGA2F -GlcNac | % NA1F+NA2F | Δ (NGA2F+NGA2F-GlcNac) % | | | Δ (NA1F+NA2F) (%) | | |
|---|---|---|---|---|---|---|---|---|---|
| | | | | Galactose Only | Manganese Only | Manganese and Galactose | Galactose Only | Manganese Only | Manganese and Galactose |
| 0 | 0 | 80.2 | 13.6 | | | | | | |
| 10 | 0 | 54.2 | 40.8 | | −26.0 | | | 27.3 | |
| 20 | 0 | 55.3 | 39.3 | | −24.9 | | | 25.7 | |
| 40 | 0 | 60.0 | 35.4 | | −20.2 | | | 21.8 | |
| 0 | 10 | 77.7 | 16.4 | −2.5 | | | 2.9 | | |
| 0 | 20 | 76.4 | 17.6 | −3.8 | | | 4.1 | | |
| 0 | 40 | 68.3 | 26.7 | −11.9 | | | 13.1 | | |
| 10 | 10 | 53.1 | 41.1 | | | −27.1 | | | 27.6 |
| 20 | 20 | 48.7 | 43.9 | | | −31.5 | | | 30.3 |
| 40 | 40 | 53.5 | 41.1 | | | −26.7 | | | 27.6 |

FIG. 24

| Manganese (μM) | Galactose (mM) | % NGA2F+NGA2F-GlcNac | % NA1F+NA2F | Δ (NGA2F+NGA2F-GlcNac) % Change | | | Δ (NA1F+NA2F) % Change | | |
|---|---|---|---|---|---|---|---|---|---|
| | | | | Galactose Only | Manganese Only | Manganese and Galactose | Galactose Only | Manganese Only | Manganese and Galactose |
| 0 | 0 | 86.3 | 8.9 | | | | | | |
| 25 | 0 | 76.3 | 18.0 | | −10.0 | | | 9.1 | |
| 50 | 0 | 68.2 | 25.5 | | −18.1 | | | 16.6 | |
| 75 | 0 | 71.6 | 21.6 | | −14.7 | | | 12.7 | |
| 0 | 15 | 79.4 | 15.0 | −6.9 | | | 6.1 | | |
| 0 | 30 | 74.2 | 19.8 | −12.1 | | | 10.9 | | |
| 0 | 60 | 74.9 | 19.8 | −11.4 | | | 10.9 | | |
| 25 | 15 | 64.3 | 29.4 | | | −22.0 | | | 20.5 |
| 50 | 30 | 58.4 | 33.9 | | | −27.9 | | | 25.0 |

METHODS FOR CONTROLLING THE GALACTOSYLATION PROFILE OF RECOMBINANTLY-EXPRESSED PROTEINS

RELATED APPLICATION

This application claims the benefit of U.S. Provisional Application Ser. No. 61/479,727, filed Apr. 27, 2011, which is also incorporated herein by reference in its entirety.

1. INTRODUCTION

The present invention relates to methods for modulating the glycosylation profile of recombinantly-expressed proteins. In particular, the present invention relates to methods of controlling the galactosylation profile of recombinantly-expressed proteins by supplementing production media with manganese and/or galactose.

2. BACKGROUND OF THE INVENTION

Utilization of a particular type of production media, e.g., hydrolysate-based media or chemically defined media ("CD" or "CDM"), for CHO cell cultures producing recombinant proteins can enhance cell growth and target protein production. However, recombinant proteins produced in different CD or hydrolysate-based media can exhibit large differences in their product quality profile. In certain instances, this variability can lead to increases in the fraction of the agalactosyl fucosylated biantennary oligosaccharides NGA2F+NGA2F-GlcNAc and decreases in the fraction of galactose-containing fucosylated biantennary oligosaccharides NA1F+NA2F. Shifts in the glycosylation profile of recombinant proteins of this magnitude are significant as these shifts may render the resulting production lots of the target protein out of compliance with approved process specifications.

3. SUMMARY OF THE INVENTION

The present invention relates to methods for modulating the glycosylation profile of recombinantly-expressed proteins. In particular, the present invention relates to methods of controlling the galactosylation profile of recombinantly-expressed proteins by supplementing production media with manganese and/or galactose. In certain embodiments the production media is a hydrolysate-based media or a CD media.

In certain embodiments, the present invention is directed to methods of controlling the galactosylation profile of recombinantly-expressed antibody. In certain embodiments, the recombinantly-expressed antibody is an anti-TNFα antibody. In certain embodiments, the recombinantly-expressed anti-TNFα antibody is adalimumab.

In certain embodiments, the present invention is directed to methods of controlling the galactosylation profile of recombinantly-expressed proteins by supplementing a production medium, e.g., a hydrolysate-based or a CD medium, used in the production of recombinantly-expressed proteins with manganese and/or galactose. In certain embodiments, the manganese supplement can take the form of any biologically-acceptable manganese salt, for example, but not limited to, manganese (II) chloride. In certain embodiments, the galactose supplement can take the form of any biologically-acceptable galactose-containing compound, for example, but not limited to, D-(+)-galactose.

In certain embodiments, the present invention is directed to methods of controlling the galactosylation profile of recombinantly-expressed proteins by supplementing a production medium, e.g., a hydrolysate-based or a CD medium, used in the production of recombinantly-expressed proteins with a sufficient amount of manganese and/or a manganese-containing supplement to achieve the following manganese concentrations in the production media: at least about 0.1, at least about 0.2, at least about 0.5, at least about 1.0, at least about 10, at least about 20, at least about 25, at least about 40, at least about 50, at least about 60, at least about 75, at least about 80, or at least about 100 μM, wherein that production media is used to dilute a supplement-free cell culture growth media containing no supplement by a ratio of about 1:4 or about 1:5 (supplement-free growth media:supplemented production media). In certain embodiments, the present invention is directed to methods of controlling the galactosylation profile of recombinantly-expressed proteins by supplementing a production medium, e.g., a hydrolysate-based or a CD medium, used in the production of the recombinantly-expressed proteins with sufficient galactose and/or galactose-containing supplement to achieve the following galactose concentrations in the production media: at least about 1, at least about 4, at least about 5, at least about 10, at least about 15, at least about 20, at least about 30, at least about 40, at least about 60, or at least about 100 mM, wherein that production media is used to dilute a supplement-free cell culture growth media containing no supplement by a ratio of about 1:4 or about 1:5 (supplement-free growth media:supplemented production media).

In certain embodiments, the present invention is directed to methods of controlling the galactosylation profile of recombinantly-expressed proteins by supplementing a production medium, e.g., a hydrolysate-based or a CD medium, used in the production of recombinantly-expressed proteins with sufficient manganese and/or a manganese-containing supplement and sufficient galactose and/or galactose-containing supplement to achieve at least about the following manganese (Mn) and galactose (Gal) concentrations in the production media presented as Mn (μM)/Gal (mM): 0/1, 0/4, 0/5, 0/10, 0/15, 0/20, 0/30, 0/40, 0/60, 0/100, 0.1/0, 0.2/0, 0.5/0, 1.0/0, 10/0, 20/0, 25/0, 40/0, 50/0, 75/0, 80/0, 100/0, 0.2/1, 0.2/4, 0.2/30, 0.5/1, 0.5/4, 0.5/30, 10/10, 10/20, 10/40, 20/10, 20/20, 20/40, 25/15, 40/10, 40/20, 40/40, 40/100, 50/30, 60/20, 60/40, 60/100, 80/20, 80/40, 80/100, 100/20, 100/40, 100/100, wherein that production media is used to dilute a supplement-free cell culture growth media containing no supplement by a ratio of about 1:4 or about 1:5 (supplement-free growth media: supplemented production media).

In certain embodiments, the present invention is directed to methods of controlling the galactosylation profile of recombinantly-expressed proteins by supplementing a production medium, e.g., a hydrolysate-based or a CD medium, used in the production of recombinantly-expressed proteins with sufficient manganese and/or a manganese-containing supplement and sufficient galactose and/or galactose-containing supplement to achieve at least about the following manganese (Mn) and galactose (Gal) concentrations in the production media presented as Mn (μM)/Gal (mM): 0.2/1, 0.2/4, 0.2/30, 0.5/1, 0.5/4, 0.5/30, 10/10, 10/20, 10/40, 20/10, 20/20, 20/40, 25/15, 40/10, 40/20, 40/40, 40/100, 50/30, 60/20, 60/40, 60/100, 80/20, 80/40, 80/100, 100/20, 100/40, 100/100, wherein that production media is used to dilute a supplement-free cell culture growth media containing no supplement by a ratio of about 1:4 or about 1:5 (supplement-free growth media: supplemented production media).

4. BRIEF DESCRIPTION OF THE FIGURES

FIG. 5 summarizes the effect of manganese and/or galactose addition to CDM GIA-1 on galactosylation of adalimumab relative to control in CHO cell line.

Figure 6A:
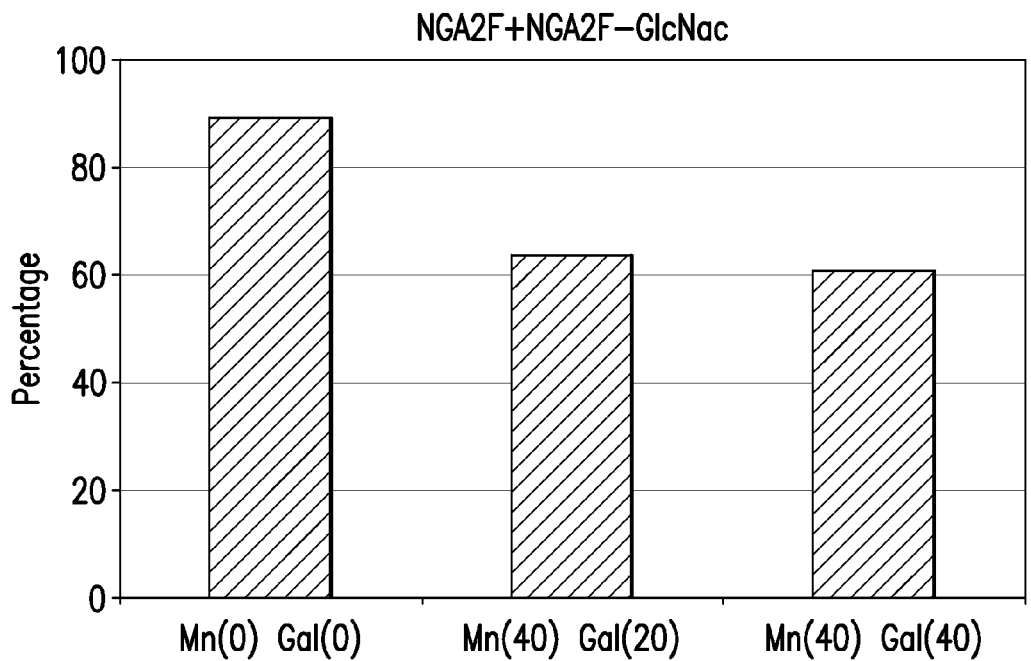
Figure 6B:
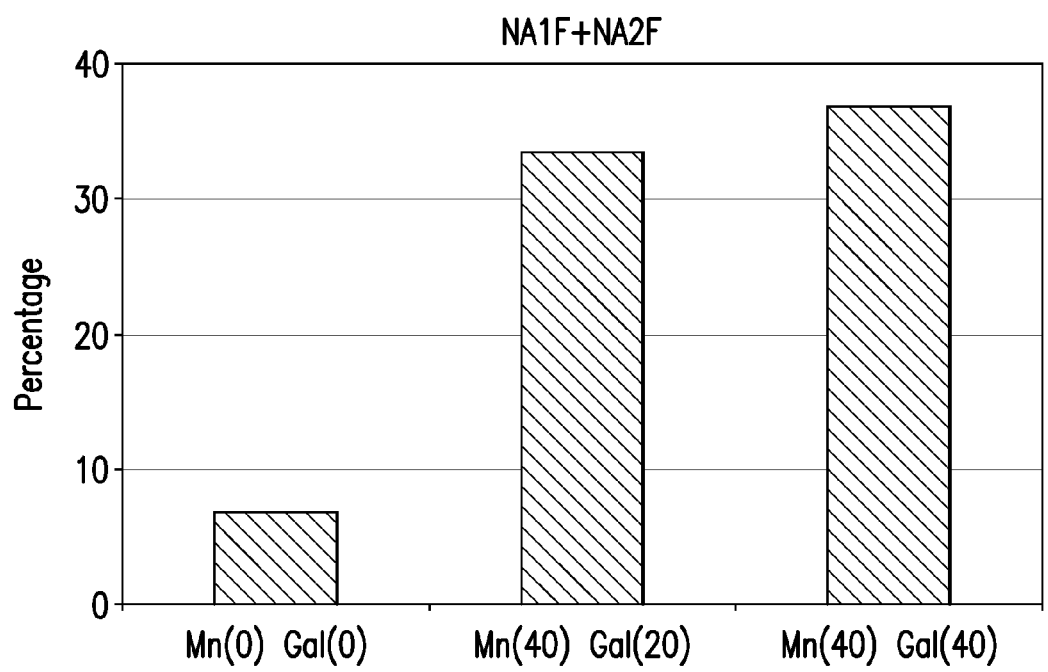

FIG. 6 depicts the galactosylation profile of adalimumab in CHO cell line in CDM GIA-1 in fed-batch 3 L bioreactors (A) NGA2F+NGA2F-GlcNac; (B) NA1F+NA2F.

FIG. 7 depicts the culture performance of CHO cell line in CDM HyClone CDM4CHO in batch shake flasks (A) Culture growth; (B) Viability.

Figure 8A:
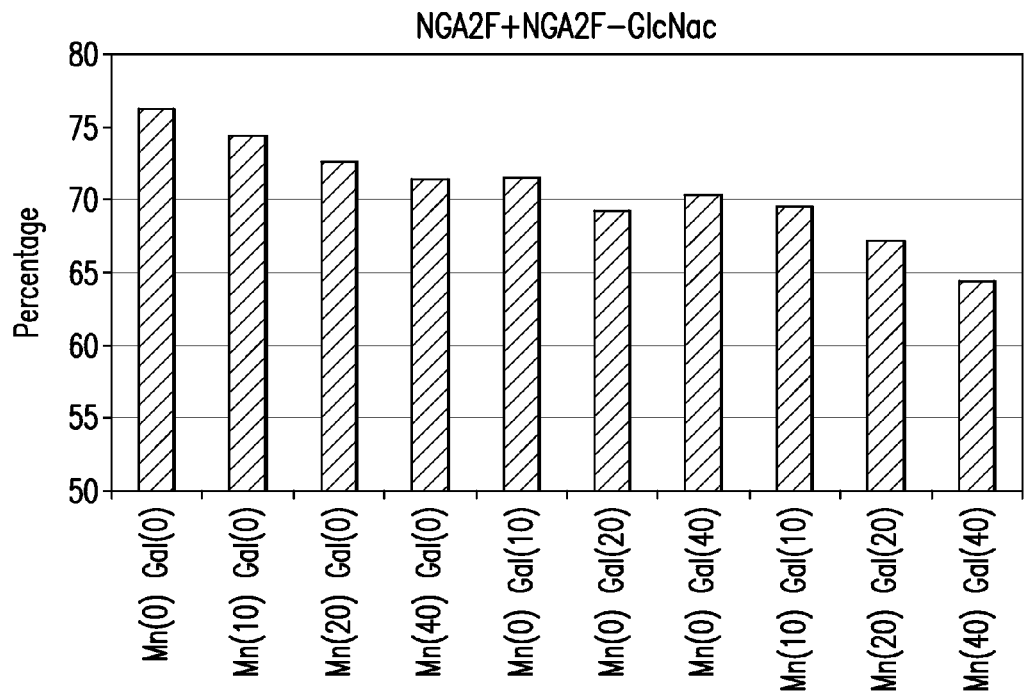
Figure 8B:
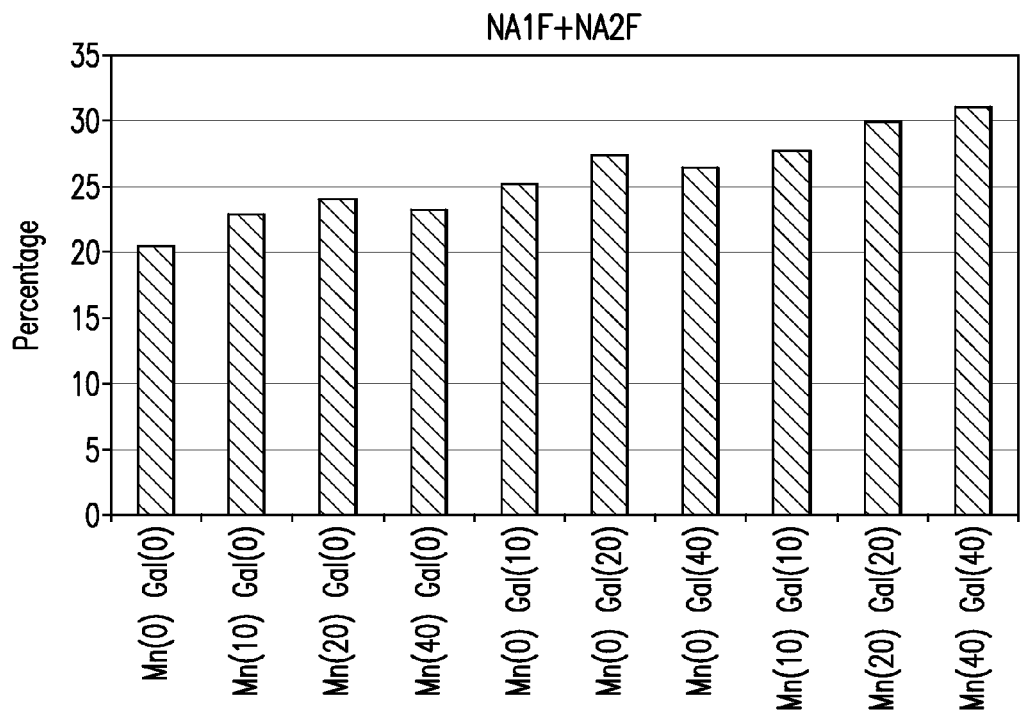

FIG. 8 depicts the galactosylation profile of adalimumab in CHO cell line in CDM HyClone CDM4CHO in batch shake flasks (A) NGA2F+NGA2F-GlcNac; (B) NA1F+NA2F.

FIG. 9 summarizes the effect of manganese and/or galactose addition to CDM HyClone CDM4CHO on galactosylation of adalimumab relative to control in CHO cell line.

FIG. 10 depicts the culture performance of CHO cell line in hydrolysate media in batch shake flasks (A) Culture growth; (B) Viability.

Figure 11A:
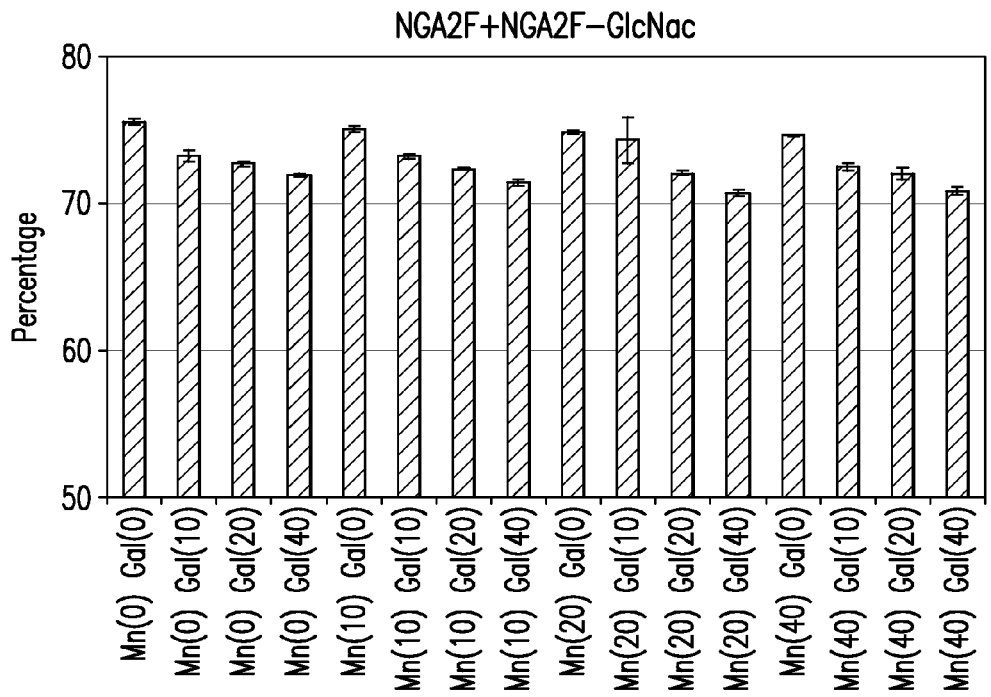
Figure 11B:
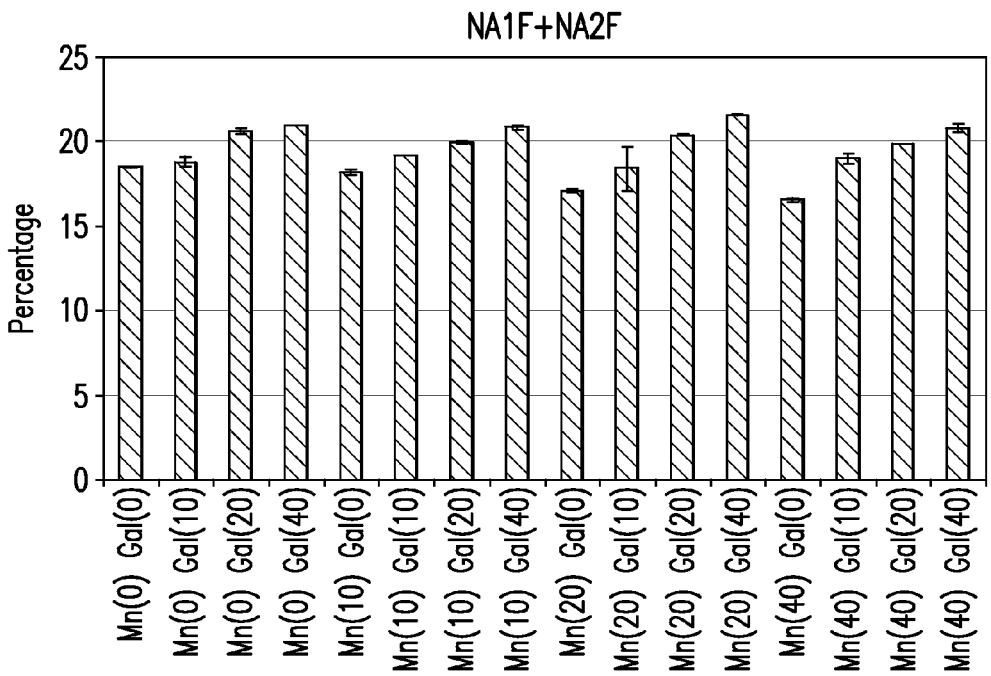

FIG. 11 depicts the galactosylation profile of adalimumab in CHO cell line in hydrolysate media in batch chake flasks (A) NGA2F+NGA2F-GlcNac; (B) NA1F+NA2F.

FIG. 12 summarizes the effect of manganese and/or galactose addition to hydrolysate media on galactosylation of adalimumab relative to control in CHO cell line.

FIG. 13 depicts the culture performance of adalimumab-producing CHO cell line #2 in CDM GIA-1 in batch shake flasks (A) Culture growth; (B) Viability.

Figure 14A:
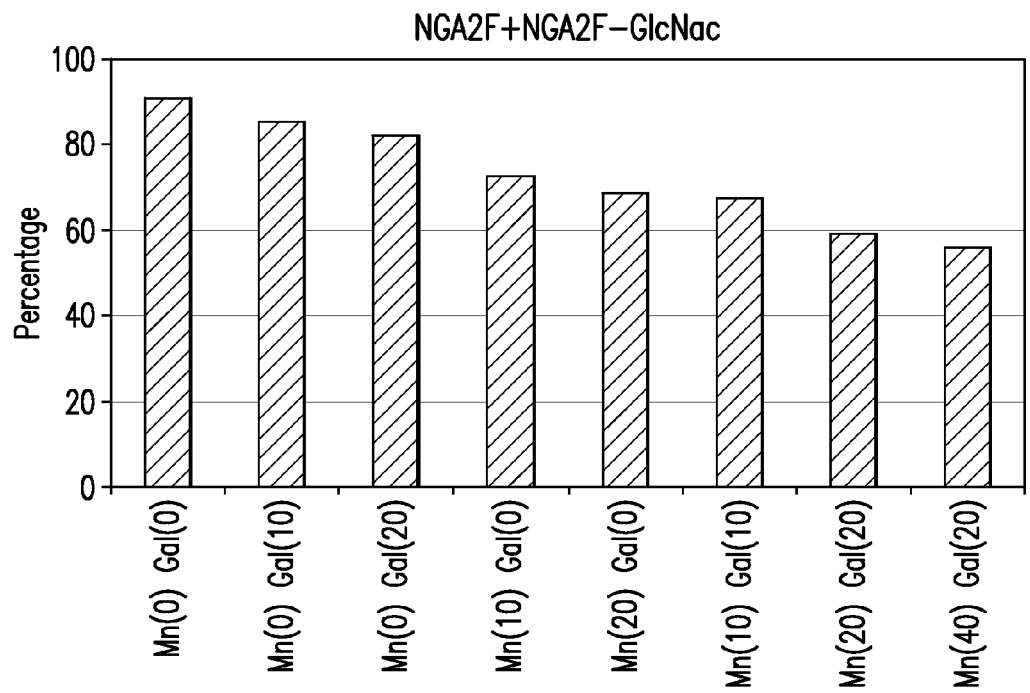
Figure 14B:
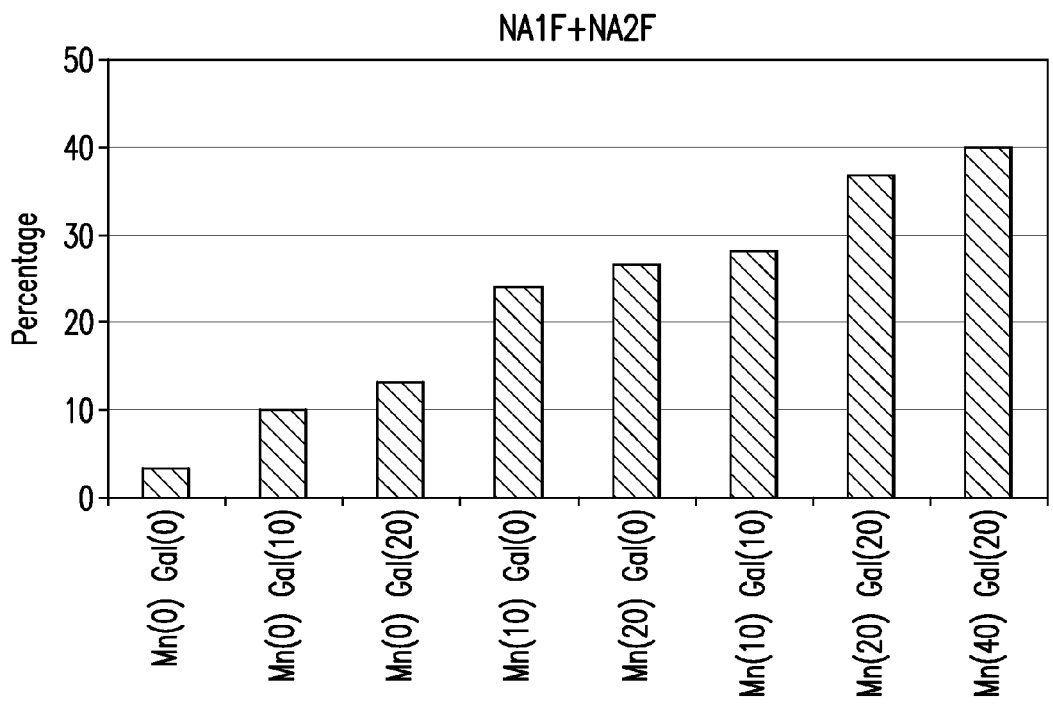

FIG. 14 depicts the galactosylation profile of adalimumab in CHO cell line #2 in CDM GIA-1 in batch shake flasks (A) NGA2F+NGA2F-GlcNac; (B) NA1F+NA2F.

FIG. 15 summarizes the effect of manganese and/or galactose addition to CDM GIA-1 on galactosylation of adalimumab relative to control in CHO cell line #2.

FIG. 16 depicts culture performance of adalimumab-producing CHO cell line #3 in CDM GIA-1 in fed-batch 3 L bioreactors (A) Culture growth; (B) Viability; (C) Normalized titer.

Figure 17A:
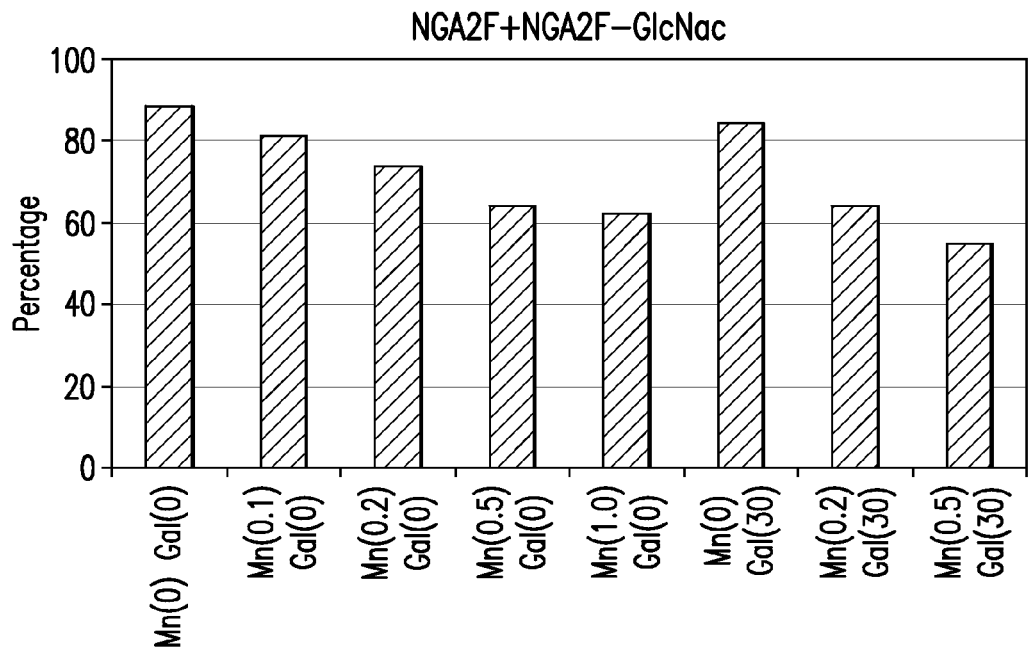
Figure 17B:
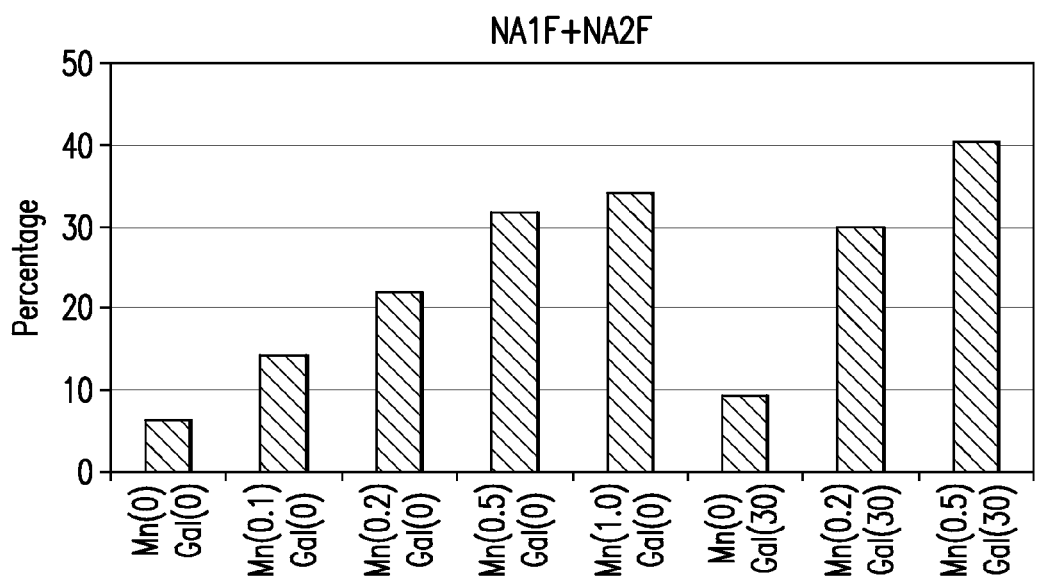

FIG. 17 depicts the galactosylation profile of adalimumab in CHO cell line #3 in CDM GIA-1 in fed-batch 3 L bioreactors (A) NGA2F+NGA2F-GlcNac; (B) NA1F+NA2F.

FIG. 18 summarizes the effect of manganese and/or galactose addition to CDM GIA-1 on galactosylation of adalimumab relative to control in CHO cell line #3.

FIG. 19 depicts the culture performance of adalimumab-producing NS0 cell line in CDM PFBM-3/PFFM-4 fed-batch shake flasks (A) Culture growth; (B) Viability; (C) Normalized titer.

Figure 20A:
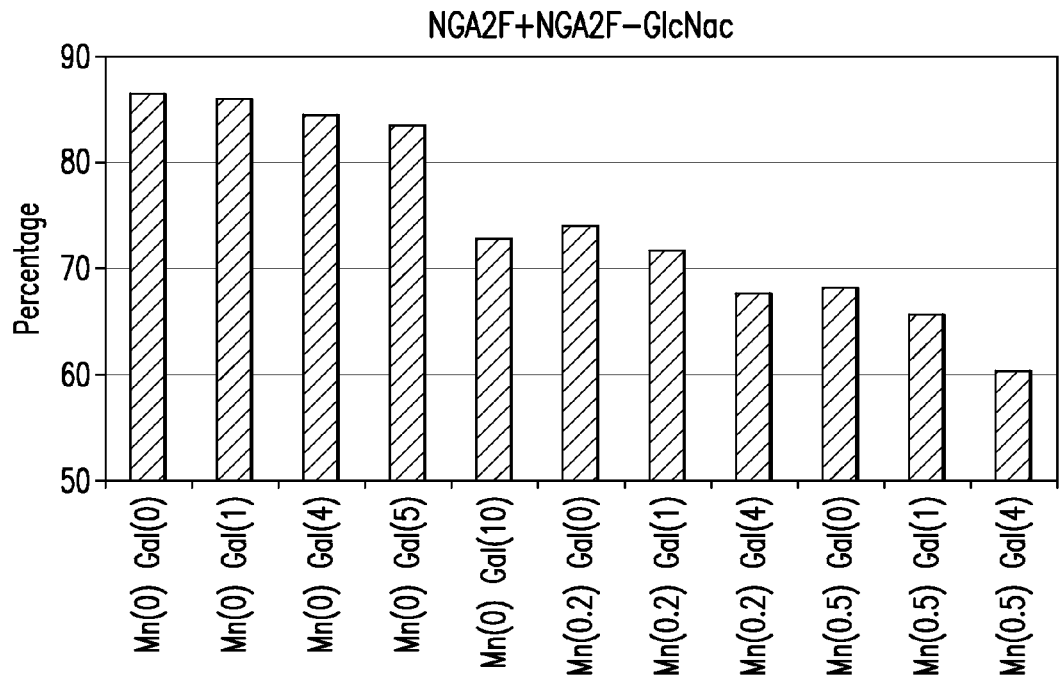
Figure 20B:
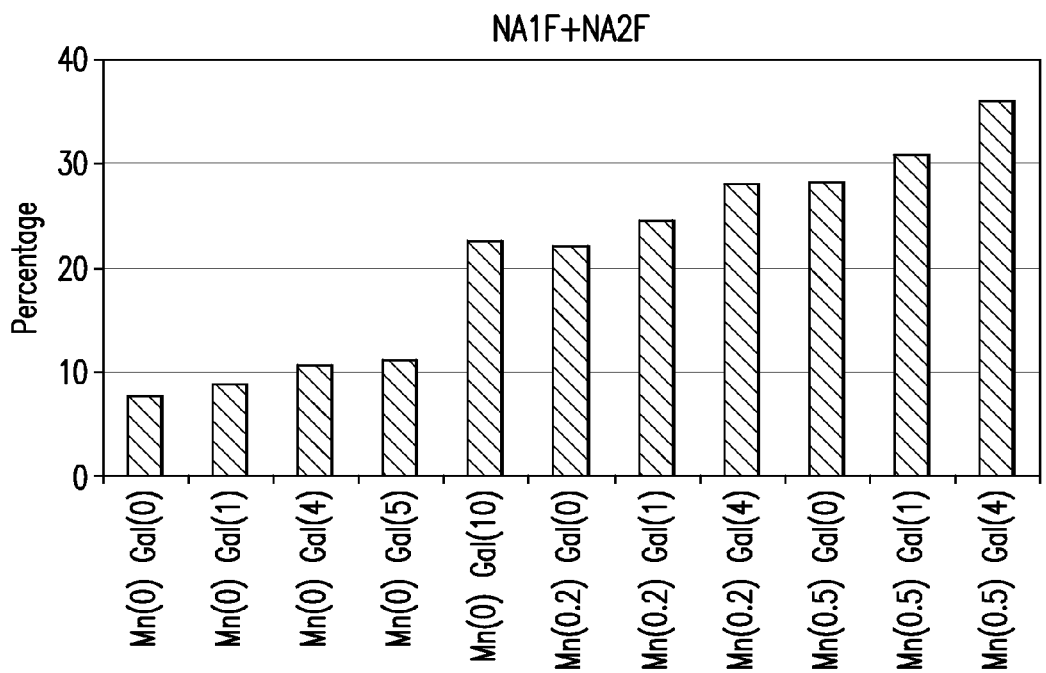

FIG. 20 depicts the galactosylation profile of adalimumab in NSO cell line in CDM PFBM-3/PFFM-4 fed-batch shake flasks (A) NGA2F+NGA2F-GlcNac; (B) NA1F+NA2F.

FIG. 21 summarizes the effect of manganese and/or galactose addition to CDM PFBM-3/PFFM-4 on galactosylation of adalimumab relative to control in NSO cell line.

FIG. 22 depicts the culture performance of CHO cell line producing mAb #1 in CDM GIA-1 in batch shake flasks (A) Culture growth; (B) Viability.

Figure 23A:
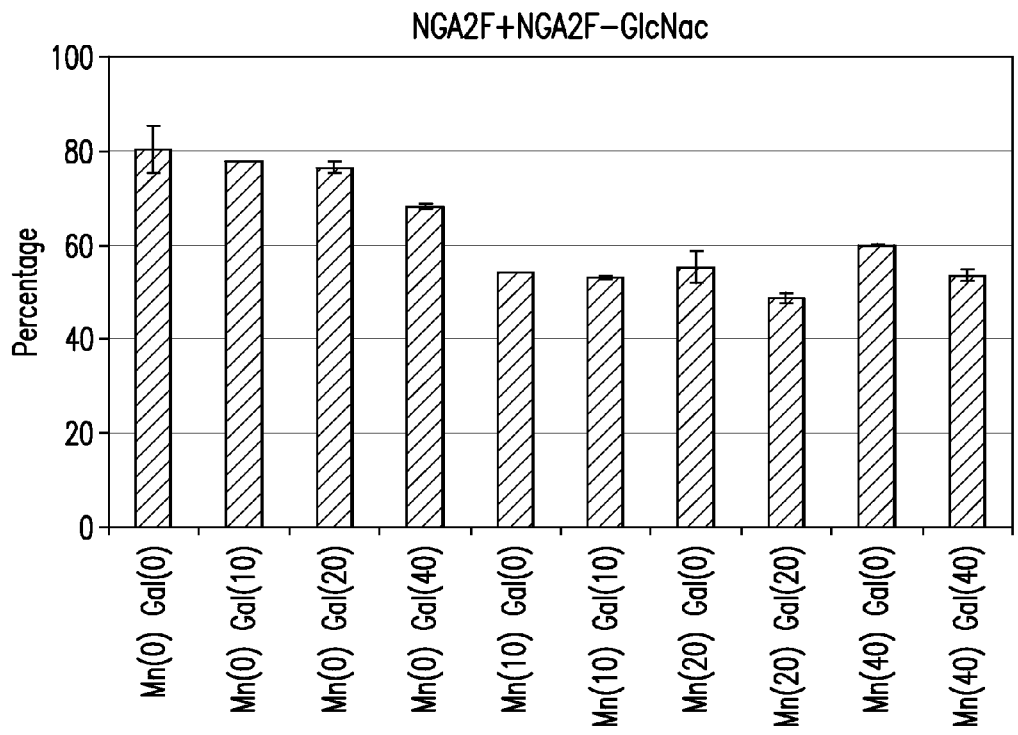
Figure 23B:
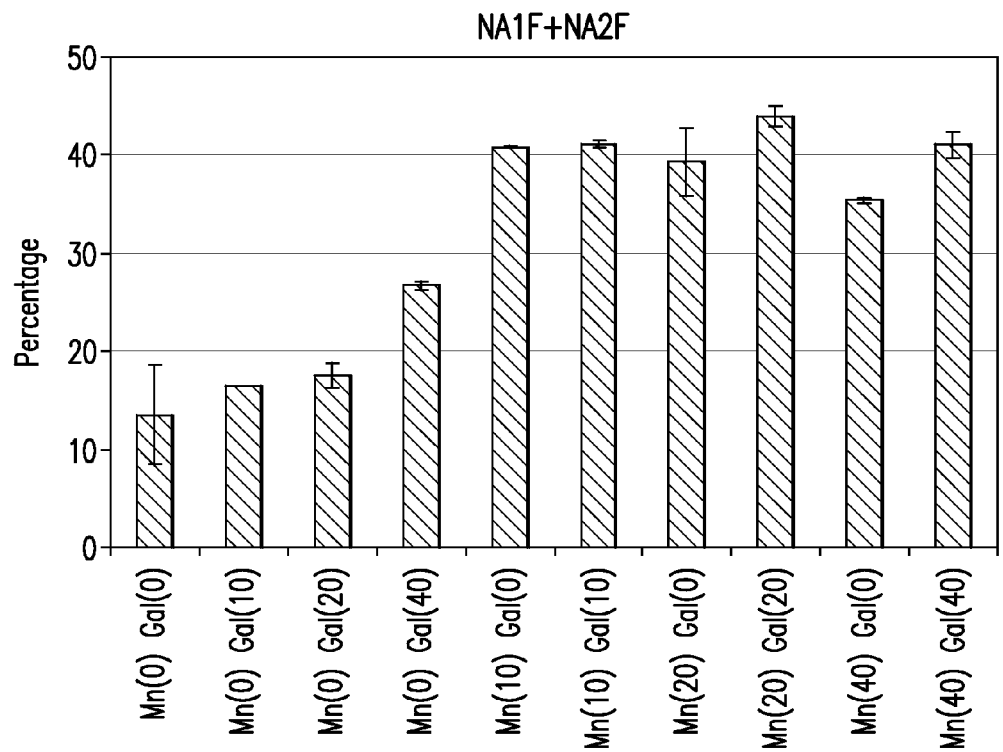

FIG. 23 depicts the galactosylation profile of mAb #1 in CDM GIA-1 in batch shake flasks (A) NGA2F+NGA2F-GlcNac; (B) NA1F+NA2F.

FIG. 24 summarizes the effect of manganese and/or galactose addition to CDM GIA-1 on galactosylation of mAb #1 relative to control.

FIG. 25 depicts culture performance of CHO cell line producing mAb #2 in CDM GIA-1 in fed-batch 3 L bioreactors (A) Culture growth; (B) Viability; (C) Normalized titer.

Figure 26A:
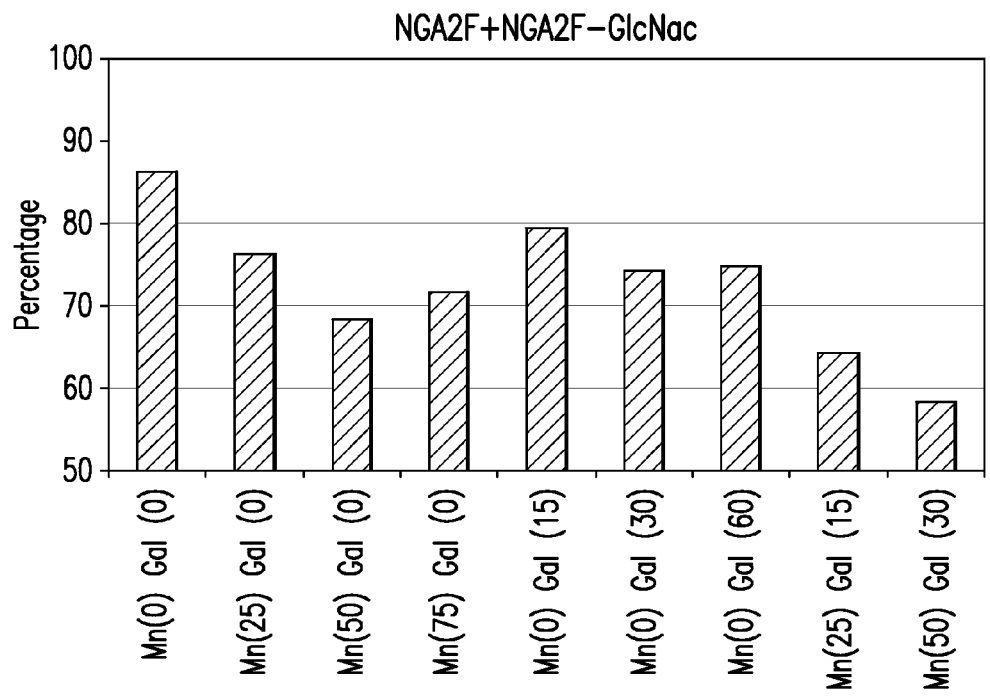
Figure 26B:
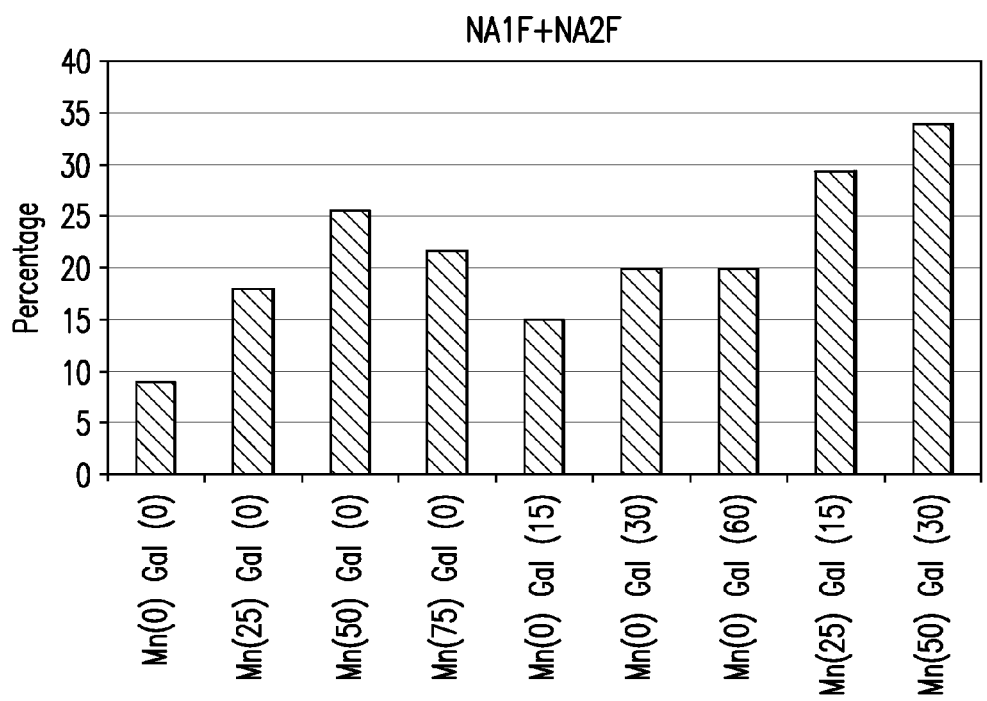

FIG. 26 depicts the glycosylation profile of mAb #2 in CDM GIA-1 in fed-batch 3 L bioreactors (A) NGA2F+NGA2F-GlcNAc; (B) NA1F+NA2F.

FIG. 27 summarizes the effect of manganese and/or galactose addition to CDM GIA-1 on galactosylation of mAb #2 relative to control.

5. DETAILED DESCRIPTION OF THE INVENTION

The present invention relates to methods modulating the glycosylation profile of recombinantly-expressed proteins. In particular, the present invention relates to methods of controlling (e.g., modulating) the galactosylation profile of recombinantly-expressed proteins by supplementing production medium, e.g., a hydrolysate-based or a CD medium, with manganese and/or galactose. For example, but not by way of limitation, the present invention demonstrates that supplementation of particular ranges of manganese and/or galactose concentrations to chemically defined media can be used to fine-tune the galactosylation profile of monoclonal antibodies produced in CHO and NSO cell lines. Similarly, supplementation of galactose alone to hydrolysate-based media is effective to modulate the galactosylation profile of the monoclonal antibody adalimumab produced in a CHO cell line in a concentration dependent manner. In view of such findings, the methods disclosed herein can be used to modulate the galactose content of recombinant proteins by controlling the amounts of manganese and/or galactose present in cell culture media. The studies described herein have also established that the changes in the galactosylation profiles obtained via implementation of the methods of the present invention are not only scale (1.5 L vs. 200 mL) and process independent (fed-batch in controlled bioreactor environment vs. batch in shake flasks), but also that no significant impact on culture growth and productivity is observed for most conditions studied.

A terminal galactose is added to NGA2F by β-galactosyltransferase enzyme in the presence of manganese chloride, to produce NA1F (in the case of an addition of a single terminal galactose) or NA2F (in the case of an addition of two terminal galactose molecules). This galactosyltransferase-mediated reaction employs UDP-galactose as the sugar substrate and $Mn^{2+}$ as a cofactor for galactosyltransferase. Thus, without being bound by theory, it is believed that a change in protein homogeneity taking the form of an increase in the fraction of N-linked oligosaccharide NGA2F and a decrease in the fraction of NA1F+NA2F N-linked oligosaccharides could be caused by either an insufficient amount of the substrate (UDP-galactose), the cofactor for galactosyltransferase ($Mn^{2+}$), or both.

In certain embodiments, the present invention is directed to methods of controlling the galactosylation profile of recombinantly-expressed antibody. In certain embodiments, the recombinantly-expressed antibody is an anti-TNFα antibody. In certain embodiments, the recombinantly-expressed anti-TNFα antibody is adalimumab.

In certain embodiments, the present invention is directed to methods of controlling the galactosylation profile of recombinantly-expressed proteins by supplementing a production medium, e.g., a hydrolysate-based or a CD medium, used in the production of recombinantly-expressed proteins with manganese and/or galactose. In certain embodiments, the manganese supplement can take the form of any biologically-acceptable manganese salt, for example, but not limited to, manganese (II) chloride. In certain embodiments, the galactose supplement can take the form of any biologically-acceptable galactose-containing compound, for example, but not limited to, D-(+)-galactose.

In certain embodiments, the present invention is directed to methods of controlling the galactosylation profile of recombinantly-expressed proteins by supplementing a production medium, e.g., a hydrolysate-based or a CD medium, used in the production of recombinantly-expressed proteins with a sufficient amount of manganese and/or a manganese-containing supplement to achieve at least about the following manganese concentrations in the production media: at least about 0.1, at least about 0.2, at least about 0.5, at least about 1.0, at least about 10, at least about 20, at least about 25, at least about 40, at least about 50, at least about 60, at least about 75, at least about 80, or at least about 100 µM, wherein that production media is used to dilute a supplement-free cell culture growth media containing no supplement by a ratio of about 1:4 or about 1:5 (supplement-free growth media: supplemented production media). In certain embodiments, the present invention is directed to methods of controlling the galactosylation profile of recombinantly-expressed proteins by supplementing a production medium, e.g., a hydrolysate-based or a CD medium, used in the production of recombinantly-expressed proteins with sufficient galactose and/or galactose-containing supplement to achieve at least about the following galactose concentrations in the production media: at least about 1, at least about 4, at least about 5, at least about 10, at least about 15, at least about 20, at least about 30, at least about 40, at least about 60, or at least about 100 mM, wherein that production media is used to dilute a supplement-free cell culture growth media containing no supplement by a ratio of about 1:4 or about 1:5 (supplement-free growth media: supplemented production media).

In certain embodiments, the present invention is directed to methods of controlling the galactosylation profile of recombinantly-expressed proteins by supplementing a production medium, e.g., a hydrolysate-based or a CD medium, used in the production of recombinantly-expressed proteins with sufficient manganese and/or a manganese-containing supplement and sufficient galactose and/or galactose-containing supplement to achieve at least about the following manganese (Mn) and galactose (Gal) concentrations in the production media presented as Mn (µM)/Gal (mM): 0/1, 0/4, 0/5, 0/10, 0/15, 0/20, 0/30, 0/40, 0/60, 0/100, 0.1/0, 0.2/0, 0.5/0, 1.0/0, 10/0, 20/0, 25/0, 40/0, 50/0, 75/0, 80/0, 100/0, 0.2/1, 0.2/4, 0.2/30, 0.5/1, 0.5/4, 0.5/30, 10/10, 10/20, 10/40, 20/10, 20/20, 20/40, 25/15, 40/10, 40/20, 40/40, 40/100, 50/30, 60/20, 60/40, 60/100, 80/20, 80/40, 80/100, 100/20, 100/40, 100/100, wherein that production media is used to dilute a supplement-free cell culture growth media containing no supplement by a ratio of about 1:4 or about 1:5 (supplement-free growth media:supplemented production media).

In certain embodiments, the present invention is directed to methods of controlling the galactosylation profile of recombinantly-expressed proteins by supplementing a production medium, e.g., a hydrolysate-based or a CD medium, used in the production of recombinantly-expressed proteins with sufficient manganese and/or a manganese-containing supplement and sufficient galactose and/or galactose-containing supplement to achieve at least about the following manganese (Mn) and galactose (Gal) concentrations in the production media presented as Mn (µM)/Gal (mM): 0.2/1, 0.2/4, 0.2/30, 0.5/1, 0.5/4, 0.5/30, 10/10, 10/20, 10/40, 20/10, 20/20, 20/40, 25/15, 40/10, 40/20, 40/40, 40/100, 50/30, 60/20, 60/40, 60/100, 80/20, 80/40, 80/100, 100/20, 100/40, 100/100, wherein that production media is used to dilute a supplement-free cell culture growth media containing no supplement by a ratio of about 1:4 or about 1:5 (supplement-free growth media:supplemented production media).

Figure 3A:
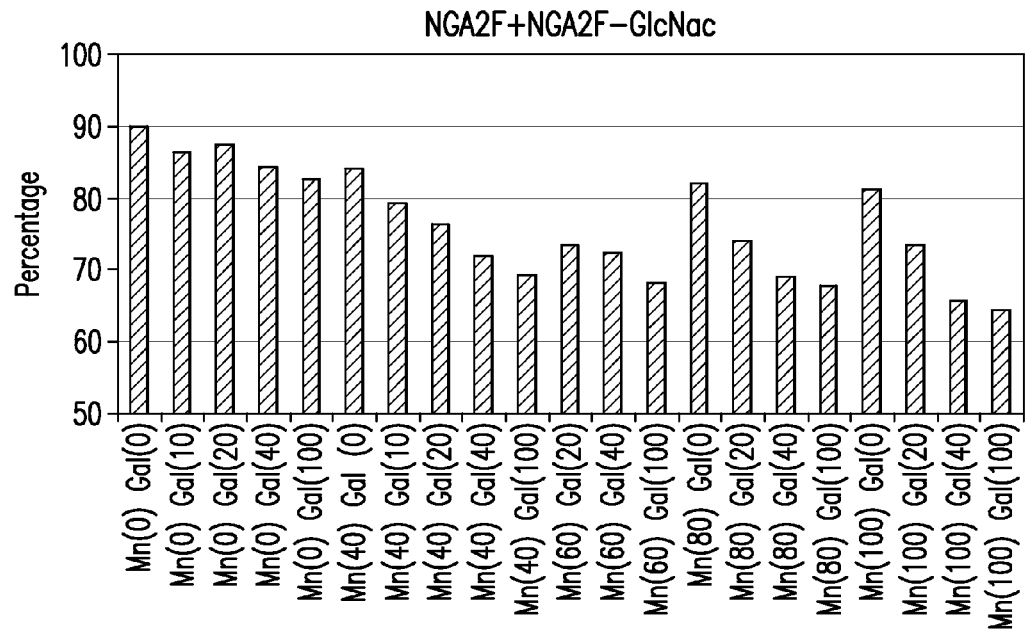
FIG. 3 depicts the galactosylation profile of adalimumab in CHO cell line in CDM GIA-1 in batch shake flasks (A) NGA2F+NGA2F-GlcNac; (B) NA1F+NA2F.
Figure 3B:
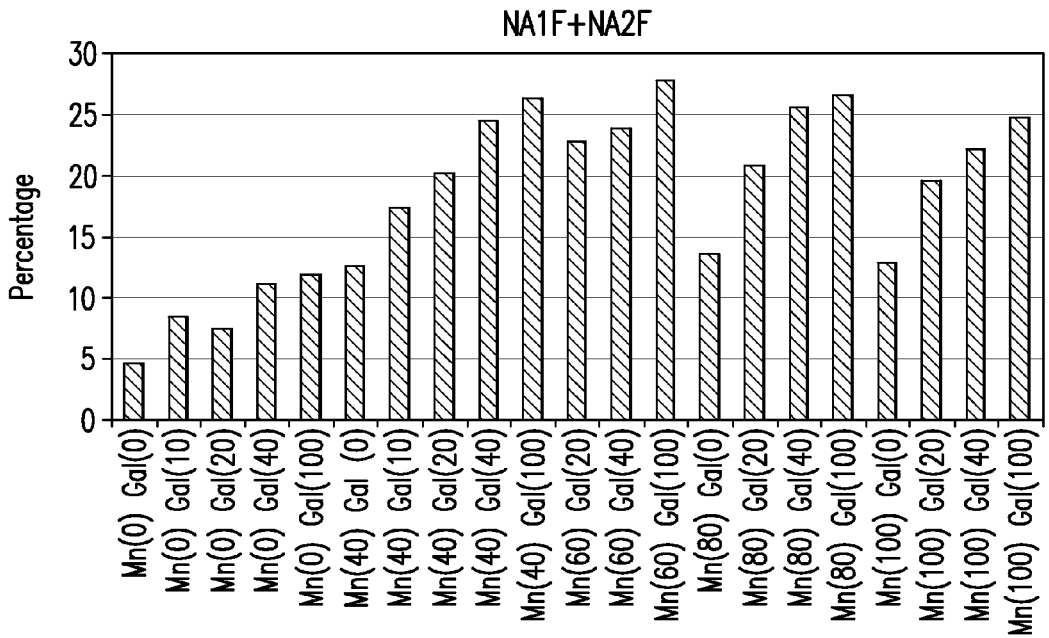
Figure 4:
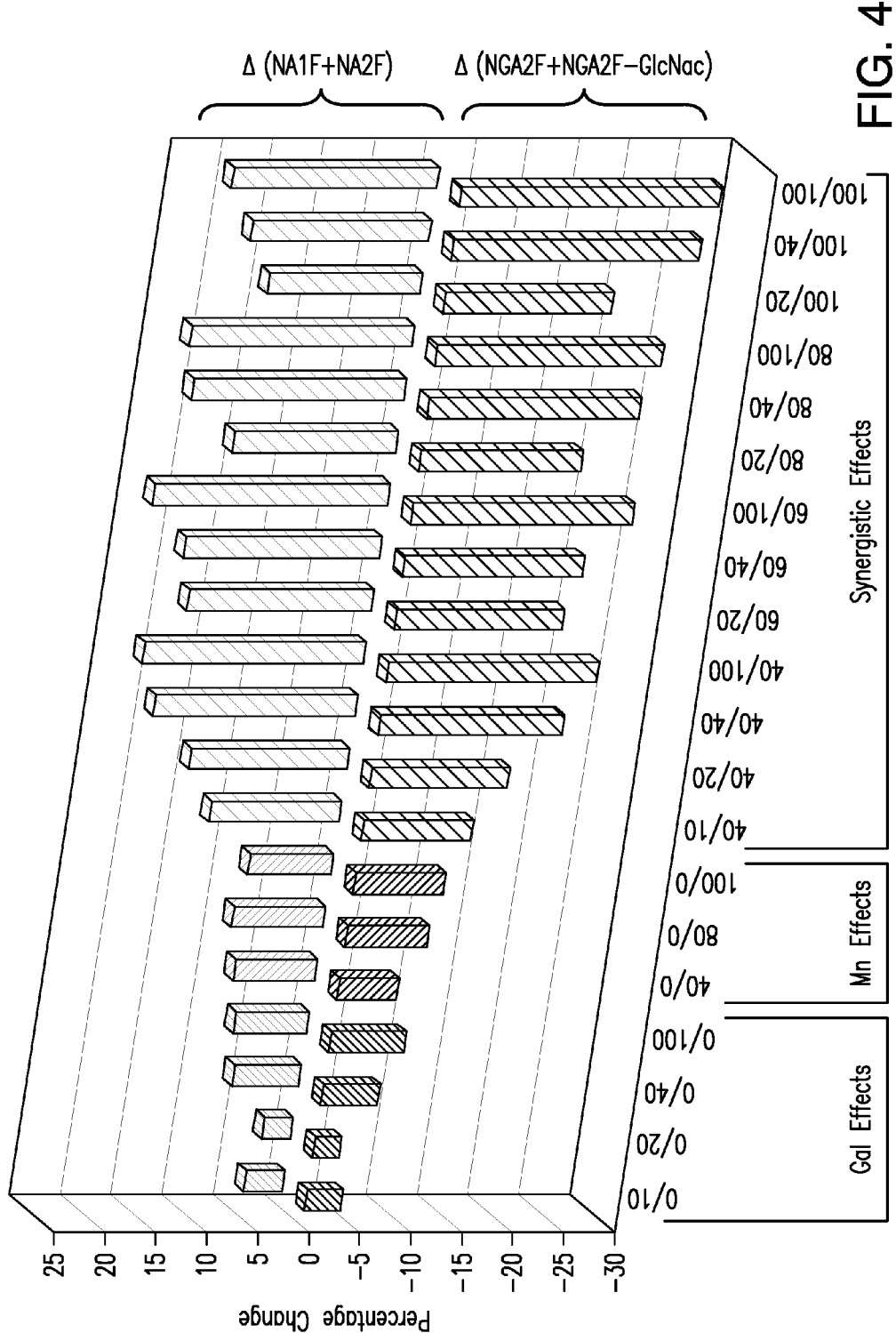
FIG. 4 depicts the percentage galactosylation change of adalimumab in CDM GIA-1 in batch shake flasks relative to control.

In certain embodiments, the production medium, e.g., a hydrolysate-based or a CD medium, used in the production of a recombinantly-expressed protein is supplemented with manganese and not galactose. For the shake flasks studies in Example 1, but not by way of limitation, addition of manganese and not galactose to production IVGN CDM GIA-1 lowered the NGA2F+NGA2F-GlcNac sum by 6% to 9% and increased the NA1F+NA2F sum by 8% to 9% (FIGS. 3, 4, and 5). No further increase in manganese concentration was explored in the experimental design due to the growth inhibition observed at about 100 µM.

In certain embodiments, the production medium, e.g., a hydrolysate-based or a CD medium, used in the production of a recombinantly-expressed protein is supplemented with galactose and not manganese. For the shake flasks studies in Example 1, but not by way of limitation, addition of galactose only to production IVGN CDM GIA-1 lowered the NGA2F+NGA2F-GlcNac sum by 3% to 7% and increased NA1F+NA2F by 3% to 7% (FIGS. 3, 4, and 5). These findings indicate that a manganese concentration of about 100 µM and a galactose concentration of about 100 mM represent the maximum range of interest for this Example 1.

In certain embodiments, the production medium, e.g., a hydrolysate-based media or a CD media, used in the production of a recombinantly-expressed protein is supplemented with both manganese and galactose. For example, but not by way of limitation, the studies outlined in Example 1 indicate that the addition of combinations of manganese and galactose to production IVGN CDM GIA-1 resulted in a significant decrease in the NGA2F+NGA2F-GlcNac sum of 11% to 26% and a corresponding significant increase in the NA1F+NA2F sum of 13% to 23% as compared to the control condition where no manganese or galactose were added to the production media (FIGS. 3, 4, and 5). The effect on modulation of galactosylation of adalimumab in production IVGN CDM GIA-1 with the combined addition of manganese chloride and galactose was synergistic. In particular, the combined addition of manganese chloride and galactose decreased the NGA2F+NGA2F-GlcNac sum and increased the NA1F+NA2F sum by a larger percentage than by adding manganese or galactose alone and summing up their individual effects. For example, but not by way of limitation, addition of 40 µM manganese chloride alone reduced the NGA2F sum by 6%, and addition of 40 mM galactose alone decreased the NGA2F+NGA2F-GlcNac sum by 6%. However, the combined addition of manganese chloride and galactose at these same concentrations (i.e. 40 µM manganese+40 mM galactose) led to an 18% reduction in the NGA2F+NGA2F-GlcNac sum, 6% higher than their combined individual contributions to the reduction of the NGA2F+NGA2F-GlcNac sum. We define this effect as being synergistic and maintain this definition throughout the invention. The largest percent decrease in the NGA2F+NGA2F-GlcNac sum of approximately 26% was observed with the combined addition of 100 µM manganese chloride and 100 mM galactose. The largest percent increase in the NA1F+NA2F sum of approximately 23% was recorded with the combined addition of 60 μM manganese chloride and 100 mM galactose.

For the fed-batch bioreactor study described in Example 1, two manganese chloride and galactose combinations were studied and the results indicate that the decrease in the NGA2F+NGA2F-GlcNac sum and the corresponding increase in the NA1F+NA2F sum was scale (1.5 L vs. 200 mL) and process independent (fed-batch in controlled bioreactor environment vs. batch in shake flasks). For example, but not by way of limitation, the combined addition of 40 μM manganese chloride and 20 mM galactose to both production basal CDM GIA-1 and feed CDM JCL-5 decreased the NGA2F+NGA2F-GlcNac sum by 26% and increased the NA2F+NA2F sum by 27% compared to the control cultures (FIG. 6). A further increase in the galactose concentration to 40 mM in addition to manganese supplementation at 40 μM concentration resulted in an additional 3% decrease in the NGA2F+NGA2F-GlcNac sum, and a corresponding 3% increase in the NA1F+NA2F sum In certain embodiments, the present invention is directed to the supplementation of CD media used in the production of a recombinantly-expressed protein with galactose and/or manganese. That such supplementation is effective across distinct CD media is evidenced by the results outlined in Example 2. Specifically, Example 2 results indicate that the addition of manganese chloride alone within the range of 0 to 40 μM to production CDM HyClone CDM4CHO decreased the NGA2F+NGA2F-GlcNac sum by a maximum of 5% in a concentration dependent manner (FIG. 8). A comparable maximum increase of 4% in the NA1F+NA2F sum was also achieved. Addition of galactose alone up to a maximum concentration of 40 mM yielded a 6% maximum decrease in the NGA2F+NGA2F-GlcNac sum and a corresponding 6% increase in the NA1F+NA2F sum. Modulation of galactosylation was also observed in production CDM HyClone CDM4CHO cultures supplemented with both manganese chloride and galactose. An additive effect was observed in cultures supplemented with both manganese chloride and galactose. The combined addition of manganese chloride and galactose decreased the NGA2F+NGA2F-GlcNac sum and increased the NA1F+NA2F sum by a comparable percentage as when manganese or galactose were added alone and their individual effects were summed up (FIG. 9). For example, but not by way of limitation, addition of 40 μM manganese chloride alone reduced the NGA2F+NGA2F-GlcNac sum by 5%, and addition of 40 mM galactose alone decreased the NGA2F sum by 6%. The combined addition of manganese chloride and galactose at these same concentrations (i.e. 40 μM manganese+40 mM galactose) led to a 12% reduction in the NGA2F+NGA2F-GlcNac sum. We define this effect as being additive and maintain this definition throughout the invention. The highest percentage decrease in the NGA2F sum of 12% and the corresponding 11% increase in the NA1F+NA2F sum was observed for the culture supplemented with 40 μM manganese chloride and 40 mM galactose.

In certain embodiments, the present invention is directed to the supplementation of a hydrolysate-based media used in the production of a recombinantly-expressed protein with galactose and/or manganese. For example, as outlined in Example 3, the addition of manganese chloride alone within the range of 0 to 40 μM to hydrolysate-based production media decreased the NGA2F+NGA2F-GlcNac sum by approximately 1%, although that change is within the oligosaccharide assay variability (FIG. 11). The addition of galactose alone up to a maximum concentration of 40 mM yielded a maximum decrease of 4% in the NGA2F+NGA2F-GlcNac sum and a corresponding 4% maximum increase in the NA1F+NA2F sum. Such oligosaccharide profile changes achieved with the addition of galactose alone are comparable to the changes recorded when combinations of galactose and manganese chloride were added to the hydrolysate-based media. For example, the combined addition of manganese chloride ranging from 0 to 40 μM and galactose ranging from 0 to 40 mM to hydrolysate-based media led to an approximate 5% maximum decrease in the NGA2F+NGA2F-GlcNac sum and a corresponding 3% increase in the NA1F+NA2F sum (FIG. 12). The highest percentage decrease of 5% in the NGA2F+NGA2F-GlcNac sum and the corresponding 4% increase in the NA1F+NA2F sum was observed for the culture supplemented with 40 mM galactose and either 20 μM or 40 μM manganese chloride.

The compositions and methods of the present invention also find use across distinct cell lines. For example, but not by way of limitation, the study described in Example 4 illustrates that the supplementation of a CD media, GIA-1, with galactose and/or manganese is effective to modulate galactosylation of adalimumab produced using a CHO cell line distinct from that employed in Examples 1-3. For example, but not by way of limitation, when using this alternative cell line, the addition of manganese chloride alone within the range of 0 to 20 μM to production CDM GIA-1 decreased the NGA2F+NGA2F-GlcNac sum in a concentration dependent manner and increased the NA1F+NA2F sum by approximately the same percentage. A maximum decrease of 22% in the NGA2F+NGA2F-GlcNac sum and a maximum corresponding increase of 23% in the NA1F+NA2F sum was observed with the addition of 20 μM manganese chloride (FIG. 14). Similarly, a concentration dependent decrease in the NGA2F+NGA2F-GlcNac sum and a corresponding increase in the NA1F+NA2F sum was observed with the addition of galactose alone in the range of 0 to 20 mM. A maximum decrease of 9% in the NGA2F+NGA2F-GlcNac sum and a corresponding maximum increase of 10% in the NA1F+NA2F sum was observed with the addition of 20 mM galactose. Similarly, an additive effect was observed for the oligosaccharide profiles of adalimumab produced in cultures supplemented with the combined addition of manganese chloride and galactose to GIA-1 media (FIG. 15). For example, but not by way of limitation, addition of 10 μM manganese chloride alone reduced the NGA2F+NGA2F-GlcNac sum by 18%, and addition of 10 mM galactose alone decreased the NGA2F+NGA2F-GlcNac sum by 6%. The combined addition of manganese chloride and galactose at these same concentrations led to a 24% reduction in the NGA2F+NGA2F-GlcNac sum. The highest percentage decrease of 35% in the NGA2F+NGA2F-GlcNac sum and the corresponding increase of 37% in the NA1F+NA2F sum were observed for the culture supplemented with 40 μM manganese chloride and 20 mM galactose.

That the compositions and methods of the present invention also find use across distinct cell lines is further reinforced by the results of Example 5, which employs a third adalimumab-producing cell line that is distinct from either of the adalimumab-producing cell lines of Examples 1-4. For example, but not by way of limitation, when using this third cell line, the addition of manganese chloride alone within the range of 0 to 1 μM to production CDM GIA-1 decreased the NGA2F+NGA2F-GlcNac sum in a concentration dependent manner and increased the NA1F+NA2F sum by approximately the same percentage. A maximum decrease of 26% in the NGA2F+NGA2F-GlcNac sum and a corresponding increase of 28% in the NA1F+NA2F oligosaccharides were observed with the addition of 1 μM manganese chloride (FIG. 17). The addition of galactose alone at 30 mM concentration to production CDM GIA-1 decreased the NGA2F+NGA2F-GlcNac sum by 4% and increased the NA1F+NA2F sum by 3%. Furthermore, when manganese chloride and galactose were supplemented together into the production basal and feed media, the results demonstrated a synergistic benefit towards the decrease in the NGA2F+NGA2F-GlcNAc and the increase in the NA1F+NA2F oligosaccharides which is consistent with the results demonstrated in Example 1 (FIG. 18). For example, but not by way of limitation, at 0.2 µM manganese chloride plus 30 mM galactose the observed 25% decrease in the NGA2F+NGA2F-GlcNAc sum was 6% more than the sum of the decrease observed with the addition of 0.2 µM manganese chloride alone (15%) and that of 30 mM galactose alone (4%). Similarly, the resulting 24% increase in the NA1F+NA2F sum was more than the sum of the increase observed with the addition of 0.2 µM manganese chloride alone (16%) and that of 30 mM galactose alone (3%). The combined supplementation of 0.5 µM manganese chloride+30 mM galactose also demonstrated a synergistic effect on the galactosylation profile of adalimumab produced in this third cell line. A maximum decrease compared to the control condition of 34% in the NGA2F+NGA2F-GlcNAc and a corresponding 34% maximum increase in the NA1F+NA2F oligosaccharides was observed with the combined addition of 0.5 µM manganese chloride and 30 mM galactose to chemically defined GIA-1 media.

That the compositions and methods of the present invention also find use across distinct types of cell lines is further reinforced by the results of Example 6, which employs a fourth adalimumab-producing cell line that is distinct from the adalimumab-producing cell lines of Examples 1-5, in that it is an NSO cell line. For example, but not by way of limitation, when using this NSO cell line, the addition of manganese chloride alone within the range of 0 to 0.5 µM to production CDM PFBM-3/PFFM-4 decreased the NGA2F+NGA2F-GlcNAc sum in a concentration dependent manner and increased the NA1F+NA2F sum by approximately the same percentage. A maximum decrease of 18% in the NGA2F+NGA2F-GlcNac sum and a corresponding increase of 20% in the NA1F+NA2F sum were observed with the addition of 0.5 µM manganese chloride (FIG. 20). However, manganese doses greater than 0.5 µM were not explored further due to cytotoxicity effects. Similarly, a concentration dependent decrease in the NGA2F+NGA2F-GlcNac sum and a corresponding increase in the NA1F+NA2F sum were observed with the addition of galactose alone in the range of 0 to 10 mM to production CDM PFBM-3/PFFM-4. A maximum decrease of 14% in the NGA2F+NGA2F-GlcNac sum and a corresponding increase of 15% in the NA1F+NA2F sum was observed with the addition of 10 mM galactose. In addition, the effect on modulation of galactosylation of adalimumab produced in a NSO cell line in production CDM PFBM-3/PFFM-4 supplemented with manganese chloride and galactose was synergistic (FIG. 21). For example, but not by way of limitation, addition of 0.2 µM manganese chloride alone reduced the NGA2F+NGA2F-GlcNac sum by 12%, and addition of 4 mM galactose alone decreased the NGA2F+NGA2F-GlcNac sum by 2%. However, the combined addition of manganese chloride and galactose at these same concentrations (i.e. 0.2 µM manganese+4 mM galactose) led to a 19% reduction in the NGA2F+NGA2F-GlcNac sum, 5% higher than their combined individual contributions. A maximum decrease of ~26% in the NGA2F+NGA2F-GlcNac sum and a corresponding ~28% increase in the NA1F+NA2F sum were observed with the combined addition of 0.5 µM manganese chloride and 4 mM galactose.

The compositions and methods of the present invention also find use in the production of diverse antibodies, as evidenced by the results of Example 7, which employs a CHO cell line that produced an antibody distinct from adalimumab. For example, but not by way of limitation, when producing this antibody distinct from adalimumab, the addition of manganese chloride alone within the range of 0 to 40 µM to production CDM GIA-1 decreased the NGA2F+NGA2F-GlcNac sum by a maximum of 26% (FIG. 23). A comparable maximum increase of 27% in the NA1F+NA2F sum was also achieved. Addition of galactose alone up to a maximum concentration of 40 mM yielded a maximum decrease of 12% in the NGA2F+NGA2F-GlcNac sum and a corresponding 13% maximum increase in the NA1F+NA2F sum in a concentration dependent manner. In addition, the combined addition of galactose and manganese chloride to production CDM GIA-1 resulted in a greater percent reduction in the NGA2F+NGA2F-GlcNac sum and, correspondingly, a greater percent increase in the NA1F+NA2F sum as compared to the addition of either component alone (FIG. 24). For example, but not by way of limitation, the addition of 40 µM manganese chloride alone reduced the NGA2F+NGA2F-GlcNac sum by 20%, and the addition of 40 mM galactose alone decreased the NGA2F+NGA2F-GlcNac sum by 12%. However, the combined addition of manganese chloride and galactose at these same concentrations (i.e. 40 µM manganese+40 mM galactose) led to a 27% decrease in the NGA2F+NGA2F-GlcNac sum. The highest percentage decrease of 32% in the NGA2F+NGA2F-GlcNac sum and the corresponding increase of 30% in the NA1F+NA2F sum were observed for the culture supplemented with 20 µM manganese chloride and 20 mM galactose.

That the compositions and methods of the present invention also find use when producing diverse antibodies is further reinforced by the results of Example 8, which employs a CHO cell line producing an antibody distinct from both adalimumab and the antibody of Example 7. For example, but not by way of limitation, when producing this third antibody, the addition of manganese chloride alone in the range of 0 to 75 µM to production CDM GIA-1 decreased the NGA2F+NGA2F-GlcNac sum by a maximum of 18% (FIG. 26). A comparable maximum increase of 16% in the NA1F+NA2F sum was also achieved. Addition of galactose alone up to a maximum concentration of 60 mM yielded a maximum decrease of 12% in the NGA2F+NGA2F-GlcNac sum and a corresponding 11% maximum increase in the NA1F+NA2F sum. In addition, when manganese chloride and galactose were supplemented together into the basal and feed media, the results demonstrated at least an additive effect and sometimes a synergistic effect towards the decrease in the NGA2F+NGA2F-GlcNAc sum and the increase in the NA1F+NA2F sum (FIG. 27). The synergistic effect was observed for the condition supplemented with 25 µM manganese chloride and 15 mM galactose. The observed 22% decrease in the NGA2F+NGA2F-GlcNAc sum was 5% more than the sum of the decrease observed with the addition of 25 µM manganese chloride alone (10%) and 15 mM galactose alone (7%). The additive effect was observed for the condition supplemented with 50 µM manganese chloride and 30 mM galactose. The observed 28% decrease in the NGA2F+NGA2F-GlcNAc sum was comparable to the sum of the decrease observed with the addition of 50 µM manganese chloride alone (18%) and 30 mM galactose alone (12%). A maximum decrease of 28% in the NGA2F+NGA2F-GlcNac and a corresponding 25% maximum increase in the NA1F+NA2F sum compared to the control condition was observed with the combined addition of 50 µM manganese chloride and 30 mM galactose to chemically defined GIA-1 media.

Although specifically directed to the production of antibodies, the following description outlines general techniques that can be adapted for the production of other recombinantly-expressed proteins. For example, to express a recombinant antibody, nucleic acids encoding partial or full-length light and heavy chains are inserted into one or more expression vector such that the genes are operatively linked to transcriptional and translational control sequences. (See, e.g., U.S. Pat. No. 6,914,128, the entire teaching of which is incorporated herein by reference.) In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into a separate vector or, more typically, both genes are inserted into the same expression vector. The antibody genes are inserted into an expression vector by standard methods (e.g., ligation of complementary restriction sites on the antibody gene fragment and vector, or blunt end ligation if no restriction sites are present). Prior to insertion of the antibody or antibody-related light or heavy chain sequences, the expression vector may already carry antibody constant region sequences. For example, one approach to converting particular VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, a recombinant expression vector of the invention can carry one or more regulatory sequence that controls the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, e.g., in Goeddel; Gene Expression Technology: Methods in Enzymology 185, Academic Press, San Diego, Calif. (1990), the entire teaching of which is incorporated herein by reference. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al. and U.S. Pat. No. 4,968,615 by Schaffner et al., the entire teachings of which are incorporated herein by reference.

In addition to the antibody chain genes and regulatory sequences, a recombinant expression vector of the invention may carry one or more additional sequences, such as a sequence that regulates replication of the vector in host cells (e.g., origins of replication) and/or a selectable marker gene. The selectable marker gene facilitates selection of host cells into which the vector has been introduced (see e.g., U.S. Pat. Nos. 4,399,216, 4,634,665 and 5,179,017, all by Axel et al., the entire teachings of which are incorporated herein by reference). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in dhfr-host cells with methotrexate selection/amplification) and the neo gene (for G418 selection).

An antibody, or antibody portion, of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel et al. (eds.) Current Protocols in Molecular Biology, Greene Publishing Associates, (1989) and in U.S. Pat. Nos. 4,816,397 & 6,914,128, the entire teachings of which are incorporated herein.

For expression of the light and heavy chains, the expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, such as mammalian host cells, is suitable because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss and Wood (1985) Immunology Today 6:12-13, the entire teaching of which is incorporated herein by reference).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, e.g., Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. One suitable *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183, 070); *Candida*; *Trichoderma reesia* (EP 244,234); *Neurospora crassa*; *Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

Suitable mammalian host cells for expressing the recombinant antibodies of the invention include Chinese Hamster Ovary (CHO cells) (including dhfr-CHO cells, described in Urlaub and Chasin, (1980) PNAS USA 77:4216-4220, used with a DHFR selectable marker, e.g., as described in Kaufman and Sharp (1982) Mol. Biol. 159:601-621, the entire teachings of which are incorporated herein by reference), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Other examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/−DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), the entire teachings of which are incorporated herein by reference.

Host cells are transformed with the above-described expression or cloning vectors for antibody production and cultured in conventional nutrient media modified as appropriate for inducing promoters, selecting transformants, or amplifying the genes encoding the desired sequences.

The host cells used to produce an antibody may be cultured in a variety of media. Commercially available media such as Ham's F10™ (Sigma), Minimal Essential Medium™ ((MEM), (Sigma), RPMI-1640 (Sigma), and Dulbecco's Modified Eagle's Medium™ ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767, 704; 4,657,866; 4,927,762; 4,560,655; or 5,122,469; WO 90/03430; WO 87/00195; or U.S. Pat. No. Re. 30,985 may be used as culture media for the host cells, the entire teachings of which are incorporated herein by reference. The culture conditions, such as temperature, pH, and the like, are those previously used with the host cell selected for expression, and will be apparent to the ordinarily skilled artisan.

Host cells can also be used to produce portions of intact antibodies, such as Fab fragments or scFv molecules. It is understood that variations on the above procedure are within the scope of the present invention. For example, in certain embodiments it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for antigen binding. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the original antigen by crosslinking an antibody of the invention to a second antibody by standard chemical crosslinking methods.

In a suitable system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

When using recombinant techniques, the antibody can be produced intracellularly, in the periplasmic space, or directly secreted into the medium. In one aspect, if the antibody is produced intracellularly, as a first step, the particulate debris, either host cells or lysed cells (e.g., resulting from homogenization), can be removed, e.g., by centrifugation or ultrafiltration. Where the antibody is secreted into the medium, supernatants from such expression systems can be first concentrated using a commercially available protein concentration filter, e.g., an Amicon™ or Millipore Pellicon™ ultrafiltration unit.

Prior to the process of the invention, procedures for purification of antibodies from cell debris initially depend on the site of expression of the antibody. Some antibodies can be secreted directly from the cell into the surrounding growth media; others are made intracellularly. For the latter antibodies, the first step of a purification process typically involves: lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. Where the antibody is secreted, supernatants from such expression systems are generally first concentrated using a commercially available protein concentration filter, e.g., an Amicon™ or Millipore Pellicon™ ultrafiltration unit. Where the antibody is secreted into the medium, the recombinant host cells can also be separated from the cell culture medium, e.g., by tangential flow filtration. Antibodies can be further recovered from the culture medium using the antibody purification methods of the invention.

6. EXAMPLES

6.1. Example 1

6.1.1. Materials & Methods

In the studies summarized in this example, we investigated the effects on product quality attributes resulting from the addition of manganese chloride and/or galactose to chemically defined Life Technologies Gibco, GIA-1, media (proprietary formulation) in the adalimumab-producing CHO cell line utilized in Example 3, but adapted to GIA-1 media. The studies were performed in either a batch process in shake flasks or a fed-batch process in 3 L bioreactors.

Growth and production media for the adalimumab-producing CHO cell line were prepared using a proprietary Life Technologies Gibco chemically defined media, GIA-1. Basal production and feed media were supplemented with Manganese (II) Chloride (Sigma M1787—100 mL; 1.0 M±0.1 M) and D(+)Galactose (Sigma G5388—1 kg) according to the experimental design described in Table 1. All media were filtered through Corning 0.5 L or 1 L filter systems 0.22 μm Poly(Ether Sulfone) (PES) and stored at 4° C. until use.

The cell line utilized for both studies was generated from the adalimumab-producing CHO cell utilized in Example 3 by adapting it to chemically defined GIA-1 media for 7 (2 to 3 day each) passages in a combination of 250 mL and 500 mL Corning vented non-baffled shake flasks before freezing.

Upon thaw, for the batch shake flask study, cells were expanded for 3 to 5 (2 to 3 day each) passages in a combination of 250 mL and 500 mL Corning vented non-baffled shake flasks. Production cultures were initiated in duplicate 500 mL Corning vented non-baffled shake flasks (200 mL working volume) at an initial viable cell density (VCD) of approximately 0.5×106 cells/mL. Cultures were maintained on orbital shakers at 110 revolutions per minute (RPM) in a dry incubator at 35° C. and 5% $CO_2$. The shake flask study was run in an extended batch mode by feeding a glucose solution (1.25% (v/v) of 40% solution) when the media glucose concentration fell below 3 g/L.

For the fed-batch bioreactor study, cells were expanded for 8 (2 to 3 day each) passages in Corning vented non-baffled shake flasks maintained on orbital shakers at 110 RPM and in 20 L cell bags (3 L to 10 L working volume) maintained at 20-25 RPM, 7.5° angle, and 0.25 SLPM airflow in a dry incubator at 35° C. and 5% $CO_2$. Production cultures were initiated in duplicate 3 L bioreactors (1.5 L working volume) at 35° C., 30% dissolved oxygen, 200 RPM, pH ramp from 7.1 to 6.9 over 3 days, and pH setpoint of 6.9 thereafter. A fixed split ratio of cells to media of 1:5 was utilized to initiate the production stage cultures. In the fed-batch mode, a chemically-defined feed from Life Technologies Gibco, JCL-5 (proprietary formulation), was added as follows: 3% (v/v)—day 3, 5%—day 4, 7%—day 5, 10%—day 6, and 10%—day 7. Additional glucose (1.25% (v/v) of 40% solution) was fed when the media glucose concentration fell below 3 g/L.

For all studies with CHO cell lines described throughout this invention, samples were collected daily and measured for cell density and viability using a Cedex cell counter. Retention samples for titer analysis via Poros A method were collected by centrifugation at 12,000 RPM for 5 min when the culture viability began declining. The cultures were harvested by collecting 125 mL aliquots and centrifuging at 3,000 RPM for 30 min when culture viability was near or below 50%. All supernatants were stored at −80° C. until analysis.

For all studies, the harvest samples were Protein A purified and prepared for the oligosaccharide assay using the following procedures. As a first step in the process of establishing the identity and quantifying the oligosaccharides, they are released from the protein by enzymatic digestion with N-glycanase. Once the glycans are released, the free reducing end of each glycan is labeled by reductive amination with a fluorescent tag, 2-aminobenzamide (2-AB). The resulting labeled glycans are separated by normal-phase HPLC (NP-HPLC) in acetonitrile: 50 mM ammonium formate, pH 4.4, and detected by a fluorescence detector. Quantitation is based on the relative area percent of detected sugars. Throughout this invention, the relative area percentages of the agalactosyl fucosylated biantennary oligosaccharides, denoted as NGA2F+NGA2F-GlcNAc sum, and the galactose-containing fucosylated biantennary oligosaccharides NA1F+NA2F sum are reported and discussed.

6.1.2. Experimental Design

As detailed in Table 1, for the batch shake flask study, manganese chloride was supplemented at the following concentrations in production media: 0, 40, 60, 80, and 100 μM. Galactose was supplemented at the following levels in production media: 0, 10, 20, 40, and 100 mM. Individual and combined additions of manganese chloride and galactose were studied using a comprehensive design divided into 3 sets of experiments. Each experiment had a control culture for direct comparison of culture growth, productivity, and product quality. Production media used for the control cultures was not supplemented with manganese chloride or galactose. Culture growth, productivity, and product quality data for control cultures is the average of the 3 experiments.

For the fed-batch bioreactor study, manganese chloride and galactose were supplemented to both production and feed media in the following combinations: 40 μM manganese chloride and 20 mM galactose; 40 μM manganese chloride and 40 mM galactose (Table 2). Basal and feed media for the control cultures were not supplemented with manganese chloride or galactose.

TABLE 1

Experimental design for the
batch shake flasks study (Example 1)

| Manganese (μM) | Galactose (mM) | ID |
|---|---|---|
| 0 | 0 | Mn(0) Gal(0) |
| 0 | 10 | Mn(0) Gal(10) |
| 0 | 20 | Mn(0) Gal(20) |
| 0 | 40 | Mn(0) Gal(40) |
| 0 | 100 | Mn(0) Gal(100) |
| 40 | 0 | Mn(40) Gal (0) |
| 80 | 0 | Mn(80) Gal(0) |
| 100 | 0 | Mn(100) Gal(0) |
| 40 | 10 | Mn(40) Gal(10) |
| 40 | 20 | Mn(40) Gal(20) |
| 40 | 40 | Mn(40) Gal(40) |
| 40 | 100 | Mn(40) Gal(100) |
| 60 | 20 | Mn(60) Gal(20) |
| 60 | 40 | Mn(60) Gal(40) |
| 60 | 100 | Mn(60) Gal(100) |
| 80 | 20 | Mn(80) Gal(20) |
| 80 | 40 | Mn(80) Gal(40) |
| 80 | 100 | Mn(80) Gal(100) |
| 100 | 20 | Mn(100) Gal(20) |
| 100 | 40 | Mn(100) Gal(40) |
| 100 | 100 | Mn(100) Gal(100) |

TABLE 2

Experimental design for the
fed-batch 3L bioreactors study (Example 1)

| Manganese (μM) | Galactose (mM) | ID |
|---|---|---|
| 0 | 0 | Mn(0) Gal(0) |
| 40 | 20 | Mn(40) Gal(20) |
| 40 | 40 | Mn(40) Gal(40) |

6.1.3. Culture Growth & Productivity

Figure 1A:
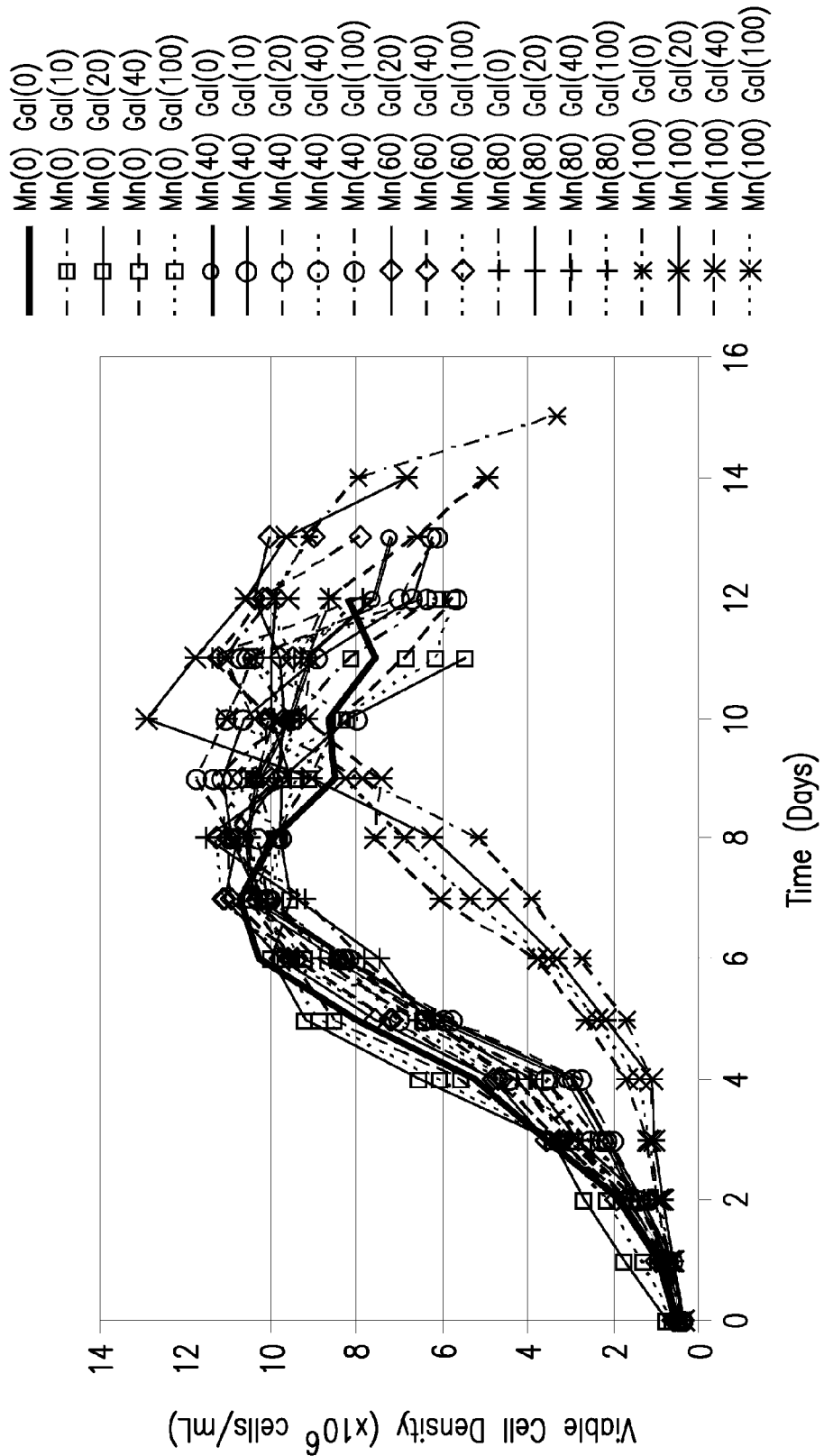
FIG. 1 depicts the culture performance of adalimumab-producing CHO cell line in CDM GIA-1 in batch shake flasks (A) Culture growth; (B) Viability; (C) Normalized titer.
Figure 1B:
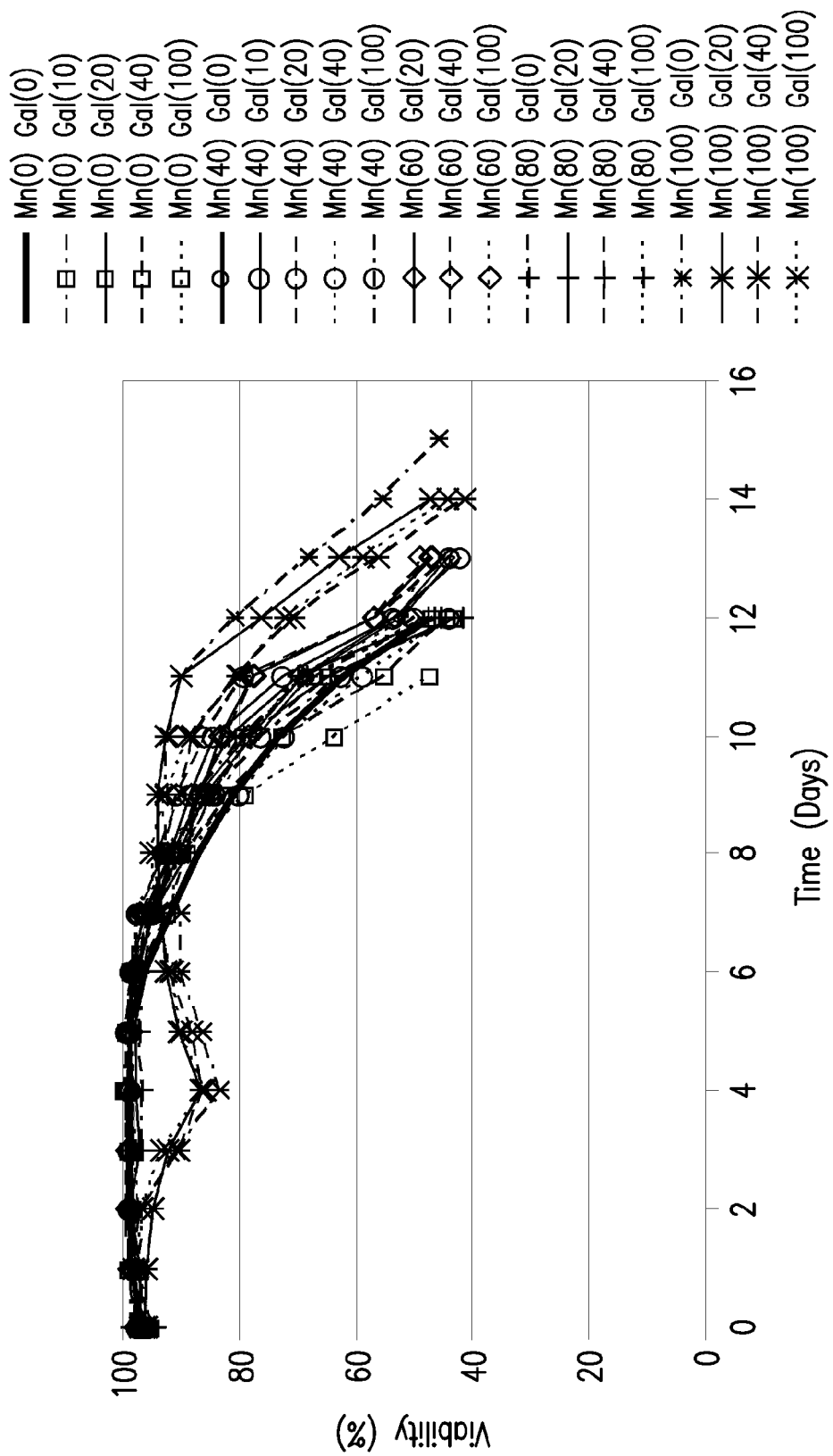
Figure 1C:
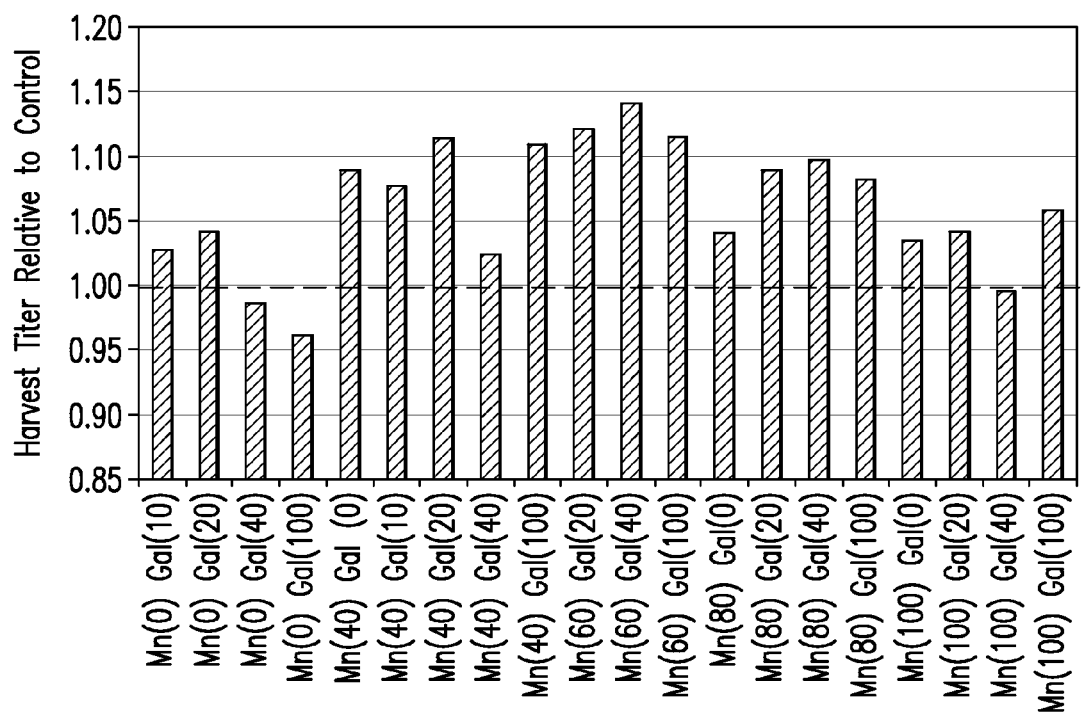
Figure 2A:
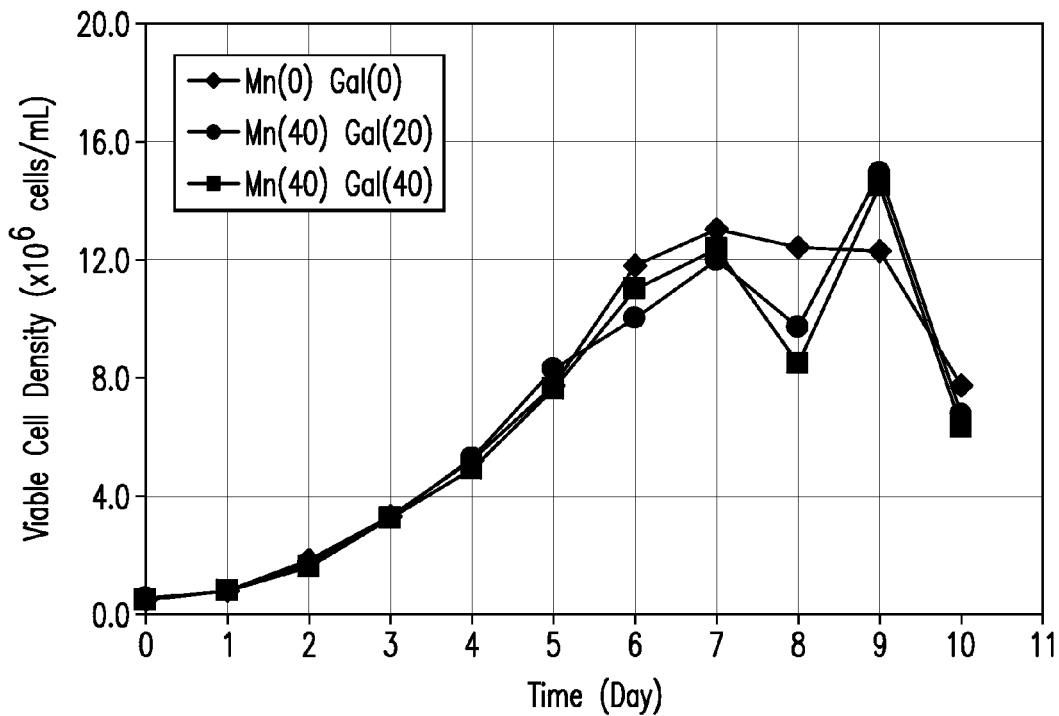
FIG. 2 depicts the culture performance of adalimumab-producing CHO cell line in CDM GIA-1 in fed-batch 3 L bioreactors (A) Culture growth; (B) Viability; (C) Normalized titer.
Figure 2B:
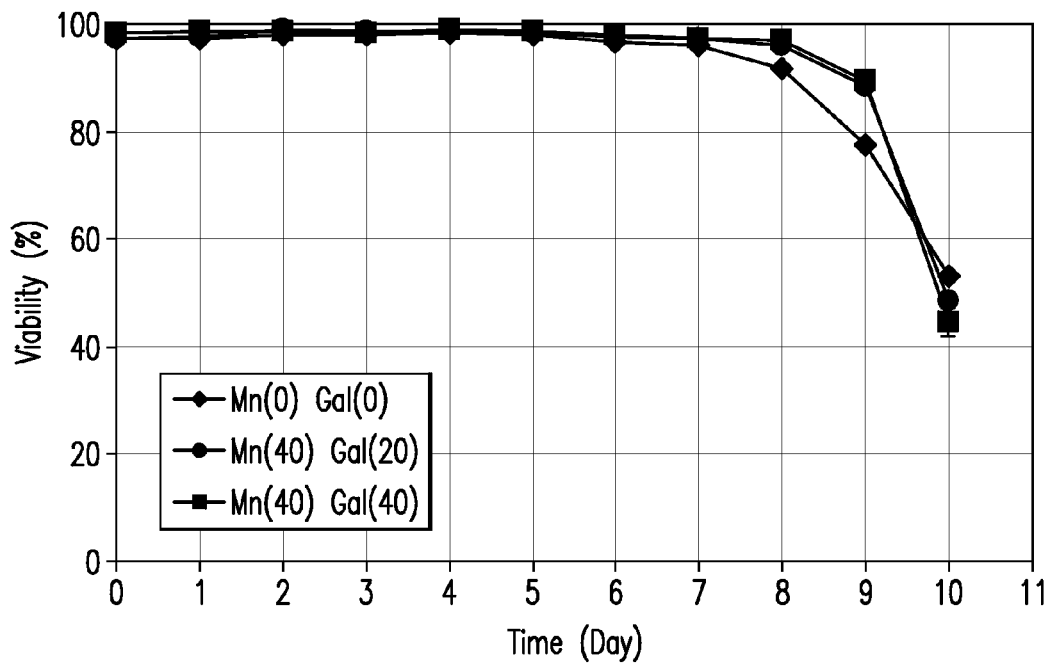
Figure 2C:
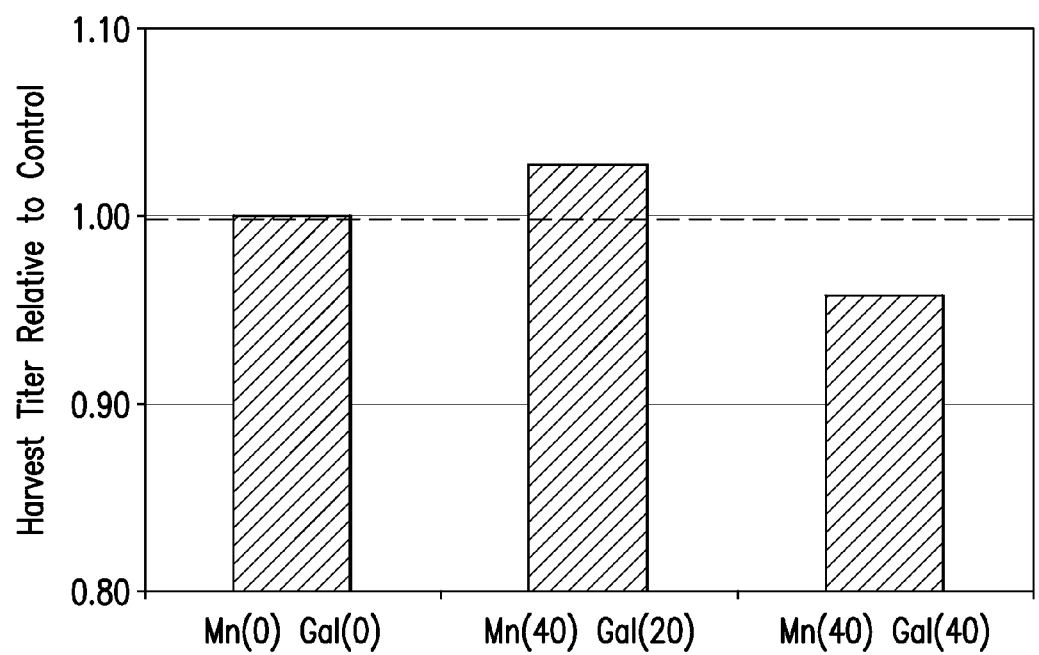

For the shake flasks experiments, cell growth and viability profiles of cultures in production media supplemented with galactose in the 0 to 100 mM concentration range and/or manganese chloride up to 80 μM concentration were comparable to control cultures without manganese and/or galactose added (FIGS. 1A, 1B). Cultures grown in media supplemented with manganese chloride at 100 μM concentration and galactose concentrations in the 0 to 100 mM range experienced growth lag and decreased viability for the first 4 production days, likely due to toxic effects of manganese at this concentration. However, toxicity effects were overcome after production day 4. Harvest titer for most experimental conditions was 3% to 14% higher than the average harvest titer for the control cultures (FIG. 1C). All three control cultures had comparable growth profiles and productivity. For the bioreactors fed-batch experiment, culture growth, viability profiles, and harvest titer were comparable for all conditions (FIGS. 2A, 2B, 2C).

6.1.4. Oligosaccharide Analysis

In this example, the modulation of galactosylation with the addition of manganese chloride and/or galactose to chemically defined media GIA-1 was explored using the adalimumab-producing CHO cell line utilized in Example 3, but adapted to GIA-1 media.

6.1.4.1. Batch Shake Flask Study

For the shake flask study, the addition of manganese chloride alone within the range of 0 to 100 μM to production CDM GIA-1 decreased the NGA2F+NGA2F-GlcNac sum in a concentration dependent manner and increased the NA1F+NA2F sum by approximately the same percentage. A maximum change of 9% in the NGA2F+NGA2F-GlcNac and 8% in the NA1F+NA2F oligosaccharides was observed with the addition of 100 μM manganese chloride (FIG. 3). Manganese doses greater than 100 μM were not explored further due to cytotoxicity effects. Similarly, a concentration dependent decrease in the NGA2F+NGA2F-GlcNac sum and a corresponding increase in the NA1F+NA2F sum were observed with the addition of galactose alone in the range of 0 to 100 mM to production CDM GIA-1. A maximum change of 7% in the NGA2F+NGA2F-GlcNac and the NA1F+NA2F oligosaccharides was observed with the addition of 100 mM galactose.

The effect on modulation of galactosylation of adalimumab in CDM GIA-1 with the combined addition of manganese chloride and galactose was synergistic. Combined addition of manganese chloride and galactose decreased the NGA2F+NGA2F-GlcNac sum and increased the NA1F+NA2F sum by a larger percentage than by adding manganese or galactose alone and summing up their individual effects (FIGS. 4 and 5). For example, addition of 40 μM manganese chloride alone reduced the NGA2F+NGA2F-GlcNac sum by 6%, and addition of 40 mM galactose alone decreased the NGA2F+NGA2F-GlcNac sum by 6%. However, the combined addition of manganese chloride and galactose at these same concentrations (i.e. 40 μM manganese+40 mM galactose) led to an 18% reduction in the NGA2F+NGA2F-GlcNac sum, 6% higher than their combined individual contributions to the reduction of the NGA2F+NGA2F-GlcNac sum. We define this effect as being synergistic and maintain this definition throughout the invention. A maximum decrease compared to the control condition of 26% in the NGA2F+NGA2F-GlcNac sum was observed with the combined addition of 100 μM manganese chloride and 100 mM galactose.

6.1.4.2. Fed-Batch Bioreactor Study

For the fed-batch 3 L bioreactors study, two manganese chloride and galactose combinations were studied and we show that the decrease in the NGA2F+NGA2F-GlcNac and the corresponding increase in the NA1F+NA2F oligosaccharides was scale (1.5 L vs. 200 mL) and process independent (fed-batch in controlled bioreactor environment vs. batch in shake flasks). Combined addition of 40 μM manganese chloride and 20 mM galactose to both production basal CDM GIA-1 and feed CDM JCL-5 decreased the NGA2F+NGA2F-GlcNac sum by 26% and increased the NA2F+NA2F sum by 27% compared to the control cultures (FIG. 6). A further increase in the galactose concentration to 40 mM in addition to manganese supplementation at 40 μM concentration resulted in an additional 3% decrease in the NGA2F+NGA2F-GlcNac sum, and a corresponding 3% increase in the NA1F+NA2F sum.

6.2. Example 2

6.2.1. Materials & Methods

In the study summarized in this example, we investigated the effects on product quality attributes resulting from the addition of manganese chloride and/or galactose to the chemically defined media Thermo Scientific HyClone CDM4CHO using the adalimumab-producing CHO cell line used in Example 1 further adapted to HyClone media.

Growth and production media for the adalimumab-producing CHO cell line were prepared using Thermo Scientific HyClone chemically defined media CDM4CHO without L-glutamine (Catalogue #SH30558.02). Production media was supplemented with Manganese (II) Chloride (Sigma M1787—100 mL; 1.0 M±0.1 M) and D(+)Galactose (Sigma G5388-1 kg) according to the experimental design described in Table 3. All media were filtered through Corning 0.5 L or 1 L (0.22 μm PES) filter systems and stored at 4° C. until use.

Upon thaw, cells were adapted to and expanded in HyClone CDM4CHO media for 5 (2 to 3 day each) passages in a combination of 250 mL, 500 mL, and 1000 mL Corning vented non-baffled shake flasks. Production cultures were initiated in duplicate 500 mL Corning vented non-baffled shake flasks (200 mL working volume) at an initial VCD of approximately 0.5×106 cells/mL. Cultures were maintained on orbital shakers at 110 RPM in a dry incubator at 35° C. and 5% $CO_2$. A glucose solution (1.25% (v/v) of 40% solution) was fed when the media glucose concentration fell below 3 g/L.

6.2.2. Experimental Design

As detailed in Table 3, manganese chloride was supplemented at the following concentrations in production media: 0, 10, 20, and 40 μM. Galactose was supplemented at the following levels in production media: 0, 10, 20, and 100 mM. Production media for the control cultures was not supplemented with manganese chloride or galactose.

TABLE 3

Experimental design for Example 2

| Manganese (μM) | Galactose (mM) | ID |
|---|---|---|
| 0 | 0 | Mn(0) Gal(0) |
| 0 | 10 | Mn(0) Gal(10) |
| 0 | 20 | Mn(0) Gal(20) |
| 0 | 40 | Mn(0) Gal(40) |
| 10 | 0 | Mn(10) Gal (0) |
| 20 | 0 | Mn(20) Gal(0) |
| 40 | 0 | Mn(40) Gal(0) |
| 10 | 10 | Mn(10) Gal(10) |
| 20 | 20 | Mn(20) Gal(20) |
| 40 | 40 | Mn(40) Gal(40) |

6.2.3. Culture Growth & Productivity

Figure 7A:
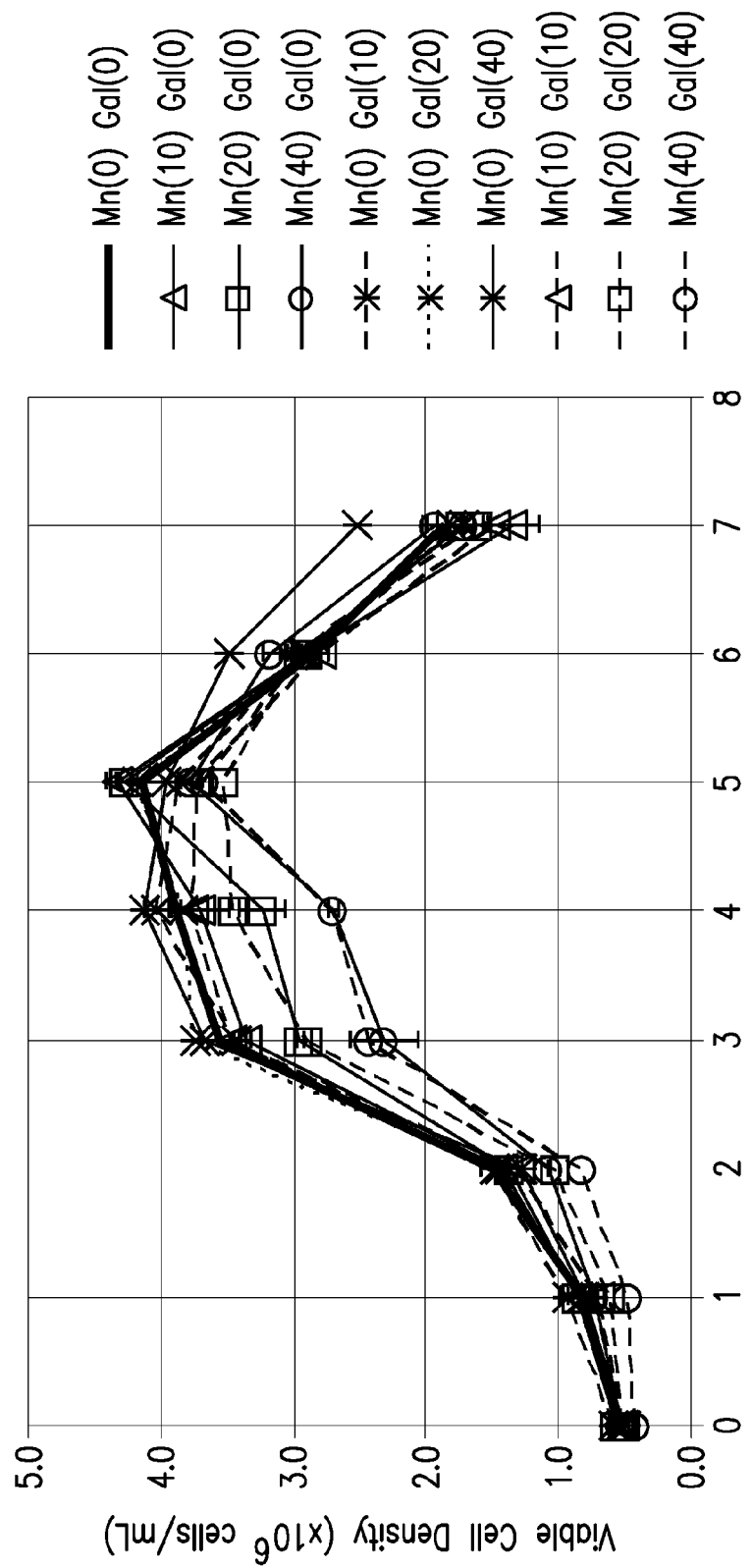
Figure 7B:
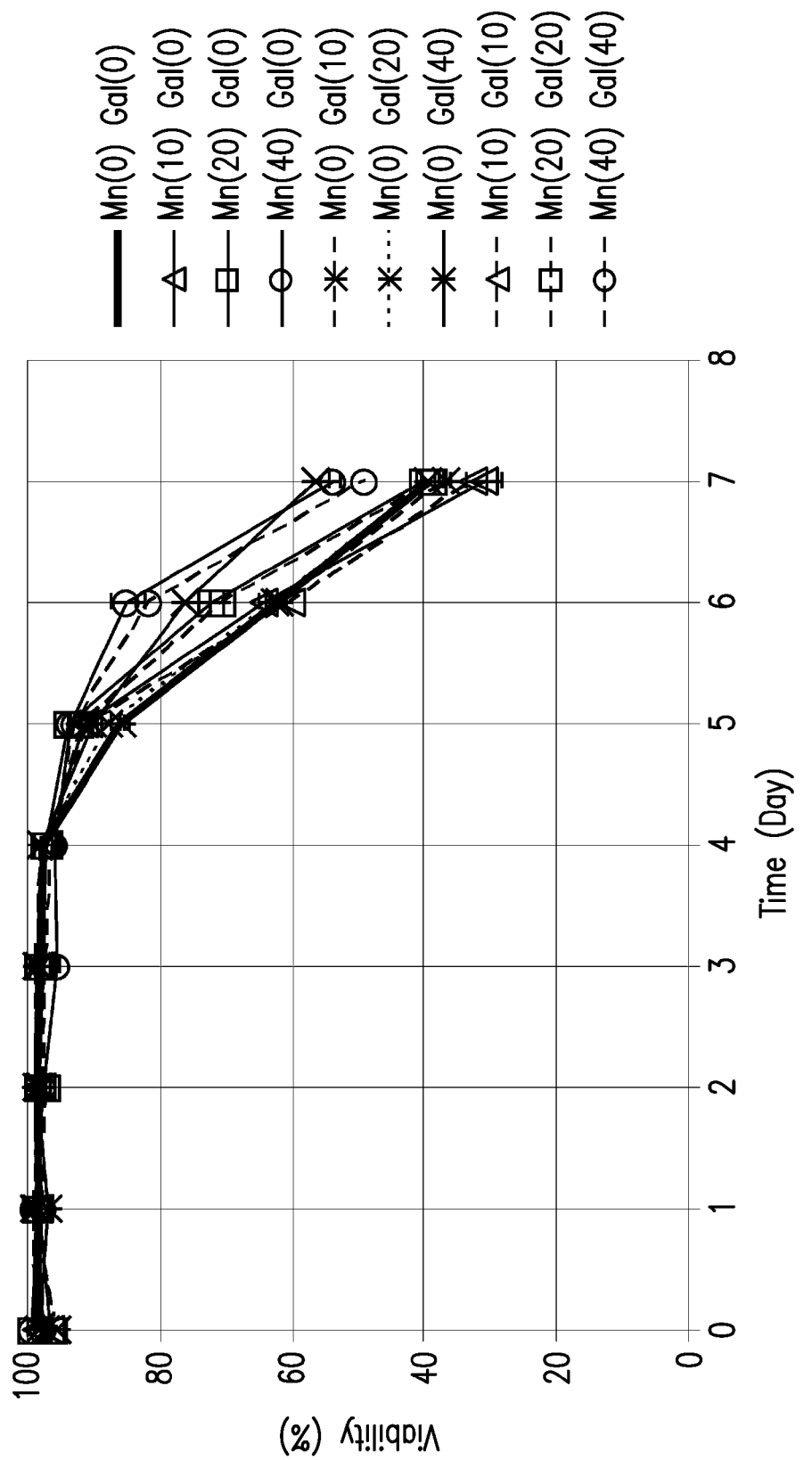

Cell growth and viability profiles of cultures in production HyClone CDM4CHO supplemented with galactose in the 0 to 40 mM concentration range and/or manganese chloride up to 10 μM concentration were comparable to the control cultures without manganese and/or galactose added (FIGS. 7A, 7B). Increasing the concentration of manganese chloride in HyClone CDM4CHO production media to 20 μM or 40 μM slowed down culture growth. Manganese doses greater than 40 μM were not explored further due to the observed growth inhibition effects. Harvest titer for all conditions was comparable to the control (data not shown).

6.2.4. Oligosaccharide Analysis

In this example, the modulation of galactosylation with the addition of manganese chloride and/or galactose to the commercially available HyClone CDM4CHO was explored using the adalimumab-producing CHO cell line used Example 1 further adapted to HyClone media.

The addition of manganese chloride alone within the range of 0 to 40 μM to production CDM HyClone CDM4CHO decreased the NGA2F+NGA2F-GlcNac sum by a maximum of 5% in a concentration dependent manner (FIG. 8). A comparable maximum increase of 4% in the NA1F+NA2F sum was achieved. Addition of galactose alone up to a maximum concentration of 40 mM yielded a 6% maximum decrease in the NGA2F+NGA2F-GlcNac sum and a corresponding 6% increase in the NA1F+NA2F sum.

An additive effect was observed in cultures supplemented with both manganese chloride and galactose. The combined addition of manganese chloride and galactose decreased the NGA2F+NGA2F-GlcNac sum and increased the NA1F+NA2F sum by a comparable percentage as when manganese or galactose were added alone and their individual effects were summed up (FIG. 9). For example, addition of 40 μM manganese chloride alone reduced the NGA2F+NGA2F-GlcNac sum by 5%, and addition of 40 mM galactose alone decreased the NGA2F+NGA2F-GlcNac sum by 6%. The combined addition of manganese chloride and galactose at these same concentrations (i.e. 40 μM manganese+40 mM galactose) led to a 12% reduction in the NGA2F+NGA2F-GlcNac sum. We define this effect as being additive and maintain this definition throughout the invention.

The highest percentage decrease in the NGA2F+NGA2F-GlcNac sum of 12% and the corresponding 11% increase in the NA1F+NA2F sum was observed for the culture supplemented with 40 μM manganese chloride and 40 mM galactose.

6.3. Example 3

6.3.1. Materials & Methods

In the study summarized in this example, we investigated the effects on product quality attributes resulting from the addition of manganese chloride and/or galactose to a hydrolysate-based media (proprietary formulation) in an adalimumab-producing CHO cell line.

Growth and production media for the adalimumab-producing CHO cell line were prepared using yeast and soy hydrolysates according to a proprietary formulation. Production media was supplemented with Manganese (II) Chloride (Sigma M1787—100 mL; 1.0 M±0.1 M) and D(+)Galactose (Sigma G5388—1 kg) according to the experimental design described in Table 4. All media were filtered through Corning 0.5 L or 1 L filter systems (0.22 μm PES) and stored at 4° C. until use.

Upon thaw, cells were expanded for 9 (2 to 3 day each) passages in a combination of 250 mL, 500 mL, and 1000 mL Corning vented non-baffled shake flasks. Production cultures were initiated in duplicate 500 mL Corning vented non-baffled shake flasks (200 mL working volume) at an initial VCD of approximately 0.5×106 cells/mL. Cultures were maintained on orbital shakers at 110 RPM in a dry incubator at 35° C. and 5% $CO_2$. A glucose solution (1.25% (v/v) of 40% solution) was fed when the media glucose concentration fell below 3 g/L.

6.3.2. Experimental Design

As detailed in Table 4, manganese chloride was supplemented at the following concentrations in production media: 0, 10, 20, and 40 μM. Galactose was supplemented at the following levels in production media: 0, 10, 20, and 40 mM. Production media for the control cultures was not supplemented with manganese chloride or galactose.

TABLE 4

Experimental design for Example 3

| Manganese (μM) | Galactose (mM) | ID |
|---|---|---|
| 0 | 0 | Mn(0) Gal(0) |
| 0 | 10 | Mn(0) Gal(10) |
| 0 | 20 | Mn(0) Gal(20) |
| 0 | 40 | Mn(0) Gal(40) |
| 10 | 0 | Mn(10) Gal (0) |
| 20 | 0 | Mn(20) Gal(0) |
| 40 | 0 | Mn(40) Gal(0) |
| 10 | 10 | Mn(10) Gal(10) |
| 20 | 20 | Mn(20) Gal(20) |
| 40 | 40 | Mn(40) Gal(40) |

6.3.3. Culture Growth & Productivity

Figure 10A:
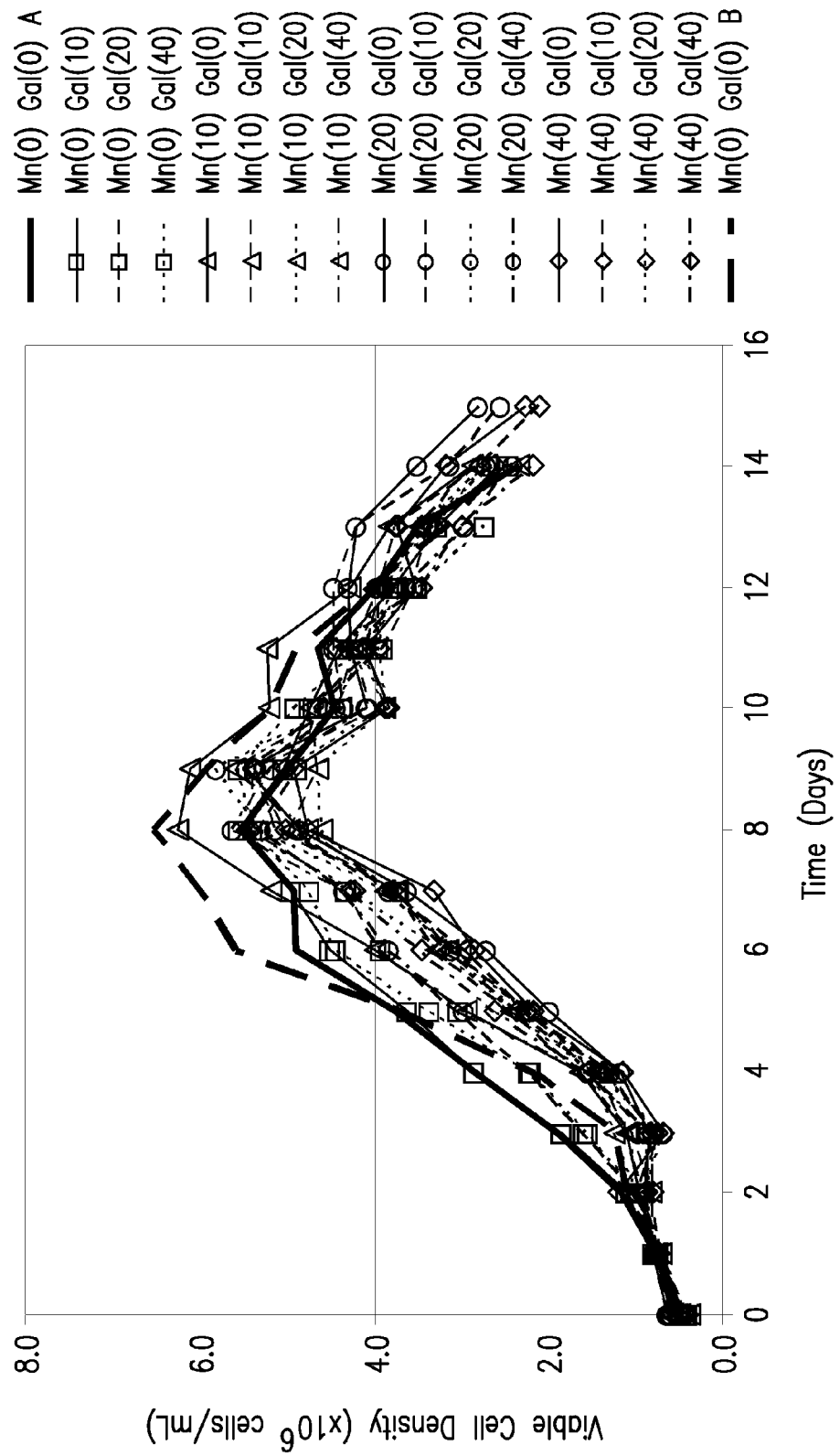
Figure 10B:
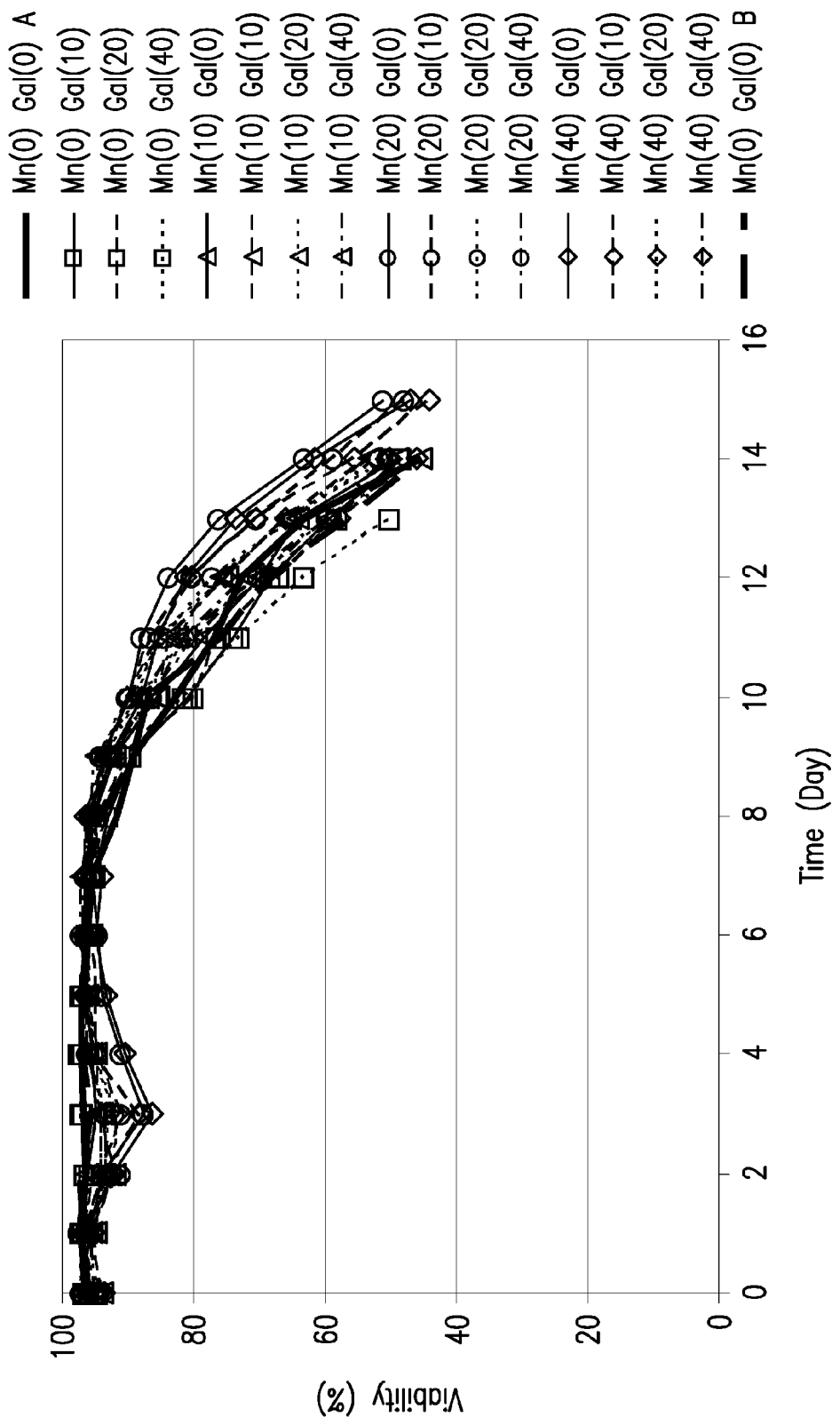

Cell growth of most cultures in the hydrolysate-based media supplemented with galactose in the 0 to 40 mM concentration range and/or manganese chloride in the 0 to 40 μM concentration was slower compared to the control cultures without manganese or galactose added (FIG. 10A). However, all cultures reached a comparable peak viable cell density. Some cultures supplemented with 20 μM or 40 μM manganese chloride showed decreased viability by day 3 of production culture, but recovered as the cultures progressed (FIG. 10B). The culture supplemented with 10 μM manganese chloride was studied with a second control condition (B) in a separate experiment. Both these cultures grew to slightly higher maximum VCD compared to all other cultures, however results were within historical variation. Harvest titer for all conditions was comparable to the control (data not shown).

6.3.4. Oligosaccharide Analysis

In this example, the modulation of galactosylation by the addition of manganese chloride and/or galactose to a hydrolysate-based media was explored using an adalimumab-producing CHO cell line in shake flasks.

The addition of manganese chloride alone within the range of 0 to 40 μM to hydrolysate-based production media decreased the NGA2F+NGA2F-GlcNac sum by approximately 1%, a change that is within the oligosaccharide assay variability (FIG. 11). The addition of galactose alone up to a maximum concentration of 40 mM yielded a maximum decrease of 4% in the NGA2F+NGA2F-GlcNac sum and a corresponding 4% maximum increase in the NA1F+NA2F sum.

The oligosaccharide profile changes achieved with the addition of galactose alone are comparable to the changes recorded when combinations of galactose and manganese chloride were added to the hydrolysate-based media. The combined addition of manganese chloride ranging from 0 to 40 μM and galactose ranging from 0 to 40 mM to hydrolysate-based media led to an approximate 5% maximum decrease in the NGA2F+NGA2F-GlcNac sum and a corresponding 3% increase in the NA1F+NA2F sum (FIG. 12). The highest percentage decrease of 5% in the NGA2F+NGA2F-GlcNac sum and the corresponding 4% increase in the NA1F+NA2F sum was observed for the culture supplemented with 40 mM galactose and either 20 μM or 40 μM manganese chloride.

6.4. Example 4

6.4.1. Materials & Methods

In the study summarized in this example, we investigated the effects on product quality attributes resulting from the addition of manganese chloride and/or galactose to chemically defined Life Technologies Gibco GIA-1 media using a different adalimumab producing CHO cell line than in Examples 1, 2, and 3, named CHO cell line #2.

Growth and production media for the adalimumab-producing CHO cell line #2 were prepared using a proprietary Life Technologies Gibco chemically defined media, GIA-1. Production media only was supplemented with Manganese (II) Chloride (Sigma M1787—100 mL; 1.0 M±0.1 M) and D(+) Galactose (Sigma G5388—1 kg) according to the experimental design described in Table 5. All media were filtered through Corning 0.5 L or 1 L filter systems (0.22 μm PES) and stored at 4° C. until use.

Upon thaw, cells were expanded for 5 to 8 (2 to 3 day each) passages in a combination of 250 mL, 500 mL, and 1000 mL Corning vented non-baffled shake flasks. Production cultures were initiated in duplicate 500 mL Corning vented non-baffled shake flasks (200 mL working volume) at an initial VCD of approximately 0.5×106 cells/mL. Cultures were maintained on orbital shakers at 180 RPM in a dry incubator at 35° C. and 5% $CO_2$. A glucose solution (1.25% (v/v) of 40% solution) was fed when the media glucose concentration fell below 3 g/L.

6.4.2. Experimental Design

As detailed in Table 5, manganese chloride was supplemented at the following concentrations in production media: 0, 10, 20, and 40 μM. Galactose was supplemented at the following levels in production media: 0, 10, and 20 mM. Production media for the control cultures was not supplemented with manganese chloride or galactose. This study was run in 2 blocks.

TABLE 5

Experimental design for Example 4

| | Manganese (μM) | Galactose (mM) | ID |
|---|---|---|---|
| Block I | 0 | 0 | Mn(0) Gal(0) |
| | 20 | 0 | Mn(20) Gal(0) |
| | 10 | 10 | Mn(10) Gal(10) |
| | 20 | 20 | Mn(20) Gal(20) |
| | 40 | 20 | Mn(40) Gal(20) |
| Block II | 0 | 0 | Mn(0) Gal(0) |
| | 0 | 10 | Mn(0) Gal(10) |
| | 0 | 20 | Mn(0) Gal (20) |
| | 10 | 0 | Mn(10) Gal(0) |

6.4.3. Culture Growth & Productivity

Figure 13A:
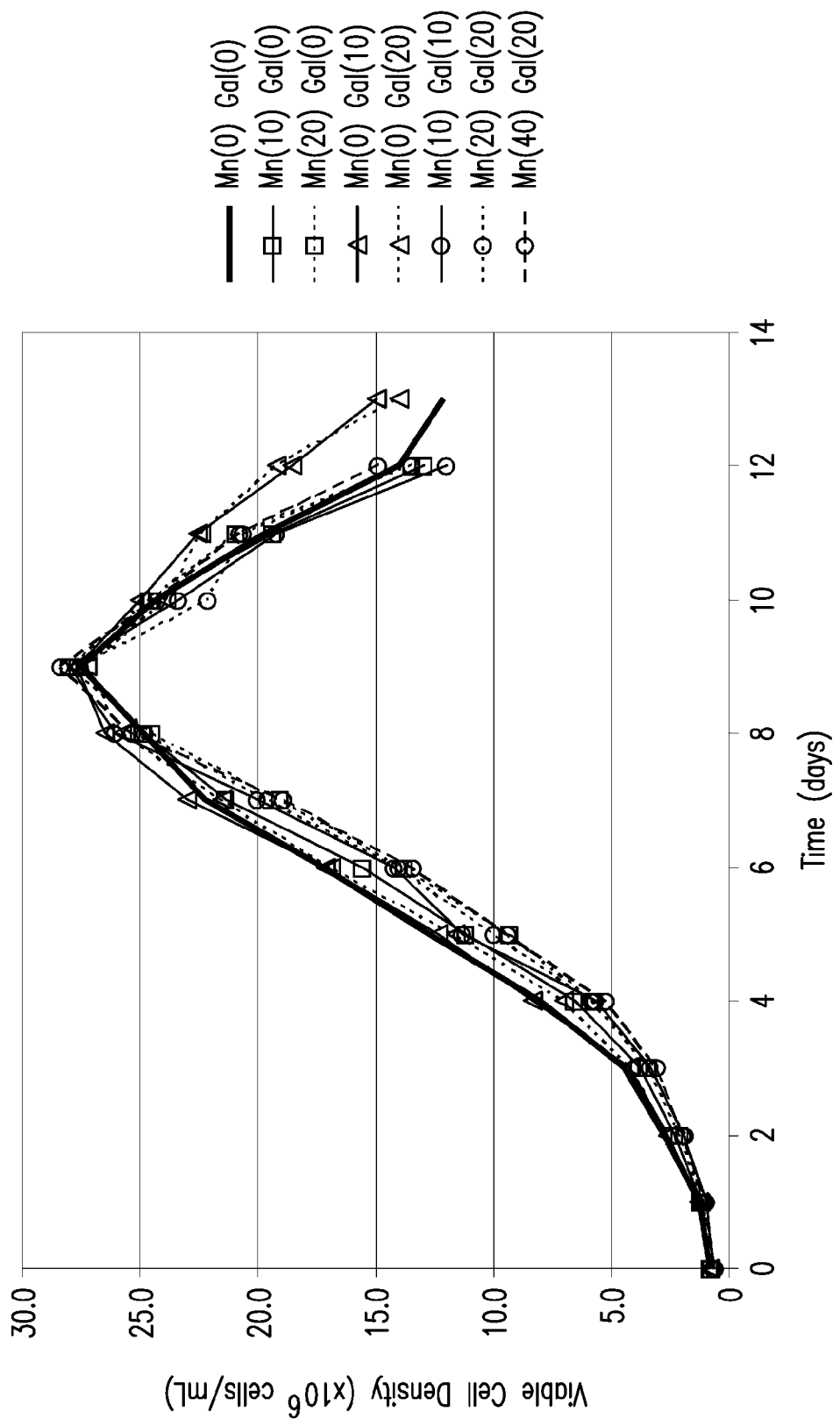
Figure 13B:
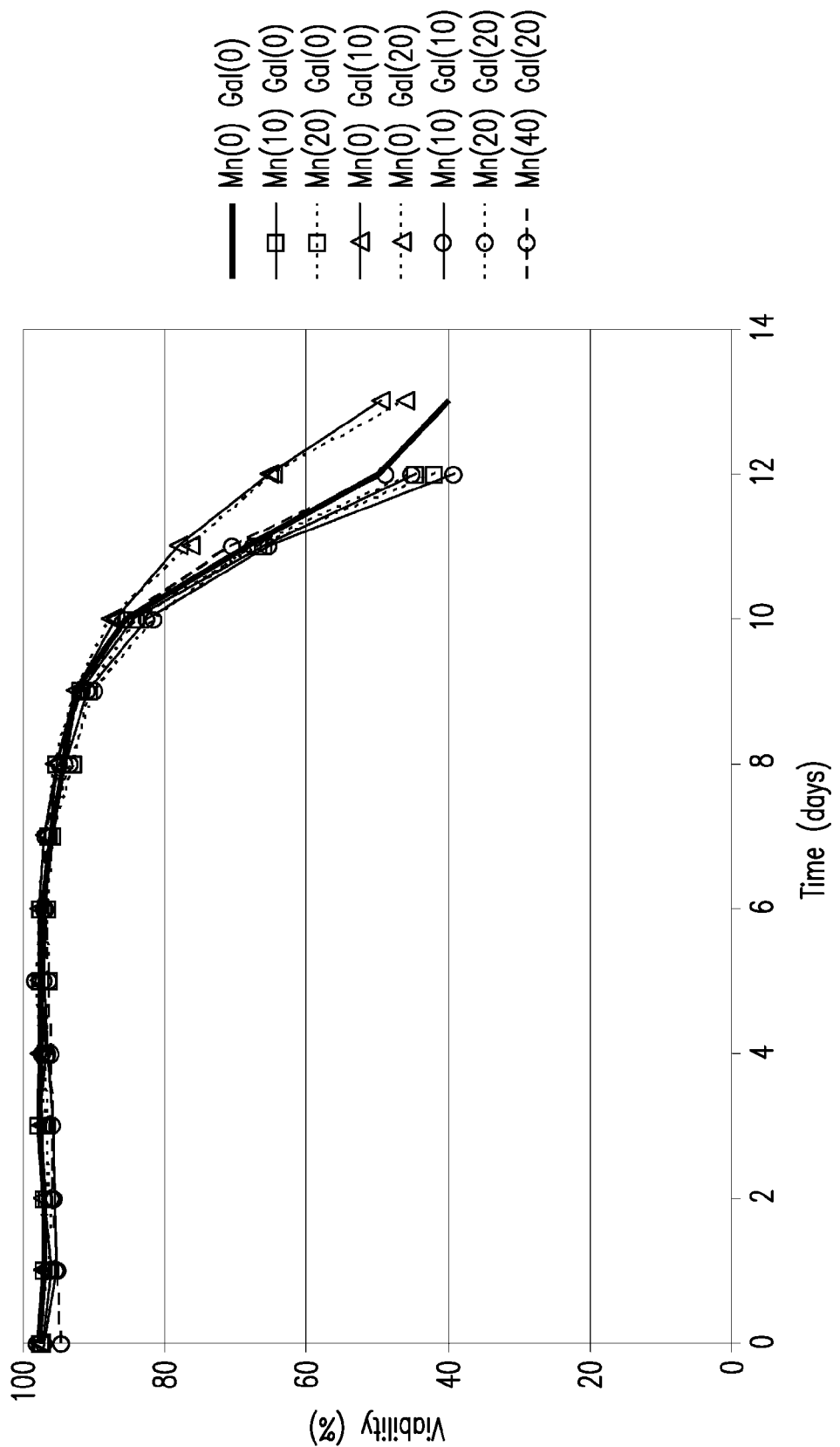

Culture growth, viability profiles, and harvest titer of cultures in production CDM GIA-1 supplemented with galactose in the 0 to 20 mM concentration range and/or manganese chloride in the 0 to 40 μM concentration range were comparable to the control cultures without manganese or galactose added (FIGS. 13A, 13B; harvest titer data not shown).

6.4.4. Oligosaccharide Analysis

In this example, the modulation of galactosylation by the addition of manganese chloride and/or galactose to chemically defined GIA-1 media was explored using the adalimumab-producing CHO cell line #2.

The addition of manganese chloride alone within the range of 0 to 20 μM to production CDM GIA-1 decreased the NGA2F+NGA2F-GlcNac sum in a concentration dependent manner and increased the NA1F+NA2F sum by approximately the same percentage. A maximum decrease of 22% in the NGA2F+NGA2F-GlcNac sum and a maximum corresponding increase of 23% in the NA1F+NA2F sum was observed with the addition of 20 μM manganese chloride (FIG. 14). Similarly, a concentration dependent decrease in the NGA2F+NGA2F-GlcNac sum and a corresponding increase in the NA1F+NA2F sum was observed with the addition of galactose alone in the range of 0 to 20 mM. A maximum decrease of 9% in the NGA2F+NGA2F-GlcNac sum and a corresponding maximum increase of 10% in the NA1F+NA2F sum was observed with the addition of 20 mM galactose.

An additive effect was observed for the oligosaccharide profiles of adalimumab produced in cultures supplemented with the combined addition of manganese chloride and galactose to GIA-1 media (FIG. 15). For example, addition of 10 μM manganese chloride alone reduced the NGA2F+NGA2F-GlcNac sum by 18%, and addition of 10 mM galactose alone decreased the NGA2F+NGA2F-GlcNac sum by 6%. The combined addition of manganese chloride and galactose at these same concentrations led to a 24% reduction in the NGA2F+NGA2F-GlcNac sum. The highest percentage decrease of 35% in the NGA2F+NGA2F-GlcNac sum and the corresponding increase of 37% in the NA1F+NA2F sum were observed for the culture supplemented with 40 μM manganese chloride and 20 mM galactose.

6.5. Example 5

6.5.1. Materials & Methods

In the study summarized in this example, we investigated the effects on product quality attributes resulting from the addition of manganese chloride and/or galactose to chemically defined Life Technologies Gibco GIA-1 media using a different adalimumab-producing CHO cell line than in Examples 1, 2, 3, and 4, named CHO cell line #3.

Growth and production media for the adalimumab-producing CHO cell line #3 were prepared using the proprietary Life Technologies Gibco chemically defined media, GIA-1. Basal production and feed media were supplemented with Manganese (II) Chloride (Sigma M3634—100 g) and D(+)Galactose (Sigma G5388—1 kg) according to the experimental design described in Table 6.

Upon thaw, cells were expanded in Corning vented non-baffled shake flasks maintained on orbital shakers at 140 RPM, and in 10 L cell bags (2 L working volume) maintained at 25 RPM, 7° angle, and 0.25 SLPM airflow in a dry incubator at 36° C. and 5% $CO_2$. Production cultures were initiated in 3 L bioreactors (1.4 L initial working volume) at 36° C., 30% dissolved oxygen, 200 RPM, and pH 6.9±0.2. A fixed split ratio of cells to media of 1:6.7 was utilized to initiate the production stage cultures. A temperature shift was performed when the culture VCD reached a value higher than 5×106 cells/mL. The chemically-defined feed from Life Technologies Gibco JCL-5 was added as follows: 4% (v/v)—day 2, 6%—day 4, 8%—day 6, 10%—day 8, and 10%—day 10. Additional 400 g/L glucose was added to the reactor cultures as needed to ensure glucose levels did not deplete. Bioreactors were harvested at a viability of approximately 50% or on production day 17, whichever condition occurred first.

6.5.2. Experimental Design

As detailed in Table 6, manganese chloride was supplemented at the following concentrations in both production and feed media: 0, 0.1, 0.2, 0.5, and 1.0 μM. Galactose was supplemented at 0 and 30 mM concentrations in both production and feed media. In addition, a combined manganese chloride and galactose supplementation strategy was utilized for the production basal and feed media at either 0.2 or 0.5 μM manganese chloride plus 30 mM galactose. Basal and feed media for the control cultures were not supplemented with manganese chloride or galactose.

TABLE 6

Experimental design for Example 5

| Manganese (μM) | Galactose (mM) | ID |
|---|---|---|
| 0 | 0 | Mn(0) Gal(0) |
| 0.1 | 0 | Mn(0.1) Gal(0) |
| 0.2 | 0 | Mn(0.2) Gal(0) |
| 0.5 | 0 | Mn(0.5) Gal(0) |
| 1.0 | 0 | Mn(1.0) Gal(0) |
| 0 | 30 | Mn(0) Gal(30) |
| 0.2 | 30 | Mn(0.2) Gal(30) |
| 0.5 | 30 | Mn(0.5) Gal(30) |

6.5.3. Culture Growth & Productivity

Figure 16A:
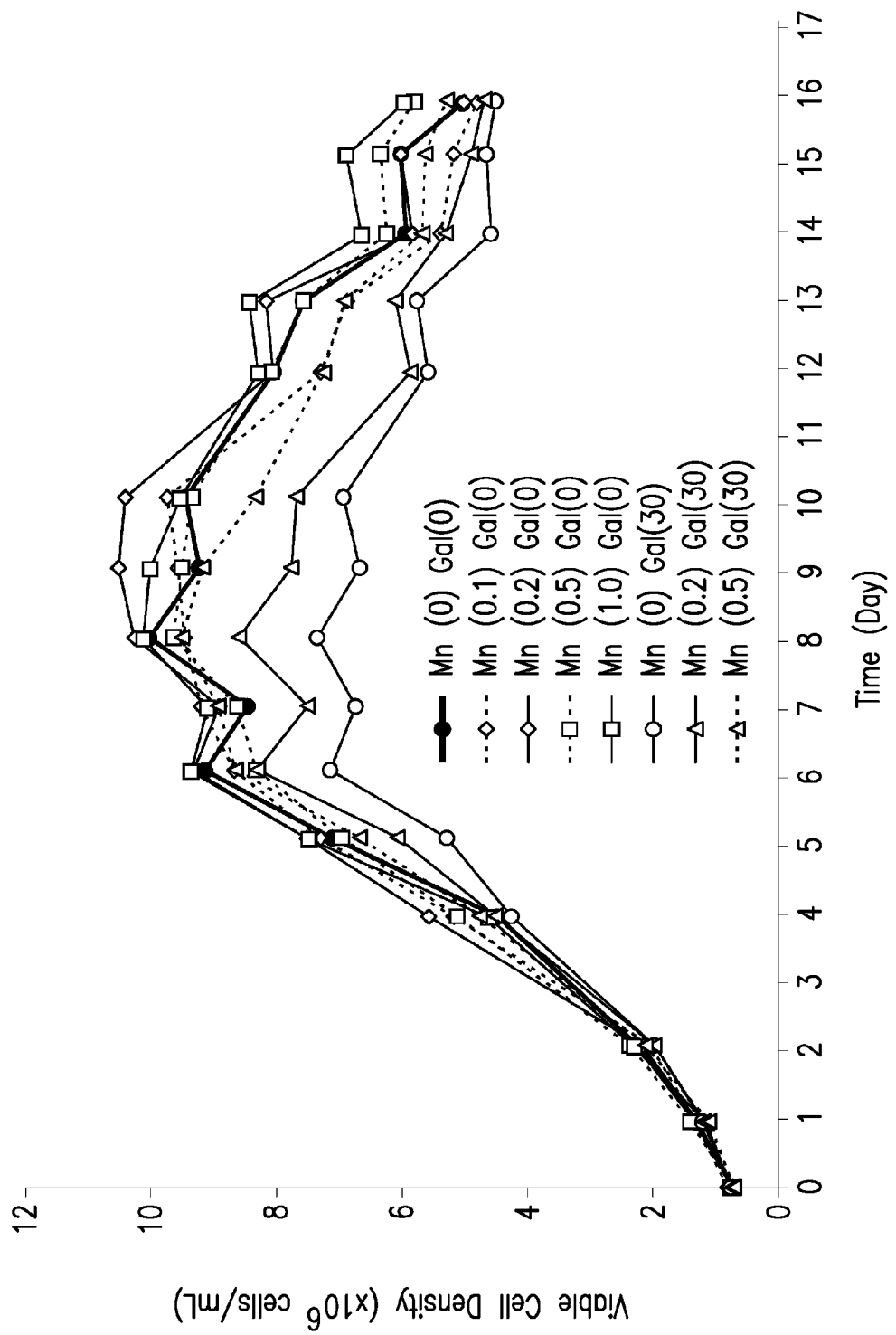
Figure 16B:
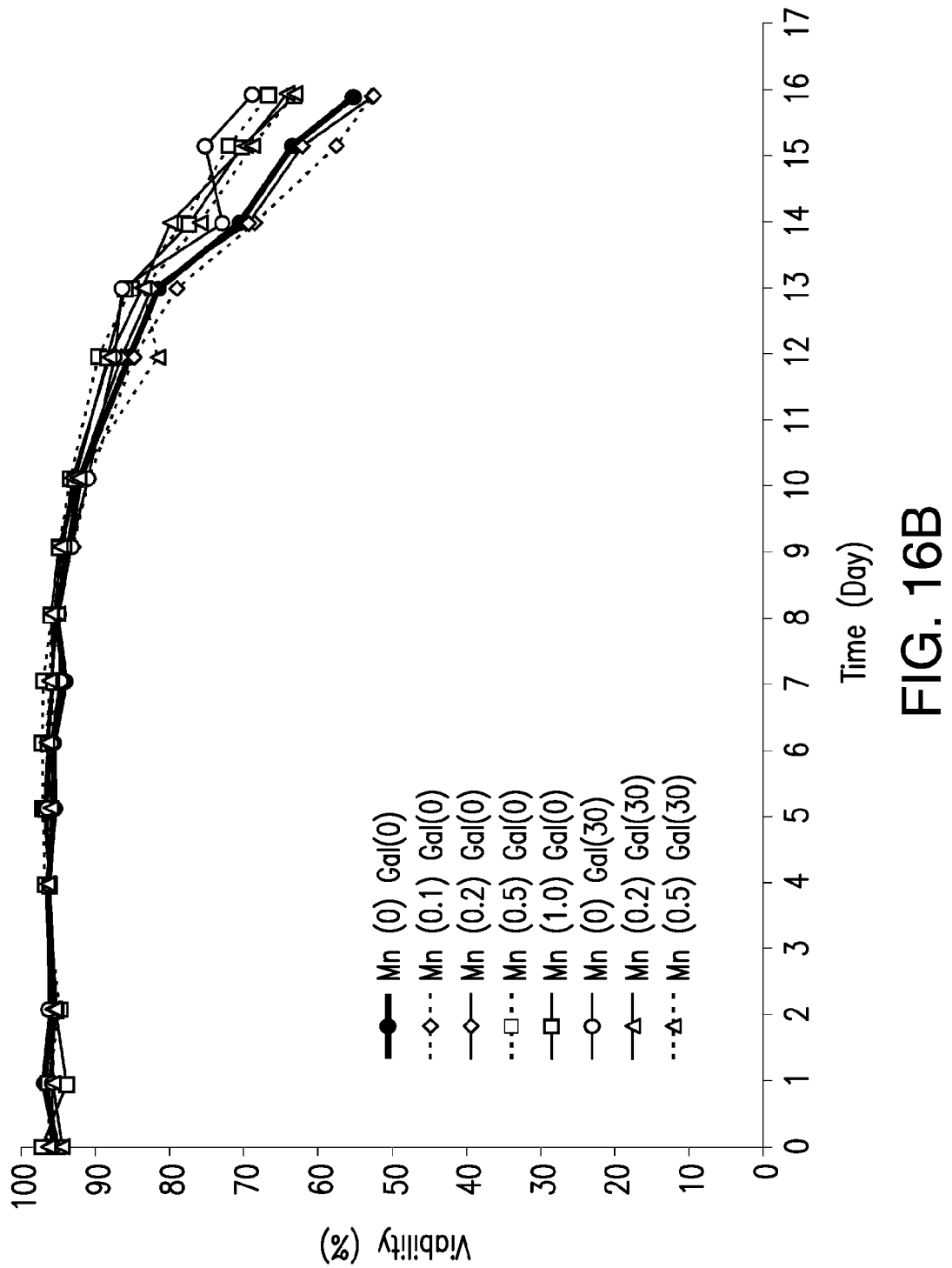
Figure 16C:
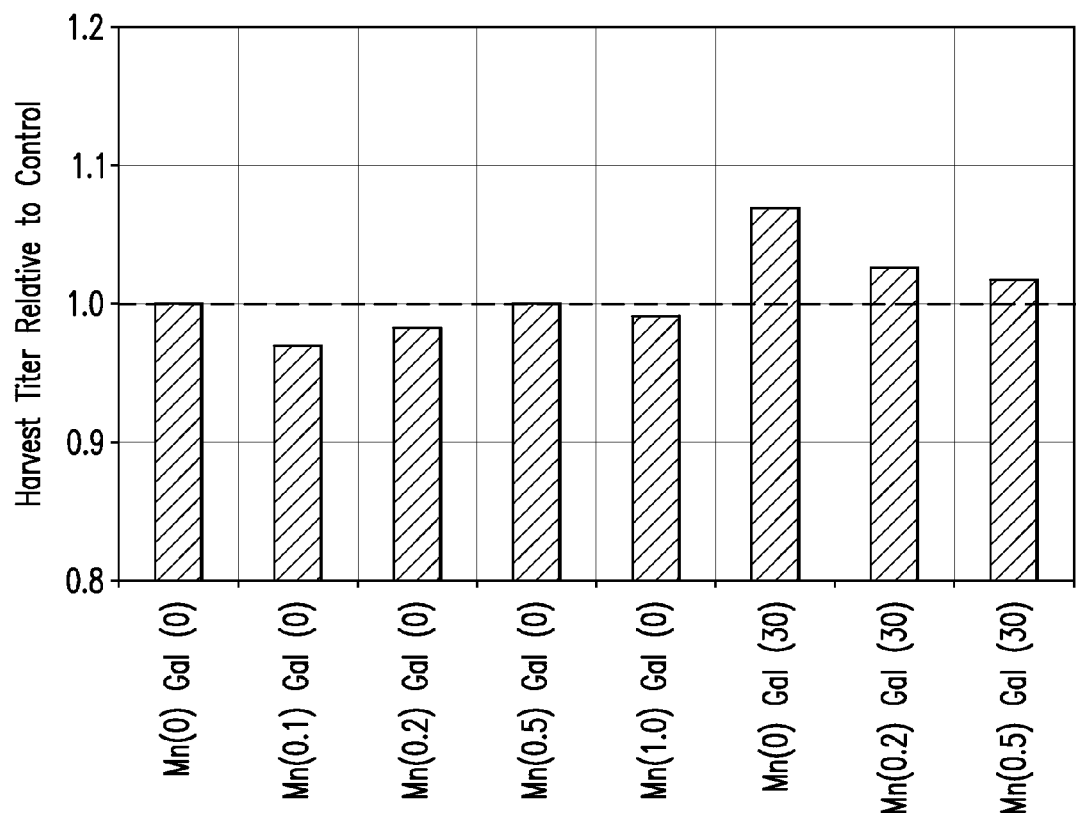

Growth profiles of most cultures supplemented with manganese chloride and/or galactose were comparable to the control culture except for the cultures supplemented with 30 mM galactose alone or in combination with 0.2 μM manganese chloride which grew slower and reached a lower peak VCD (FIG. 16A). However, the culture supplemented with 0.5 μM manganese chloride and 30 mM galactose had a growth profile comparable to the control culture indicating that neither manganese chloride nor galactose at the concentrations studied are detrimental to culture growth. Viability profiles and harvest titer were comparable to the control condition (FIGS. 16B, 16C).

6.5.4. Oligosaccharide Analysis

In this example, the modulation of galactosylation with the addition of manganese chloride and/or galactose to chemically defined media GIA-1 was explored using the adalimumab-producing CHO cell line #3.

The addition of manganese chloride alone within the range of 0 to 1 μM to production CDM GIA-1 decreased the NGA2F+NGA2F-GlcNac sum in a concentration dependent manner and increased the NA1F+NA2F sum by approximately the same percentage. A maximum decrease of 26% in the NGA2F+NGA2F-GlcNac and a corresponding increase of 28% in the NA1F+NA2F oligosaccharides were observed with the addition of 1 μM manganese chloride (FIG. 17). The addition of galactose alone at 30 mM concentration to production CDM GIA-1 decreased the NGA2F+NGA2F-GlcNac sum by 4% and increased the NA1F+NA2F sum by 3%.

When manganese chloride and galactose were supplemented together into the production basal and feed media, the results demonstrated a synergistic benefit towards the decrease in the NGA2F+NGA2F-GlcNAc and the increase in the NA1F+NA2F oligosaccharides which is consistent with the results demonstrated in Example 1 (FIG. 18). For example, at 0.2 μM manganese chloride plus 30 mM galactose the observed 25% decrease in the NGA2F+NGA2F-GlcNAc sum was 6% more than the sum of the decrease observed with the addition of 0.2 μM manganese chloride alone (15%) and that of 30 mM galactose alone (4%). Similarly the resulting 24% increase in the NA1F+NA2F sum was more than the sum of the increase observed with the addition of 0.2 μM manganese chloride alone (16%) and that of 30 mM galactose alone (3%). The combined supplementation of 0.5 μM manganese chloride+30 mM galactose also demonstrated a synergistic effect on the galactosylation profile of adalimumab produced in the CHO cell line #3. A maximum decrease compared to the control condition of 34% in the NGA2F+NGA2F-GlcNac and a corresponding 34% maximum increase in the NA1F+NA2F oligosaccharides was observed with the combined addition of 0.5 μM manganese chloride and 30 mM galactose to chemically defined GIA-1 media.

6.6. Example 6

6.6.1. Materials & Methods

In the study summarized in this example, we investigated the effects on product quality attributes resulting from the addition of manganese chloride and/or galactose to chemically defined Life Technologies Gibco PFBM-3 basal medium and PFFM-4 feed medium (proprietary formulation) using an adalimumab-producing NSO cell line in a fed-batch process in shake flasks.

Growth and production media for the adalimumab-producing NSO cell line were prepared using a proprietary Life Technologies Gibco chemically defined media, PFBM-3 basal medium plus PFFM-4 feed medium. Production and feed media were supplemented with Manganese (II) Chloride (Sigma M1787—100 mL; 1.0 M±0.1 M) and D(+)Galactose (Sigma G5388-1 kg) according to the experimental design described in Table 7.

Upon thaw, cells were expanded for 3 to 5 (2 days each) passages in a combination of 250 mL, 500 mL, 1 L, 2 L and 3 L Corning vented non-baffled shake flasks. Production cultures were initiated in single 1 L Corning vented non-baffled shake flasks (240 mL initial working volume) at an initial VCD of approximately $2.5 \times 10^5$ cells/mL. Cultures were maintained on orbital shakers at 100 RPM in a dry incubator at 37° C. and 5% $CO_2$. The shake flask study was run in a fed-batch mode and the culture was fed PFFM-4 as follows: 24 mL—day 2, 28.8 mL—day 4, 28.8 mL—day 6, and 28.8 mL—day 8.

Samples were collected every 2 days and measured for cell density and viability using a Cedex cell counter. Retention samples for titer analysis via Poros A method were collected daily beginning on Day 8 by centrifugation at 2,000 g for 10 min and then filtered through 0.2 um PVDF syringe filter. The cultures were harvested on production day 10. The entire culture was collected, chilled on ice to approximately 0° C. for 1.5 hours, the cells and debris flocculated at pH 5.0 by the addition of 1M citric acid and held for 15 minutes, and centrifuged at 4000×g for 15 min at 5° C. The supernatant was passed through 0.20 um Millipore Stericup PES filters, and, immediately post filtration, the acidified clarified cell-free harvest was neutralized with 2M Tris to pH 7.1±0.2. The cell free harvest was transferred to PETG bottles and stored at −80° C. until analysis.

6.6.2. Experimental Design

As detailed in Table 7, manganese chloride was supplemented at the following concentrations in both production and feed media: 0, 0.2, and 0.5 μM. Galactose was supplemented at the following levels in both production and feed media: 0, 1, 4, 5, and 10 mM. Manganese chloride and galactose were added in a full factorial, two level DOE design for the 0, 1, and 4 mM galactose conditions and all concentrations of manganese chloride. Individual and combined additions of manganese chloride and galactose were studied using a comprehensive design divided into 2 sets of experiments. Each experiment had a control culture for direct comparison of culture growth, productivity, and product quality. Production medium for control cultures was not supplemented with manganese chloride or galactose.

TABLE 7

Experimental design for Example 6

| | Manganese (μM) | Galactose (mM) | ID |
|---|---|---|---|
| Block I | 0 | 0 | Mn(0) Gal(0) |
| | 0 | 5 | Mn(0) Gal(5) |
| | 0 | 10 | Mn(0) Gal(10) |
| Block II | 0 | 0 | Mn(0) Gal(0) |
| | 0.2 | 0 | Mn(0.2) Gal(0) |
| | 0.5 | 0 | Mn(0.5) Gal(0) |
| | 0 | 1 | Mn(0) Gal(1) |
| | 0.2 | 1 | Mn(0.2) Gal(1) |
| | 0.5 | 1 | Mn(0.5) Gal(1) |
| | 0 | 4 | Mn(0) Gal(4) |
| | 0.2 | 4 | Mn(0.2) Gal(4) |
| | 0.5 | 4 | Mn(0.5) Gal(4) |

6.6.3. Culture Growth & Productivity

Figure 19A:
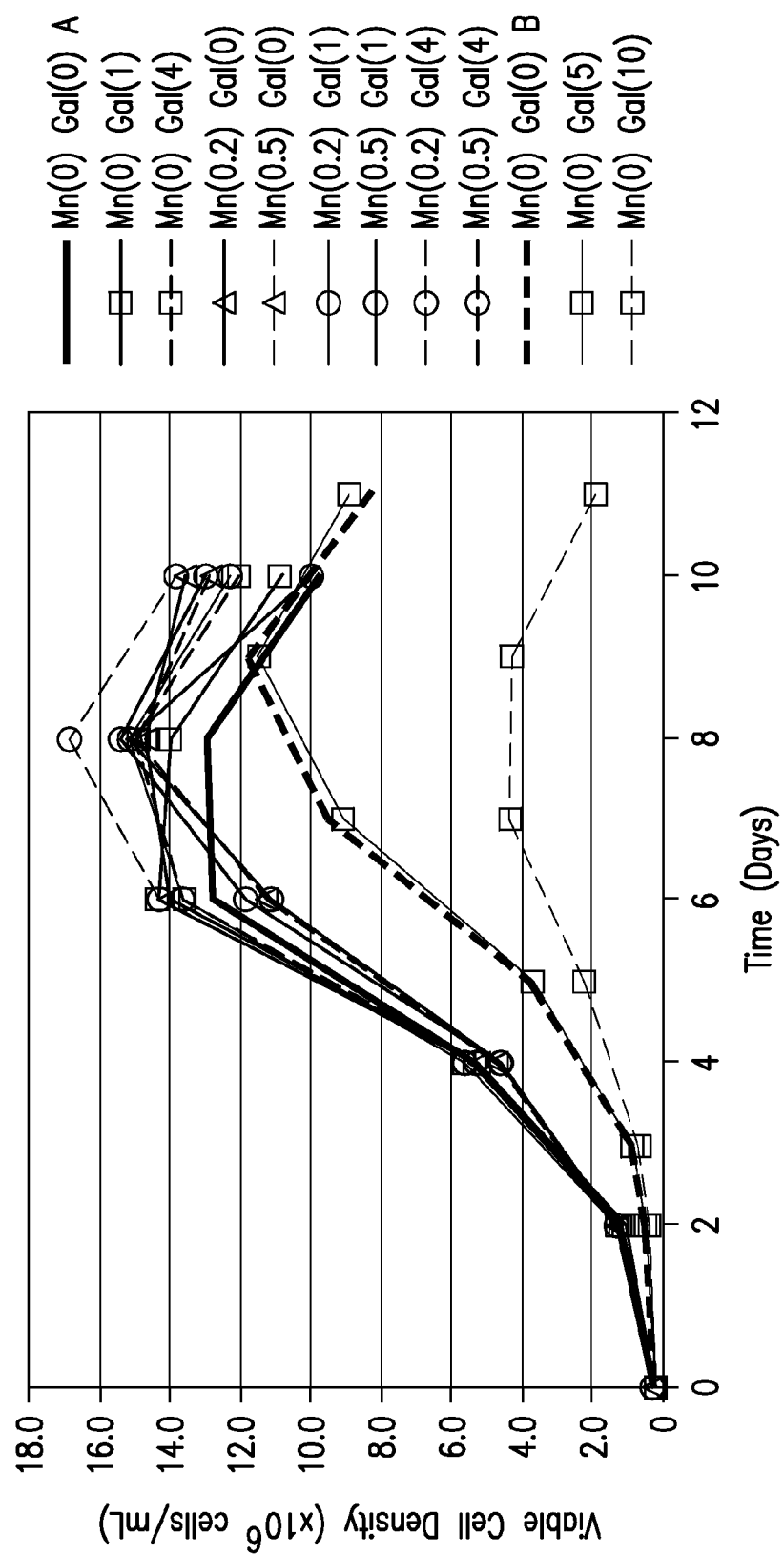
Figure 19B:
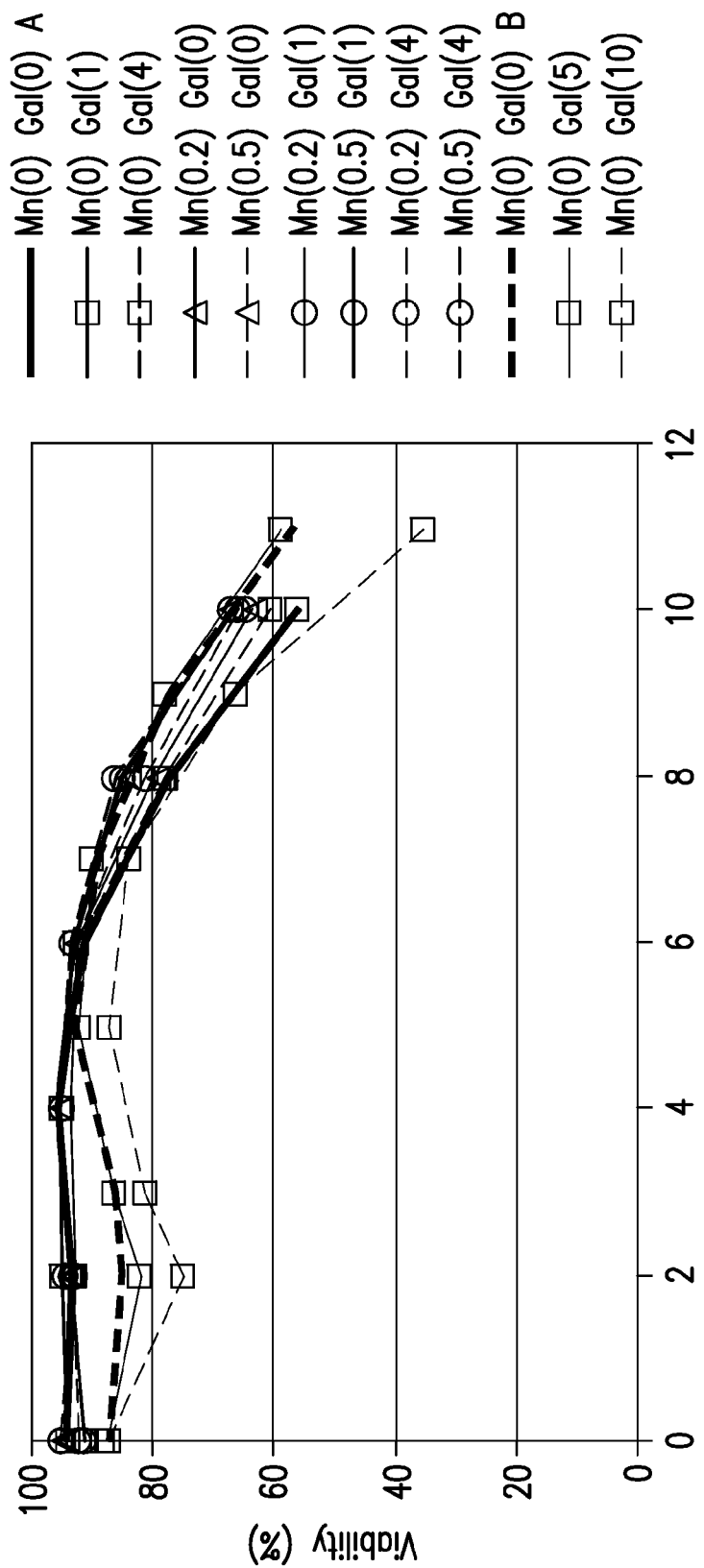
Figure 19C:
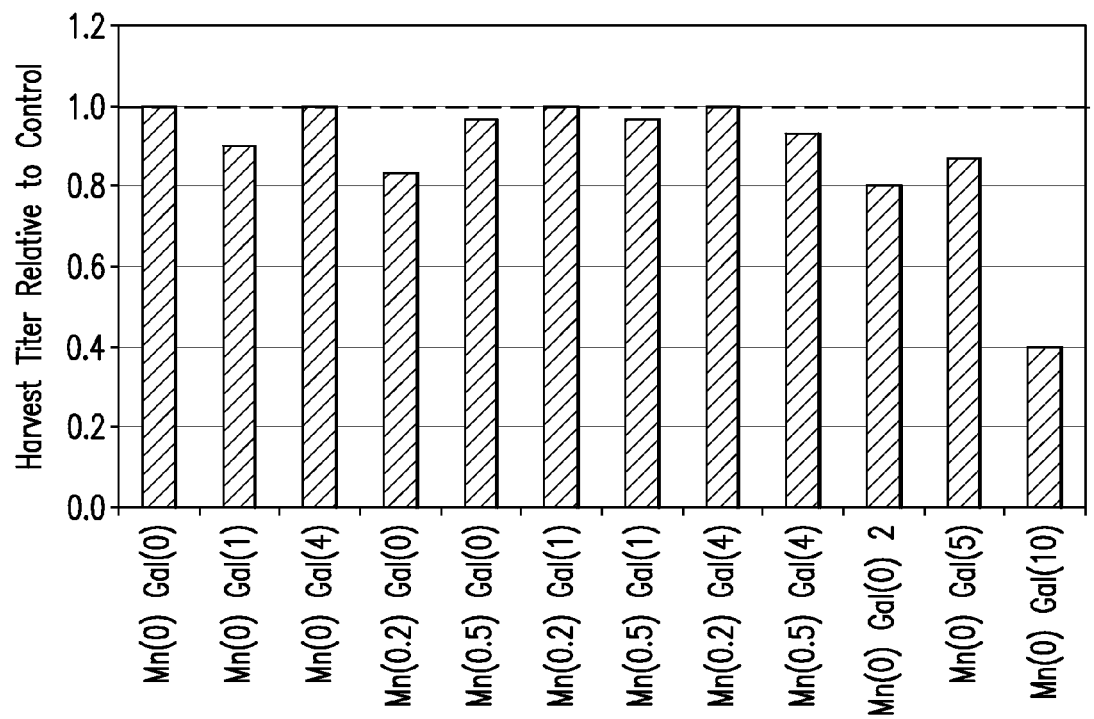

Culture growth and viability profiles in production media supplemented with galactose in the 0 to 5 mM concentration range and/or manganese chloride up to 0.5 μM concentration were comparable to the control condition without manganese or galactose added (FIGS. 19A, 19B). The addition of galactose at 10 mM concentration had a detrimental effect on culture growth and productivity. The cultures in the Block I experiment had a lower maximum VCD and overall lower viability than the cultures in the Block II experiment. All cultures in the Block II experiment showed similar VCD and viability profiles. Harvest titer for most experimental conditions was comparable to the harvest titer for the control condition except for the titer of the culture supplemented with 10 mM galactose, which was 60% lower (FIG. 19C).

6.6.4. Oligosaccharide Analysis

In this example, the modulation of galactosylation by the addition of manganese chloride and/or galactose to chemically defined PFBM-3/PFFM-4 media was explored using an adalimumab-producing NSO cell line in a fed-batch process in shake flasks.

The addition of manganese chloride alone within the range of 0 to 0.5 μM to CDM PFBM-3/PFFM-4 decreased the NGA2F+NGA2F-GlcNac sum in a concentration dependent manner and increased the NA1F+NA2F sum by approximately the same percentage. A maximum decrease of 18% in the NGA2F+NGA2F-GlcNac sum and a corresponding increase of 20% in the NA1F+NA2F sum were observed with the addition of 0.5 µM manganese chloride (FIG. 20). Manganese doses greater than 0.5 µM were not explored further due to cytotoxicity effects. Similarly, a concentration dependent decrease in the NGA2F+NGA2F-GlcNac sum and a corresponding increase in the NA1F+NA2F sum were observed with the addition of galactose alone in the range of 0 to 10 mM to CDM PFBM-3/PFFM-4. A maximum decrease of 14% in the NGA2F+NGA2F-GlcNac sum and a corresponding increase of 15% in the NA1F+NA2F sum was observed with the addition of 10 mM galactose.

The effect on modulation of galactosylation of adalimumab produced in a NSO cell line in CDM PFBM-3/PFFM-4 supplemented with manganese chloride and galactose was synergistic (FIG. 21). For example, addition of 0.2 µM manganese chloride alone reduced the NGA2F+NGA2F-GlcNac sum by 12%, and addition of 4 mM galactose alone decreased the NGA2F+NGA2F-GlcNac sum by 2%. However, the combined addition of manganese chloride and galactose at these same concentrations (i.e. 0.2 µM manganese+4 mM galactose) led to a 19% reduction in the NGA2F+NGA2F-GlcNac sum, 5% higher than their combined individual contributions. A maximum decrease of ~26% in the NGA2F+NGA2F-GlcNac sum and a corresponding 28% increase in the NA1F+NA2F sum were observed with the combined addition of 0.5 µM manganese chloride and 4 mM galactose.

6.7. Example 7

6.7.1. Materials & Methods

In the study summarized in this example, we investigated the effects on product quality attributes resulting from the addition of manganese chloride and/or galactose to chemically defined Life Technologies Gibco GIA-1 media in a CHO cell line producing a monoclonal antibody generically named mAb #1.

Growth and production media for the CHO cell line producing mAb #1 were prepared using a proprietary Life Technologies Gibco chemically defined media, GIA-1. Production media only was supplemented with Manganese (II) Chloride (Sigma M1787—100 mL; 1.0 M±0.1 M) and D(+) Galactose (Sigma G5388—1 kg) according to the experimental design described in Table 8. All media were filtered through Corning 0.5 L or 1 L filter systems (0.22 µm PES) and stored at 4° C. until use.

Upon thaw, cells were expanded for 6 (3 day each) passages in a combination of 250 mL, 500 mL, and 1000 mL Corning vented non-baffled shake flasks. Production cultures were initiated in duplicate 500 mL Corning vented non-baffled shake flasks (200 mL working volume) at an initial VCD of approximately 0.5×106 cells/mL. Cultures were maintained on orbital shakers at 125 RPM in a dry incubator at 35° C. and 5% $CO_2$. A glucose solution (1.25% (v/v) of 40% solution) was fed when the media glucose concentration fell below 3 g/L.

6.7.2. Experimental Design

As detailed in Table 8, manganese chloride was supplemented at the following levels in production media: 0, 10, 20, and 40 µM. Galactose was supplemented at the following levels in production media: 0, 10, 20, and 100 mM. Production media for the control cultures was not supplemented with manganese chloride or galactose.

TABLE 8

| Experimental design for Example 7 | | |
|---|---|---|
| Manganese (µM) | Galactose (mM) | ID |
| 0 | 0 | Mn(0) Gal(0) |
| 0 | 10 | Mn(0) Gal(10) |
| 0 | 20 | Mn(0) Gal(20) |
| 0 | 40 | Mn(0) Gal(40) |
| 10 | 0 | Mn(10) Gal (0) |
| 20 | 0 | Mn(20) Gal(0) |
| 40 | 0 | Mn(40) Gal(0) |
| 10 | 10 | Mn(10) Gal(10) |
| 20 | 20 | Mn(20) Gal(20) |
| 40 | 40 | Mn(40) Gal(40) |

6.7.3. Culture Growth & Productivity

Figure 22A:
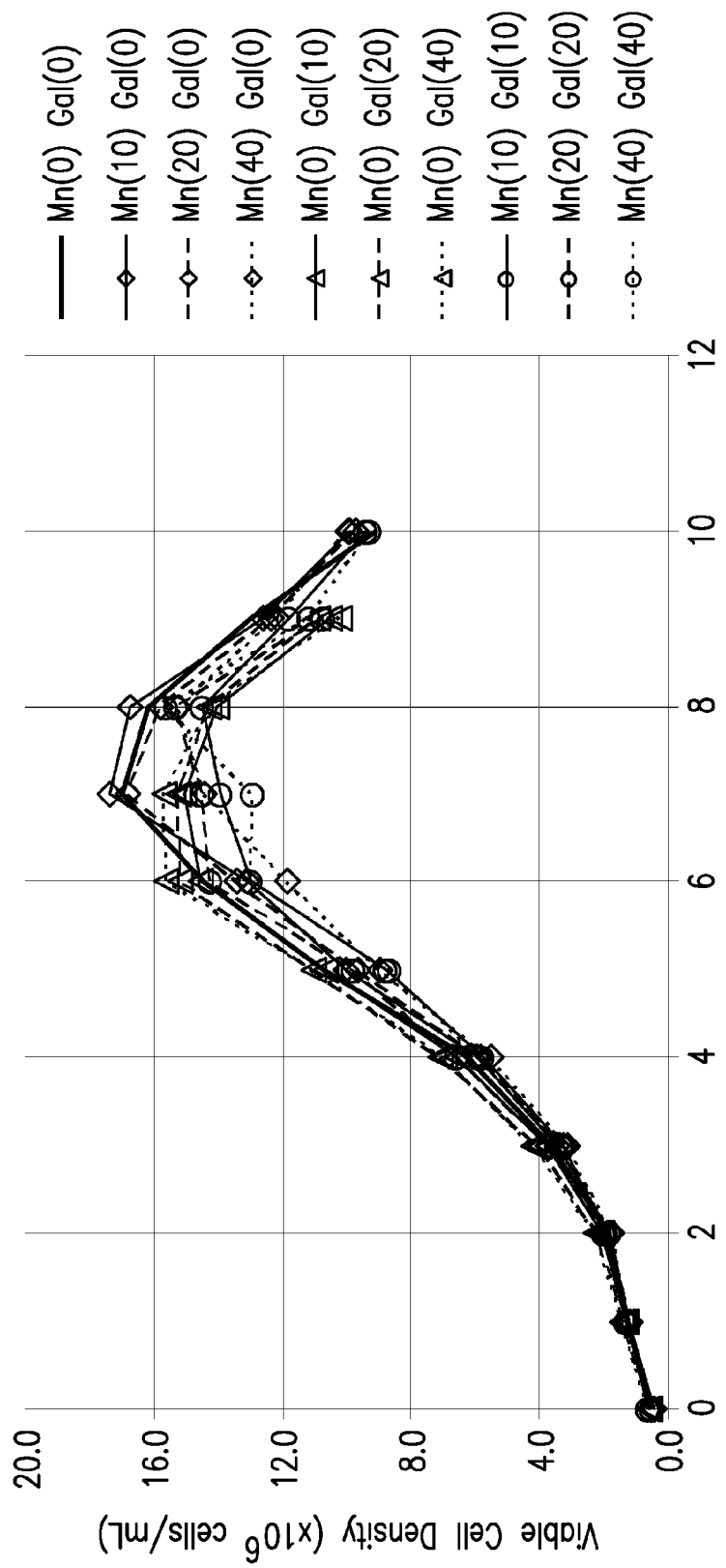
Figure 22B:
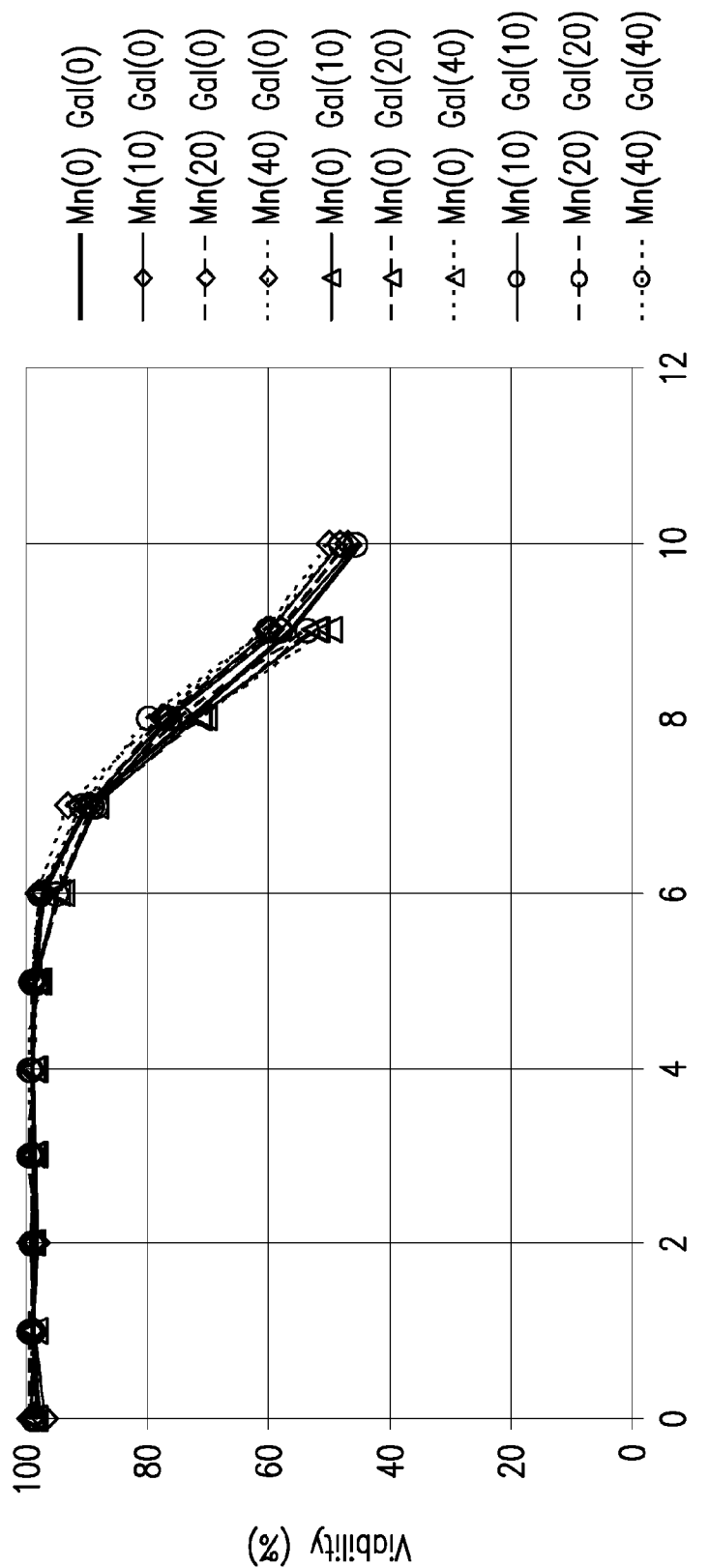

Cultures supplemented with manganese chloride alone in the concentration range of 0 to 20 µM grew comparable to the control cultures (FIG. 22A). Cultures supplemented with galactose alone or with the combination of 20 µM manganese and 20 mM galactose grew to a lower maximum VCD compared to the control, but had the same growth rate until the peak VCD was achieved on production day 6. These cultures ended a day earlier, on production day 9 (FIG. 22B). Cultures supplemented with 40 µM manganese chloride and galactose at all levels studied along with the culture supplemented with 10 µM manganese chloride and 10 mM galactose experienced slower growth and decreased peak VCD compared to the control. Harvest titer was 3-24% lower than the control condition (data not shown).

6.7.4. Oligosaccharide Analysis

In this example, the modulation of galactosylation by the addition of manganese chloride and/or galactose to chemically defined Life Technologies Gibco GIA-1 media was explored using a CHO cell line producing the monoclonal antibody mAb #1.

The addition of manganese chloride alone within the range of 0 to 40 µM to production CDM GIA-1 decreased the NGA2F+NGA2F-GlcNac sum by a maximum of 26% (FIG. 23). A comparable maximum increase of 27% in the NA1F+NA2F sum was achieved. Addition of galactose alone up to a maximum concentration of 40 mM yielded a maximum decrease of 12% in the NGA2F+NGA2F-GlcNac sum and a corresponding 13% maximum increase in the NA1F+NA2F sum in a concentration dependent manner.

The combined addition of galactose and manganese chloride to production CDM GIA-1 resulted in a greater percent reduction in the NGA2F+NGA2F-GlcNac sum and, correspondingly, a greater percent increase in the NA1F+NA2F sum as compared to the addition of either component alone (FIG. 24). For example, the addition of 40 µM manganese chloride alone reduced the NGA2F+NGA2F-GlcNac sum by 20%, and the addition of 40 mM galactose alone decreased the NGA2F+NGA2F-GlcNac sum by 12%. However, the combined addition of manganese chloride and galactose at these same concentrations (i.e. 40 µM manganese+40 mM galactose) led to a 27% decrease in the NGA2F+NGA2F-GlcNac sum. The highest percentage decrease of 32% in the NGA2F+NGA2F-GlcNac sum and the corresponding increase of 30% in the NA1F+NA2F sum were observed for the culture supplemented with 20 µM manganese chloride and 20 mM galactose.

6.8. Example 8

6.8.1. Materials & Methods

In the study summarized in this example, we investigated the effects on product quality attributes resulting from the addition of manganese chloride and/or galactose to chemically defined Life Technologies Gibco GIA-1 media in a CHO cell line producing the monoclonal antibody generically named mAb #2 in a fed-batch process in 3 L bioreactors.

Growth and production media for the mAb #2 producing CHO cell line were prepared using the proprietary Life Technologies Gibco chemically defined media, GIA-1. Basal production and feed media were supplemented with Manganese (II) Chloride (Sigma M3634) and D(+)Galactose (Sigma G5388—1 kg) according to the experimental design described in Table 9.

Upon thaw, cells were expanded in Corning vented non-baffled shake flasks maintained on orbital shakers at 140 RPM, and in 10 L cell bags (2 L working volume) maintained at 25 RPM, 7° angle, 0.25 SLPM airflow in a dry incubator at 36° C. and 5% CO2. Production cultures were initiated in 3 L bioreactors (1.5 L initial working volume) at 36° C., 25% dissolved oxygen, 200 RPM, and pH 7.0. The chemically-defined feed from Life Technologies Gibco JCL-5 was added as follows: 3% (v/v)—day 3, 5%—day 5, 7%—day 7, 10%—day 9, and 10%—day 11. Additional 400 g/L glucose was added to the bioreactor cultures as needed to ensure the glucose levels did not deplete. Bioreactors were harvested at viability of approximately 70% or below or on production day 15, whichever condition occurred first.

6.8.2. Experimental Design

As detailed in Table 9, manganese chloride was supplemented at the following concentrations in both production and feed media: 0, 25, 50, and 75 µM. Galactose was supplemented at 0, 15, 30, and 60 mM concentrations in both production and feed media. In addition, a combined manganese chloride and galactose supplementation strategy was utilized for the production basal and feed media at 25 µM manganese chloride+15 mM galactose, and 50 µM manganese chloride+30 mM galactose. Basal and feed media for the control cultures were not supplemented with manganese chloride or galactose.

TABLE 9

Experimental design for Example 8

| Manganese (µM) | Galactose (mM) | ID |
|---|---|---|
| 0 | 0 | Mn(0) Gal(0) |
| 25 | 0 | Mn(25) Gal(0) |
| 50 | 0 | Mn(50) Gal(0) |
| 75 | 0 | Mn(75) Gal(0) |
| 0 | 15 | Mn(0) Gal(15) |
| 0 | 30 | Mn(0) Gal(30) |
| 0 | 60 | Mn(0) Gal(60) |
| 25 | 15 | Mn(25) Gal(15) |
| 50 | 30 | Mn(50) Gal(30) |

6.8.3. Culture Growth & Productivity

Figure 25A:
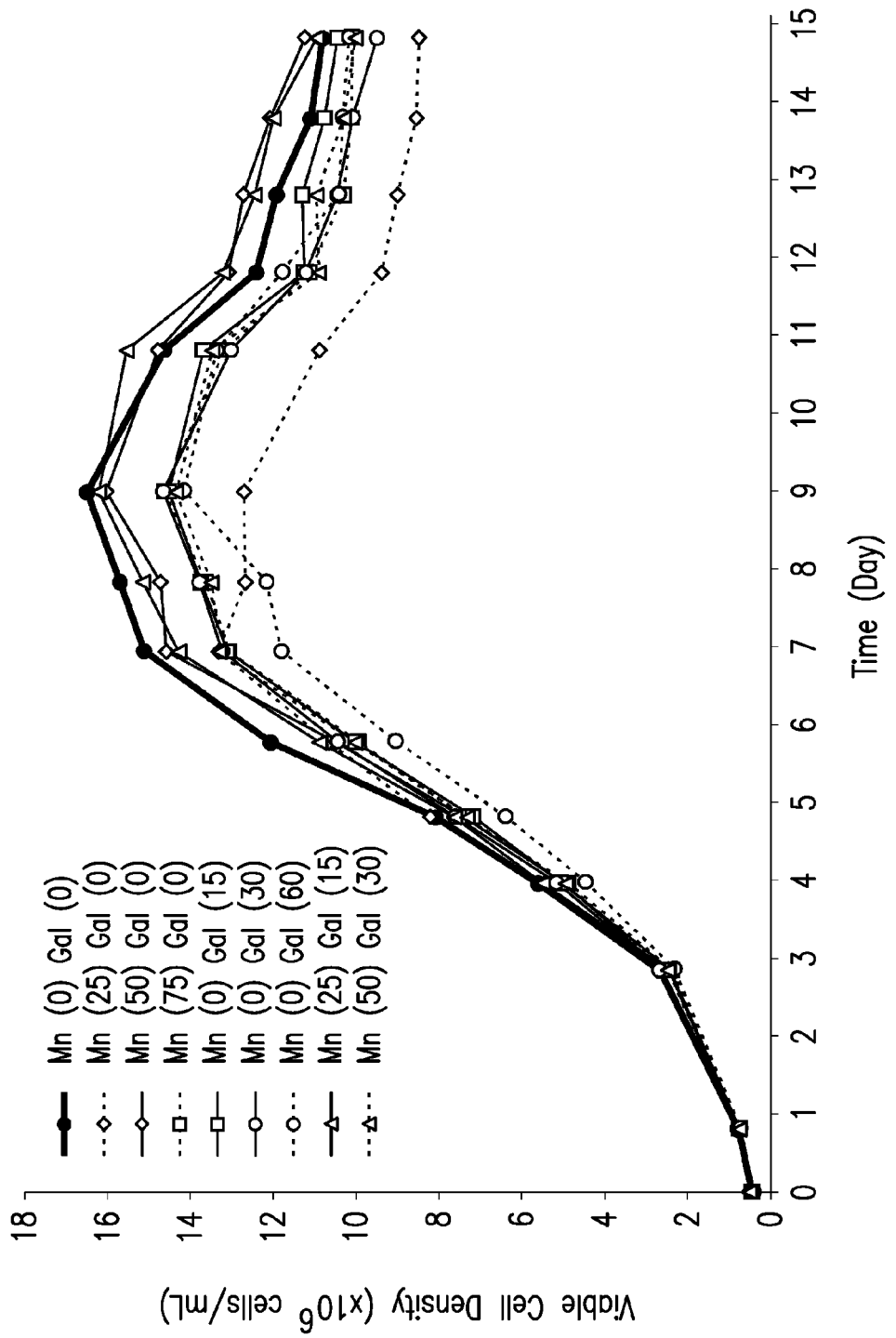
Figure 25B:
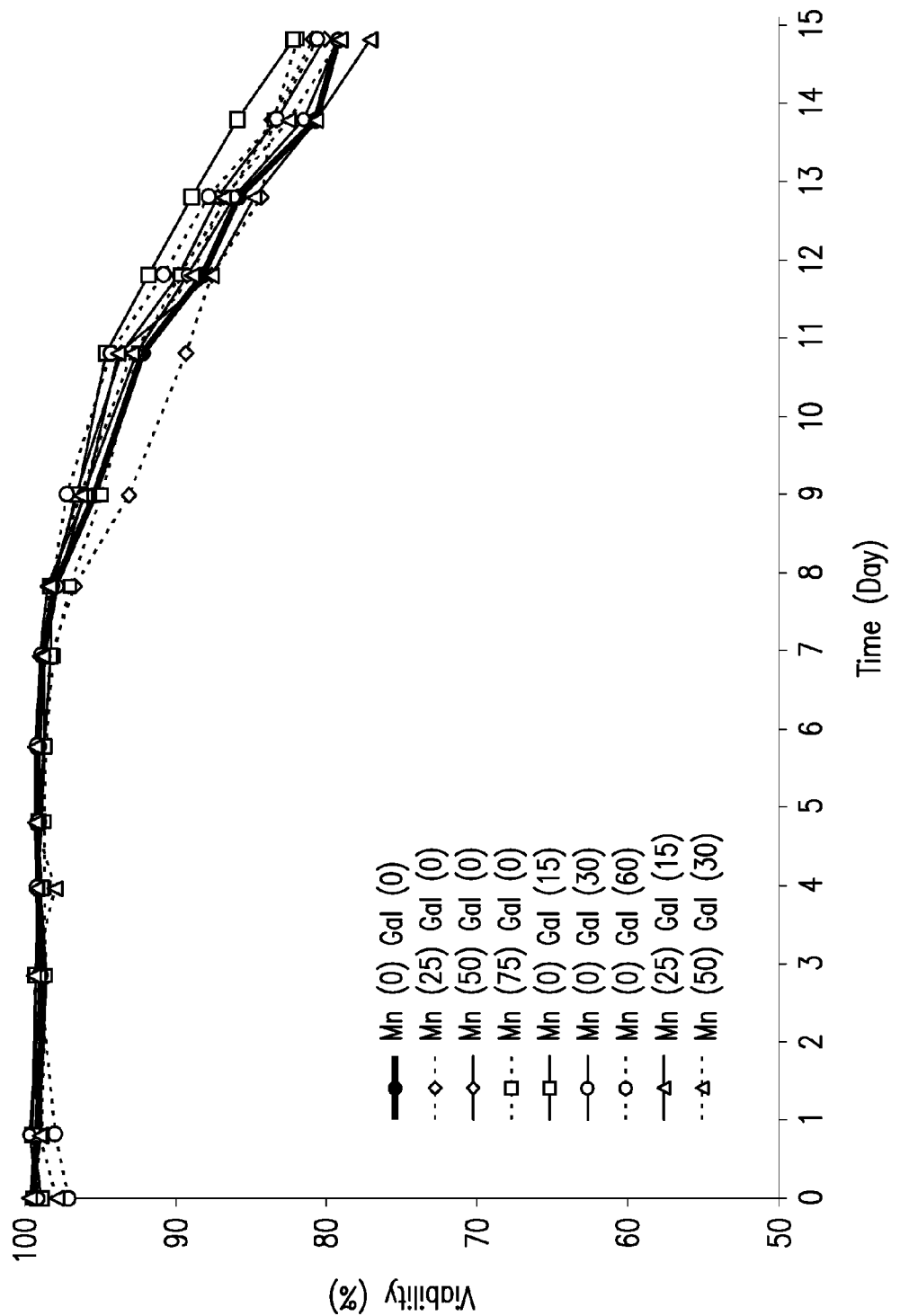
Figure 25C:
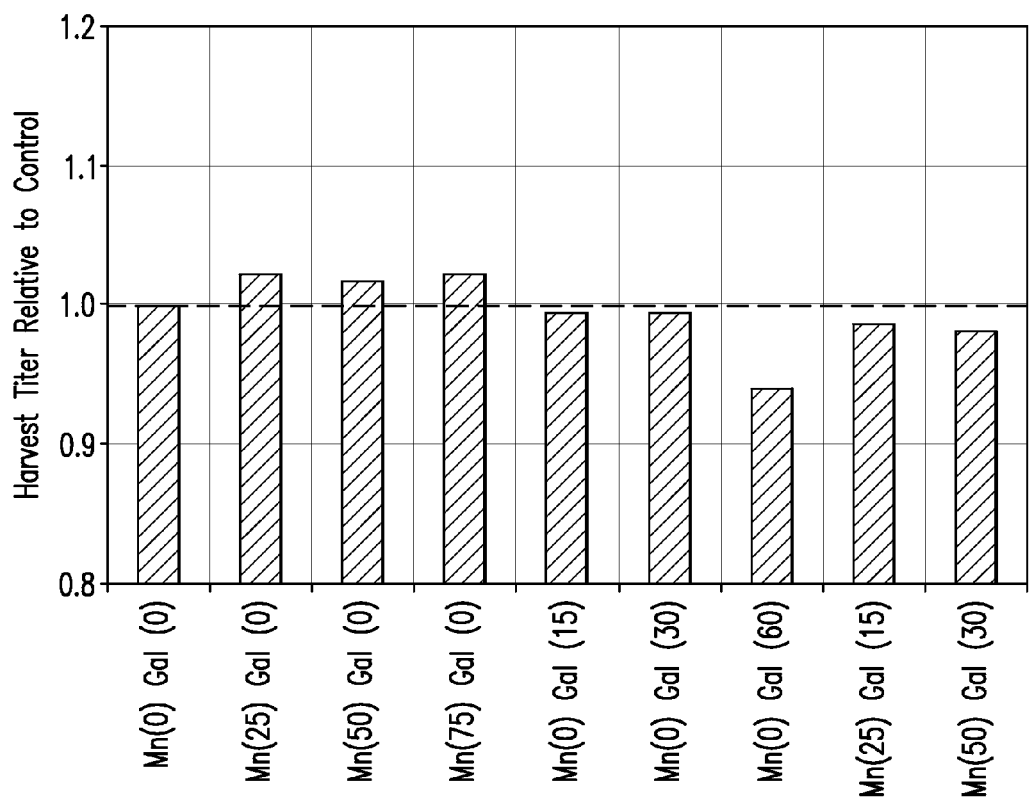

Growth profiles of most cultures supplemented with galactose in the 0 to 60 mM concentration range and/or manganese chloride in the 0 to 75 µM range were comparable to the control culture except for the culture supplemented with 25 µM manganese chloride alone which grew slower after production day 7 (FIG. 25A). However, increasing the amount of manganese chloride supplemented to production CDM GIA-1 to 50 µM or 75 µM resulted in cultures with growth profiles comparable to the control culture. Viability profiles and harvest titer were comparable to the control condition (FIGS. 25B, 25C).

6.8.4. Oligosaccharide Analysis

In this example, the modulation of galactosylation with the addition of manganese chloride and/or galactose to chemically defined media GIA-1 was explored using a CHO cell line producing the monoclonal antibody mAb #2.

The addition of manganese chloride alone in the range of 0 to 75 µM to production CDM GIA-1 decreased the NGA2F+NGA2F-GlcNac sum by a maximum of 18% (FIG. 26). A comparable maximum increase of 16% in the NA1F+NA2F sum was achieved. Addition of galactose alone up to a maximum concentration of 60 mM yielded a maximum decrease of 12% in the NGA2F+NGA2F-GlcNac sum and a corresponding 11% maximum increase in the NA1F+NA2F sum.

When manganese chloride and galactose were supplemented together into the basal and feed media, the results demonstrated at least an additive effect and sometimes a synergistic effect towards the decrease in the NGA2F+NGA2F-GlcNAc and the increase in the NA1F+NA2F oligosaccharides (FIG. 27). The synergistic effect was observed for the condition supplemented with 25 µM manganese chloride and 15 mM galactose. The observed 22% decrease in the NGA2F+NGA2F-GlcNac sum was 5% more than the sum of the decrease observed with the addition of 25 µM manganese chloride alone (10%) and 15 mM galactose alone (7%). The additive effect was observed for the condition supplemented with 50 µM manganese chloride and 30 mM galactose. The observed 28% decrease in the NGA2F+NGA2F-GlcNAc sum was comparable to the sum of the decrease observed with the addition of 50 µM manganese chloride alone (18%) and 30 mM galactose alone (12%). A maximum decrease of 28% in the NGA2F+NGA2F-GlcNac and a corresponding 25% maximum increase in the NA1F+NA2F sum compared to the control condition was observed with the combined addition of 50 µM manganese chloride and 30 mM galactose to chemically defined GIA-1 media.

All patents, patent applications, publications, product descriptions and protocols, cited in this specification are hereby incorporated by reference in their entirety. In case of a conflict in terminology, the present disclosure controls.

While it will be apparent that the invention herein described is well calculated to achieve the benefits and advantages set forth above, the present invention is not to be limited in scope by the specific embodiments described herein. It will be appreciated that the invention is susceptible to modification, variation and change without departing from the spirit thereof.

What is claimed is:

1. A method for increasing the galactosylation level of a recombinantly expressed adalimumab, comprising supplementing a media used in the expression of the recombinantly expressed adalimumab with a sufficient amount of a manganese supplement to achieve a manganese concentration in the media of 0.2-100 µM and a sufficient amount of a galactose supplement to achieve a galactose concentration in the media of 1-100 mM, thereby increasing the galactosylation level of the recombinantly expressed adalimumab, wherein the galactosylation level of a recombinantly expressed adalimumab is increased as compared to the galactosylation level of adalimumab recombinantly expressed in media which is not supplemented with said manganese supplement and said galactose supplement.

2. The method of claim 1, wherein the manganese supplement is a biologically acceptable manganese salt.

3. The method of claim 2, wherein the biologically acceptable manganese salt is manganese (II) chloride.

4. The method of claim 1, wherein the galactose supplement is a biologically acceptable galactose containing compound.

5. The method of claim 4, wherein the biologically acceptable galactose containing compound is D-(+)-galactose.

6. The method of claim 1, wherein the media is supplemented with a sufficient amount of the manganese supplement to achieve a manganese concentration in the media selected from the group consisting of 0.2, 0.5, 1.0, 10, 20, 25, 40, 50, 60, 75, 80, and 100 µM.

7. The method of claim 1, wherein the media is supplemented with a sufficient amount of the galactose supplement to achieve a galactose concentration in the media selected from the group consisting of 1, 4, 5, 10, 15, 20, 30, 40, 60, and 100 mM.

8. The method of claim 1, wherein the media is supplemented with a sufficient amount of the manganese supplement and the galactose supplement to achieve a manganese (Mn) and a galactose (Gal) concentration in the media selected from the group consisting of 0.2/1, 0.2/4, 0.2/30, 0.5/1, 0.5/4, 0.5/30, 10/10, 10/20, 10/40, 20/10, 20/20, 20/40, 25/15, 40/10, 40/20, 40/40, 40/100, 50/30, 60/20, 60/40, 60/100, 80/20, 80/40, 80/100, 100/20, 100/40, and 100/100 Mn (µM)/Gal (mM).

9. The method of claim 1, wherein the method further comprises culturing in the media a mammalian cell expressing adalimumab, wherein the media is selected from the group consisting of chemically defined (CD) cell culture media and hydrolysate-based media.

10. The method of claim 9, wherein the culturing is done in a suspension culture.

11. The method of claim 9, wherein the mammalian cell has been adapted for growth in a CD cell culture media.

12. The method of claim 9, wherein the mammalian cell is a CHO cell.

13. The method of claim 9, wherein the mammalian cell is an NS0 cell.

14. The method of claim 9, wherein the mammalian cell is cultured for at least 4 days.

15. The method of claim 9, wherein the mammalian cell is cultured for up to 12 days.

16. The method of claim 9, further comprising recovering said adalimumab from the media.

17. The method of claim 16, further comprising purifying said adalimumab from the media.

18. The method of claim 17, further comprising quantifying the levels of galactose-containing fucosylated biantennary oligosaccharides (NA1F and NA2F) and/or agalactosyl fucosylated biantennary oligosaccharides (NGA2F and NGA2F-GlcNAc) present on said adalimumab.

19. The method of claim 9, wherein the said culturing is done as a fed-batch process.

20. The method of claim 9, wherein said culturing is done in a bioreactor.

21. The method of claim 1, wherein manganese and galactose are present in the media at a concentration sufficient to produce a composition comprising adalimumab in which at least 10% of the total N-linked oligosaccharides present on said adalimumab are of a galactose-containing fucosylated biantennary oligosaccharide (NA1F+NA2F) form.

22. The method of claim 21, wherein at least 15% of the total N-linked oligosaccharides present on said adalimumab are of a galactose-containing fucosylated biantennary oligosaccharide (NA1F+NA2F) form.

23. The method of claim 21, wherein at least 20% of the total N-linked oligosaccharides present on said adalimumab are of a galactose-containing fucosylated biantennary oligosaccharide (NA1F+NA2F) form.

24. The method of claim 1, wherein the media is supplemented with a sufficient amount of the manganese supplement to achieve a manganese concentration in the media of 0.2-40 µM.

25. The method of claim 1, wherein the media is supplemented with a sufficient amount of the manganese supplement to achieve a manganese concentration in the media of 40-100 µM.

26. The method of claim 1, wherein the media is supplemented with a sufficient amount of the manganese supplement to achieve a manganese concentration in the media of 40-60 µM.

27. The method of claim 1, wherein the media is supplemented with a sufficient amount of the manganese supplement to achieve a manganese concentration in the media of 50-80 µM.

28. The method of claim 1, wherein the media is supplemented with a sufficient amount of the manganese supplement to achieve a manganese concentration in the media of 75-100 µM.

29. The method of claim 1, wherein the media is supplemented with a sufficient amount of the galactose supplement to achieve a galactose concentration in the media of 10-100 mM.

30. The method of claim 1, wherein the media is supplemented with a sufficient amount of the galactose supplement to achieve a galactose concentration in the media of 1-60 mM.

31. The method of claim 1, wherein the media is supplemented with a sufficient amount of the galactose supplement to achieve a galactose concentration in the media of 60-100 mM.

32. The method of claim 1, wherein the media is supplemented with a sufficient amount of the galactose supplement to achieve a galactose concentration in the media of 10-60 mM.

33. The method of claim 1, wherein the media is selected from the group consisting of production media and feed media.

34. A method for increasing the galactosylation level of a recombinantly expressed adalimumab, comprising supplementing a media used in the expression of the recombinantly expressed adalimumab with a sufficient amount of a manganese supplement to achieve a manganese concentration in the media of 0.2-100 µM and a sufficient amount of a galactose supplement to achieve a galactose concentration in the media of 1-100 mM and culturing a cell expressing adalimumab in said media, thereby increasing the galactosylation level of the recombinantly expressed adalimumab, wherein the galactosylation level of a recombinantly expressed adalimumab is increased as compared to the galactosylation level of adalimumab recombinantly expressed in media which is not supplemented with said manganese supplement and said galactose supplement.

35. The method of claim 34, wherein the manganese supplement is a biologically acceptable manganese salt.

36. The method of claim 35, wherein the biologically acceptable manganese salt is manganese (II) chloride.

37. The method of claim 34, wherein the galactose supplement is a biologically acceptable galactose containing compound.

38. The method of claim 37, wherein the biologically acceptable galactose containing compound is D-(+)-galactose.

39. The method of claim 34, wherein the media is supplemented with a sufficient amount of the manganese supplement to achieve a manganese concentration in the media selected from the group consisting of 0.2, 0.5, 1.0, 10, 20, 25, 40, 50, 60, 75, 80, and 100 µM.

40. The method of claim 34, wherein the media is supplemented with a sufficient amount of the galactose supplement to achieve a galactose concentration in the media selected from the group consisting of 1, 4, 5, 10, 15, 20, 30, 40, 60, and 100 mM.

41. The method of claim 34, wherein the media is supplemented with a sufficient amount of the manganese supplement and the galactose supplement to achieve a manganese (Mn) and a galactose (Gal) concentration in the media selected from the group consisting of 0.2/1, 0.2/4, 0.2/30, 0.5/1, 0.5/4, 0.5/30, 10/10, 10/20, 10/40, 20/10, 20/20, 20/40, 25/15, 40/10, 40/20, 40/40, 40/100, 50/30, 60/20, 60/40, 60/100, 80/20, 80/40, 80/100, 100/20, 100/40, and 100/100 Mn (µM)/Gal (mM).

42. The method of claim 34, wherein said cell is a mammalian cell and wherein the media is selected from the group consisting of chemically defined (CD) cell culture media and hydrolysate-based media.

43. The method of claim 42, wherein the mammalian cell has been adapted for growth in a CD cell culture media.

44. The method of claim 42, wherein the mammalian cell is a CHO cell.

45. The method of claim 42, wherein the mammalian cell is an NS0 cell.

46. The method of claim 42, wherein the mammalian cell is cultured for at least 4 days.

47. The method of claim 42, wherein the mammalian cell is cultured for up to 12 days.

48. The method of claim 34, wherein manganese and galactose are present in the media at a concentration sufficient to produce a composition comprising adalimumab in which at least 10% of the total N-linked oligosaccharides present on said adalimumab are of a galactose-containing fucosylated biantennary oligosaccharide (NA1F+NA2F) form.

49. The method of claim 48, wherein at least 15% of the total N-linked oligosaccharides present on said adalimumab are of a galactose-containing fucosylated biantennary oligosaccharide (NA1F+NA2F) form.

50. The method of claim 48, wherein 20% of the total N-linked oligosaccharides present on said adalimumab are of a galactose-containing fucosylated biantennary oligosaccharide (NA1F+NA2F) form.

51. The method of claim 34, further comprising recovering said adalimumab from the media.

52. The method of claim 51, further comprising purifying said adalimumab from the media.

53. The method of claim 52, further comprising quantifying the levels of galactose-containing fucosylated biantennary oligosaccharides (NA1F and NA2F) and/or agalactosyl fucosylated biantennary oligosaccharides (NGA2F and NGA2F-GlcNAc) present on said adalimumab.

54. The method of claim 34, wherein the media is supplemented with a sufficient amount of the manganese supplement to achieve a manganese concentration in the media of 0.2-40 µM.

55. The method of claim 34, wherein the media is supplemented with a sufficient amount of the manganese supplement to achieve a manganese concentration in the media of 40-100 µM.

56. The method of claim 34, wherein the media is supplemented with a sufficient amount of the manganese supplement to achieve a manganese concentration in the media of 40-60 µM.

57. The method of claim 34, wherein the media is supplemented with a sufficient amount of the manganese supplement to achieve a manganese concentration in the media of 50-80 µM.

58. The method of claim 34, wherein the media is supplemented with a sufficient amount of the manganese supplement to achieve a manganese concentration in the media of 75-100 µM.

59. The method of claim 34, wherein the media is supplemented with a sufficient amount of the galactose supplement to achieve a galactose concentration in the media of 10-100 mM.

60. The method of claim 34, wherein the media is supplemented with a sufficient amount of the galactose supplement to achieve a galactose concentration in the media of 1-60 mM.

61. The method of claim 34, wherein the media is supplemented with a sufficient amount of the galactose supplement to achieve a galactose concentration in the media of 60-100 mM.

62. The method of claim 34, wherein the media is supplemented with a sufficient amount of the galactose supplement to achieve a galactose concentration in the media of 10-60 mM.

63. The method of claim 34, wherein the said culturing is done as a fed-batch process.

64. The method of claim 34, wherein the media is selected from the group consisting of production media and feed media.

65. The method of claim 34, wherein said culturing is done in a bioreactor.

\* \* \* \* \*